(12) United States Patent
Jimenez et al.

(10) Patent No.: US 8,198,275 B2
(45) Date of Patent: Jun. 12, 2012

(54) ADAMANTYL DIAMIDE DERIVATIVES AND USES OF SAME

(75) Inventors: Hermogenes N. Jimenez, Belleville, NJ (US); Guiying Li, River Edge, NJ (US); Dario Doller, Sparta, NJ (US); Michel Grenon, Saddle Brook, NJ (US); Andrew D. White, Pinckney, MI (US); Gil Ma, Englewood, NJ (US); Maojun Guo, Pudong (CN)

(73) Assignee: H. Lundbeck A/S, Valby-Copenhagen (DK)

( * ) Notice: Subject to any disclaimer, the term of this patent is extended or adjusted under 35 U.S.C. 154(b) by 0 days.

(21) Appl. No.: 13/075,213

(22) Filed: Mar. 30, 2011

(65) Prior Publication Data

US 2011/0178086 A1 Jul. 21, 2011

Related U.S. Application Data

(62) Division of application No. 12/504,711, filed on Jul. 17, 2009, now Pat. No. 7,947,680.

(60) Provisional application No. 61/083,563, filed on Jul. 25, 2008, provisional application No. 61/160,804, filed on Mar. 17, 2009.

(51) Int. Cl.
*A61K 31/5377* (2006.01)
*A61K 31/497* (2006.01)
*A61K 31/506* (2006.01)
*A61K 31/4709* (2006.01)
*A61K 31/444* (2006.01)
*A61K 31/4155* (2006.01)
*A61K 31/16* (2006.01)

(52) U.S. Cl. ............... 514/235.5; 514/255.05; 514/256; 514/314; 514/332; 514/406; 514/616

(58) Field of Classification Search ............... 514/235.5, 514/332, 314, 255.05, 256, 406, 616, 237.2
See application file for complete search history.

(56) References Cited

U.S. PATENT DOCUMENTS 3,053,907 A 9/1962 Smith et al.

FOREIGN PATENT DOCUMENTS

| EP | 0897747 A1 | 2/1999 |
|---|---|---|
| JP | 2003050441 A | 2/2003 |
| WO | 0073283 A1 | 12/2000 |
| WO | 03068726 A1 | 8/2003 |
| WO | 2006090244 A1 | 8/2006 |

OTHER PUBLICATIONS

"Autism," [retrieved on May 14, 2008]. Retrieved online via Internet, URL: http://www.nlm.nih.gov/medlineplus/autism.html.*
Aggleton J.P., et al., 1986. "The Effects of Hippocampal Lesions Upon Spatial and Non-Spatial Tests of Working Memory," Behavioral Brain Research, 19(2):133-146.
Annett, L.E., 1994. "Behavioral Assessment of the Effects of Embryonic Nigral Grafts in Marmosets with Unilateral 6-OHDA Lesions of the Nigrostriatal Pathway," Experimental Neurology, 125:228-246.
Bach, P., et al., 2007. "Metabotropic Glutamete Receptor 5 Modulators and Their Potential Therapeutic Applications," Expert Opinion on Therapeutic Patents, 17(4):371-384.
Berge, S.M., et al., 1977. "Pharmaceutical Salts," Journal of Pharmaceutical Science, 66(1):1-19.
Bettayeb, K., et al., 2007. "Meriolins, a New Class of Cell Death-Inducing Kinase Inhibitors with Enhanced Selectivity for Cyclin—Dependent Kinases," Cancer Research, 67(17): 8325-8334.
Bewick, A., et al., 1976. "The Electrochemical Difunctionalisation of Saturated Hydrocarbons," Tetrahedron Letters, 8:631-634.
Bewick, A., et al., 1977. "Electrochemical Difunctionalisation of Adamantane and Further Oxidation of Substituted Adamantanes," Journal of the Chemical Society, 16:1831-1834.
Bontempi, B., et al., 1996. "Differential Temporal Evolution of Post-Training Changes in Regional Brain Glucose Metabolism Induced by Repeated Spatial Discrimination Training in Mice: Visualization of the Memory Consolidation Process?," European Journal of Neuroscience, 8:2348-2360.
Breysse, N., et al., 2002. "Chronic But Not Acute Treatment with a Metabotropic Glutamate 5 Receptor Antagonist Reverses the Akinetic Deficits in a Rat Model of Parkinsonism," Journal of Neuroscience, 22(13):5669-5678.
Buccafusco, J., 2009. "Emerging Cognitive Enhancing Drugs, Expert Opinion." Emerg. Drugs, 14(4):577-589.
Chen, L., et al., 2009. "Chronic, Systemic Treatment with a Metabotropic Glutamate Receptor 5 Antagonist in 6-Hydroxydopamine Partially Lesioned Rats Reverses Abnormal Firing of Dopaminergic Neurons," Brain Research, 1286:192-200.
Chemcats Abstract Services, XP002552840, 2010.
Cheng, Y., et al.,1973. "Relationship Between the Inhibition Constant (KI) and the Concentration of Inhibitor which Causes 50 Per Cent Inhibition (I50) of an Enzymatic Reaction," Biochemical Pharmacology, 22:3099-3108.
Conn, P.J., et al., 2009. "Allosteric Modulators of GPCRS: A Novel Approach for the Treatment of CNS Disorders," Nature Reviews Drug Discovery, 8(1):41-54.
Cryan, J.F., et al., 2000. "Antidepressant-Like Behavioral Effects Mediated by 5-Hydroxytryptamine 2C Receptors1," Pharmcol. & Exp. Therap., 295(3):1120-1126.

(Continued)

*Primary Examiner* — Kamal Saeed
*Assistant Examiner* — Kristin Bianchi
(74) *Attorney, Agent, or Firm* — Stephen G. Kalinchak; Kitae Lim; Mary Catherine Di Nunzio

(57) ABSTRACT

The present invention provides adamantyl-diamide derivatives of formula (I):

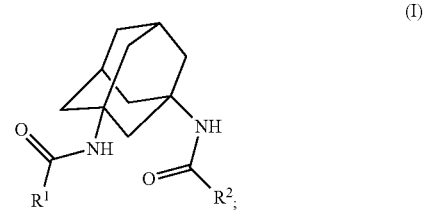

wherein $R^1$ and $R^2$ are as defined herein, or a pharmaceutically acceptable salt thereof; and pharmaceutical compositions and methods using the same.

12 Claims, No Drawings

OTHER PUBLICATIONS

Cryan, J.F., et al., 2005. "Assessing Substrates Underlying the Behavioral Effects of Antidepressants Using the Modified Rat Forced Swimming Test," Neuroscience and Biobehavioral Reviews, 29:547-569.

David, D.J., et al., 2007. "An Animal Model of Altered HPA Axis Responsive to Chronic Antidepressants," SFN meeting in San Diego.

Day, M., 2005. "Ovariectomy-Induced Disruption of Long-Term Synaptic Depression in the Hippocampal CA1 Region in is Vivo is Attenuated with Chronic Estrogen Replacement," Neurobiology of Learning and Memory, 83:13-21.

DePoortere, R., et al., 2003. "SSR181507, A Dopamine D2 Receptor Antagonist and 5-HT1A Receptor Agonist II: Behavioral Profile Predictive of an Atypical Antipsychotic Activity," Neuropsychopharmacology, 28:1889-1902.

Dolen G., et al., 2007. "Correction of Fragile X Syndrome in Mice," Neuron, 56:955-962.

Dulawa, S.C., et al., 2004. "Effects of Chronic Fluoxetine in Animal Models of Anxiety and Depression," Neuropsychopharmcology, 29:1321-1330.

File, S.E., et al., 2003. "A Review of 25 Years of the Social Interaction Test," European Journal of Pharmacology, 463:35-53.

Freed, W.J., et al., 1984. "Effects of Neuroleptics on Phencyclidine (PCP)-Induced Locomotor Stimulation in Mice," Neuropharmacology, 23(2A):175-181.

Fung Y.K. et al., 1986. "Modulation of Apomorphine-Induced Climbing Behavior by Estradiol," Pharmacology Biochemistry and Behavior, 24(1):139-141.

Fung, Y.K., et al., 1987. "Inhibition by Bromoestrogens of the Effects of Estradiol on Apomorphine-Induced Climbing Behavior," Steroids, 49(4-5):287-294.

Gould, T.J., et al., 2002. "MK-801 Disrupts Acquisition of Contextual Fear Conditioning but Enhances Memory Consolidation of Cued Fear Conditioning," Behavioral Pharmacology, 13:287-294.

Hamm, A.O., et al., 2003. "Affective Blindsight: Intact Fear conditioning to a Visual Cue in a Cortically Blind Patient," Brain, 126:267-275.

Holick, K.A., et al., 2008. "Behavioral Effects of Chronic Fluoxetine in BALB/cJ Mice Do Not Require Adult Hippocampal Neurogenesis or the Serotonin 1A Receptor," Neuropsychopharmcology, 33:406-417.

Jaeschke, G., et al., 2008. "mGlu5 Receptor Antagonists and their Therapeutic Potential," Expert Opinion on Therapeutic Patents, 18(2):123-142.

Kim, S.H., et al., 1992. "An Experimental Model for Peripheral Neuropathy Produced by Segmental Spinal Nerve Ligation in the Rat," Pain, 50:355-363.

Korte, S.M., et al., 2003. "A Robust Animal Model of State Anxiety: Fear—Potentiated Behaviour in the Elevated Plus-Maze," European Journal of Pharmacology, 463:163-175.

Lee, E. H., et al., 1992. "Comparative Studies of the Neurotoxicity of MPTP in Rats of Different Ages," Chinese Journal of Physiology, 35(4):317-336.

Liu, H.Y., et al., 2002. "Estrogen Inhibition of EAE Involves Effects on Dendritic Cell Function," Journal of Neuroscience Research, 70:238-248.

May, L.T., 2007. "Allosteric Modulation of G Protein-Coupled Receptors," Annual Review of Pharmacology Toxicology, 47:1-51.

Moore, N. A., et al., 1994. "Effects of Olanzapine and Other Antipyschotic Agents on Responding Maintained by a Conflict Schedule," Behavioural Pharmacology, 5:196-202.

Morris, R., 1981. "Spatial Localization Does Not Require the Presence of Local Cues," Learning and Motivation 12:239-260.

Muir, J., et al., 1995. "Reversal of Visual Attentional Dysfunction Following Lesions of the Cholinergic Basal Forebrain by Physostigmine and Nicotine but not by the 5-HT3 Receptor Antagonist, Ondansetron," Psychopharmacology, 118:82-92.

Njung'e K., et al., 1991. "Evaluation of Marble-Burying Behavior as a Model of Anxiety," Pharmacology Biochemistry and Behavior, 38:63-67.

O'Brien, J.A., et al. 2003. "A Family of Highly Selective Allosteric Modulators of the Metabotropic Glutamate Receptor Subtype 5," Mol. Pharmacology, 64:731-740.

Overstreet, D.H., et al., 2005. "Antidepressant-Like Effects of the Vasopressin V1B Receptor Antagonist SSR149415 in the Flinders Sensitive Line Rat," Pharmacology, Biochemistry, and Behavior, 82:223-227.

Paulekuhn, G.S., et al., 2007. "Trends in Active Pharmaceutical Ingredient Salt Selection Based on Analysis of the Orange Book Database," Journal of Medicinal Chemistry, 50:6665-6672.

Robbins, T.W., et al., 1998. "Neural Systems Underlying Arousal and Attention," Annals NY Academy of Science, 846:222-237.

Rylander, D., et al., 2009. "Pharmacological Modulation of Glutamate Transmission in a Rat Model of L-DOPA-Induced Dyskinesia: Effects on Motor Behavior and Striatel Nuclear Signaling," Journal of Pharmacology and Experimental Therapeutics, 330(1):227-235.

Sams-Dodd, F., 1998. "Effects of Continuous D-Amphetamine and Phencyclidine Administration on Social Behaviour, Stereotyped Behaviour, and Locomotor Activity in Rats," Neuropharmacology, 19(1):18-25.

Santarelli L., et al., 2003. "Requirement of Hippocampal Neurogenesis for Behavioral Effects of Antidepressants," Science, 301:805-809.

Schultz, W., 1982. "Depletion of Dopamine in the Striatum as an Experimental Model of Parkinsonism: Direct Effects and Adaptive Mechanisms," Progress in Neurobiology, 18:121-166.

Seino, H., et al., 1999. "Synthesis of Aliphatic Polyimides Containing Adamantyl Units," Journal of Polymer Science Part A, 37:3584-3590.

Smith, G., et al., 1961. "Some Reactions of Adamantane and Adamantane Derivatives," Journal of Organic Chemistry, 26:2207-2212.

Stetter, H., et al., 1960. "Uber die Bromierung des Adamantans," Chemische Berichte," 93:1366-1371.

Vogel, J., et al., 1971. "A Simple and Reliable Conflict Procedure for Testing Anti-Anxiety Agents," Psychopharmacologia, 21:1-7.

Walker, D., et al., 1997. "Anxiogenic Effects of High Illumination Levels Assessed with the Acoustic Startle Response in Rats," Biological Psychiatry, 42:463-461.

Wheeler-Aceto, H., et al., 1991. "Standardization of the Rat Paw Formalin Test for the Evaluation of Analgesics," Psychopharmacology, 104:35-44.

Yan, Q.J., et al., 2005. "Suppression of Two Major Fragile X Syndrome Mouse Model Phenotypes by the mGluR5 Antagonist MPEP," Neuropharmacology, 49:1053-1066.

International Search Report for PCT Application No. PCT/US2009/050934, mailed, Nov. 16, 2009.

* cited by examiner

ADAMANTYL DIAMIDE DERIVATIVES AND USES OF SAME

CROSS REFERENCE TO RELATED APPLICATIONS

The present application is a U.S. Divisional patent application claiming the benefit of U.S. Nonprovisional patent application Ser. No. 12/504,711 filed Jul. 17, 2009, which claims benefit to Provisional Applications Nos. 61/083,563 and 61/160,804 filed Jul. 25, 2008 and Mar. 17, 2009, respectively, each of which is herein incorporated by reference in its entirety.

FIELD OF THE INVENTION

The present invention provides adamantyl diamide derivatives, as well as pharmaceutical compositions and methods of treatment using same.

BACKGROUND OF THE INVENTION

This invention concerns adamantyl diamide derivatives, which act as allosteric modulators of the metabotropic glutamate receptor 5 (mGlu5 receptors or mGluR5), as well as pharmaceutical compositions and methods of treatment utilizing these compounds.

Glutamate is the major excitatory neurotransmitter in the mammalian central nervous system. One means of modulating glutamate neurotransmission is through metabotropic glutamate receptors (mGluRs); another means being ionotropic receptors. Presently, eight mGluRs have been cloned and classified into three groups based on sequence homology, preferred signal transduction pathway and pharmacology. Group I of mGluRs includes mGluR1 and mGluR5, while Group II comprises mGluR2 and mGluR3 and Group III comprises mGlu4, 6, 7 and 8 receptors.

mGlu receptors have an essential role in normal brain functions, as well as in neurological, psychiatric, and neuromuscular disorders. mGlu5 receptors are located primarily postsynaptically and highly expressed in the limbic brain regions. mGlu5 receptors also are expressed in the thalamus, spinal cord, and vagal nerve systems, as well as peripherally in the skin on nerve endings and C fibers.

Ligands to the mGlu5 receptors have been shown to have promise for peripheral and central nervous system disorders. See e.g., G. Jaeschke et al., "mGlu5 receptor antagonists and their therapeutic potential," *Expert Opin. Ther. Patents,* 2008, 18, 2: 123-142. Yet some proffer that glutamate analogs targeting the orthosteric binding site may be limited by low brain penetration and insufficient selectivity with respect to the different mGluRs subtypes. Synthetic agonists may lead to continuous stimulation of the receptor since they are often designed to be metabolically stable. This continuous stimulation is not necessarily desirable, due to potential receptor desensitization issues. Also, with respect to receptor occupancy, synthetic antagonists may lead to prolonged blockade of receptor function, which may not be compatible with the kinetics of the pathology of a central nervous system disorder.

However, a more selective and controlled "fine-tuning" action on the mGlu5 receptor is feasible through allosteric modulation. See e.g., P. Bach et al., "Metabotropic glutamate receptor 5 modulators and their potential therapeutic applications," *Expert Opin. Ther. Patents,* 2007, 17, 4: 371-381. Allosteric modulation refers to binding by a modulator ligand to a site on a receptor that is different from the orthosteric primary substrate or ligand binding site. This ligand binding process results in conformational changes, which may profoundly influence the function of the protein (e.g., G protein-coupled receptors such as mGluRs, including mGluR5). Novel mGluR5 ligands that allosterically modulate the mGlu5 receptor may improve the therapeutic window of traditional central nervous system agents and/or the treatment of central nervous system disorders. The present invention is directed these, and other important, ends.

SUMMARY OF THE INVENTION

The present invention provides a compound of formula (I):

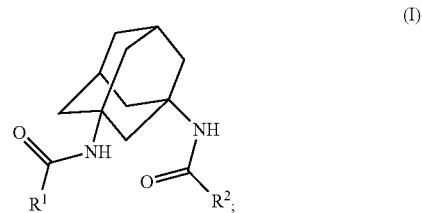

wherein:
$R^1$ and $R^2$ are each independently alkyl, cycloalkyl, keto-cycloalkyl, heterocyclyl, aryl or heteroaryl, which is optionally mono-, di-, or tri-substituted independently with alkyl, alkoxy, halogen, cyano, nitro, trifluoroalkyl, amino, alkylamino, dialkylamino, acyl, aryl, heteroaryl, heterocyclyl, heterocyclyl-$R^3$, —$NHR^3$, —$N(alkyl)R^3$, —$C(O)NHR^3$, —$C(O)N(alkyl)R^3$, —$NHC(O)R^3$, —$N(alkyl)C(O)R^3$, —OH or —$OR^3$, wherein:
$R^3$ is $C_1$-$C_6$alkyl or $C_1$-$C_6$cycloalkyl, which is optionally substituted with halogen, $C_1$-$C_3$alkoxy, OH, —CN, —$NH_2$, —$NH(C_1$-$C_3$alkyl), —$N(C_1$-$C_3$alkyl)$_2$, $C_{1-3}$alkylheterocyclyl, $C_1$-$C_3$alkylcarbamate, —$C(O)NH(C_1$-$C_3$alkyl), —$C(O)N(C_1$-$C_3$alkyl)$_2$, —NHC(O)—$C_1$-$C_3$alkyl, —$N(C_1$-$C_3$alkyl)-C(O)—$C_1$-$C_3$alkyl, OH, or —O—$C_1$-$C_6$alkyl;

with the proviso that the compound of formula (I) is not:
N,N'-(1,3-adamantylene)bis(3-methoxy-benzamide);
N,N'-(1,3-adamantylene)bis(4-ethoxy-benzamide);
N,N'-(1,3-adamantylene)bis(4-methoxy-benzamide);
N,N'-(1,3-adamantylene)bis(3,4,5-trimethoxybenzamide);
N,N'-(1,3-adamantylene)bis(2-iodo-benzamide);
N,N'-(1,3-adamantylene)bis-benzamide;
N,N'-(1,3-adamantylene)bis(3-nitrobenzamide); and
N,N'-(1,3-adamantylene)bis-(3-pyridinecarboxamide); or
a pharmaceutically acceptable salt thereof.

The present invention also provides a pharmaceutical composition comprising at least one compound of the invention or a pharmaceutically acceptable salt thereof, and at least one pharmaceutically acceptable carrier.

The present invention also provides a method of treating a disease or disorder, the method comprises administering a therapeutically effective amount of at least one compound of the present invention or a pharmaceutically acceptable salt thereof to a mammal in need thereof, wherein the disease or disorder is a central nervous system disease or disorder. In some embodiments of the method, a symptom of the disease or disorder is treated.

DETAILED DESCRIPTION OF THE INVENTION

In one aspect, the present invention provides adamantyl diamide derivatives. The present invention comprises a compound of formula (I):

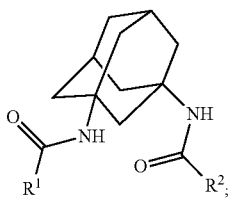

(I)

wherein:
R¹ and R² are each independently alkyl, cycloalkyl, ketocycloalkyl, heterocyclyl, aryl or heteroaryl, which is optionally mono-, di-, or tri-substituted independently with alkyl, alkoxy, halogen, cyano, nitro, trifluoroalkyl, amino, alkylamino, dialkylamino, acyl, aryl, heteroaryl, heterocyclyl, heterocyclyl-R³, —NHR³, —N(alkyl)R³, —C(O)NHR³, —C(O)N(alkyl)R³, —NHC(O)R³, —N(alkyl)C(O)R³, —OH or —OR³, wherein:
R³ is $C_1$-$C_6$alkyl or $C_1$-$C_6$cycloalkyl, which is optionally substituted with halogen, $C_1$-$C_3$alkoxy, OH, —CN, —NH$_2$, —NH($C_1$-$C_3$alkyl), —N($C_1$-$C_3$alkyl)$_2$, $C_1$-$C_3$alkylheterocyclyl, $C_1$-$C_3$alkylcarbamate, —C(O)NH($C_1$-$C_3$alkyl), —C(O)N($C_1$-$C_3$alkyl)$_2$, —NHC(O)—$C_1$-$C_3$alkyl, —N($C_1$-$C_3$alkyl)-C(O)—$C_1$-$C_3$alkyl, OH, or —O—$C_1$-$C_6$alkyl;
with the proviso that the compound of formula (I) is not:
N,N'-(1,3-adamantylene)bis(3-methoxy-benzamide) (i.e., the compound having CAS registry number 899289-36-2);
N,N'-(1,3-adamantylene)bis(4-ethoxy-benzamide) (i.e., the compound having CAS registry number 899289-24-8);
N,N'-(1,3-adamantylene)bis(4-methoxy-benzamide) (i.e., the compound having CAS registry number 899259-96-2);
N,N'-(1,3-adamantylene)bis(3,4,5-trimethoxybenzamide) (i.e., the compound having CAS registry number 173068-46-7);
N,N'-(1,3-adamantylene)bis(2-iodo-benzamide) (i.e., the compound having CAS registry number 899259-92-8);
N,N'-(1,3-adamantylene)bis-benzamide (i.e., the compound having CAS registry number 103307-81-9);
N,N'-(1,3-adamantylene)bis(3-nitrobenzamide) (i.e., the compound having CAS registry number 350024-39-4); and
N,N'-(1,3-adamantylene)bis-(3-pyridinecarboxamide) (i.e., the compound having CAS registry number 371933-95-8); or
a pharmaceutically acceptable salt thereof.

The term "alkyl", employed alone or as part of a group, is defined herein, unless otherwise stated, as either a straight-chain or branched saturated hydrocarbon of 1 to 8 carbon atoms. In some embodiments, the alkyl moiety contains 8, 7, 6, 5, 4, 3, 2 or 1 carbon atoms. Where the term "alkyl" appears herein without a carbon atom range it means a range of $C_1$-$C_8$. Examples of saturated hydrocarbon alkyl moieties include, but are not limited to, chemical groups such as methyl, ethyl, n-propyl, isopropyl, n-butyl, tert-butyl, iso-butyl, sec-butyl, n-pentyl, n-hexyl, and the like.

The term "alkoxy", employed alone or in combination with other terms, is defined herein, unless otherwise stated, as —O-alkyl, where "alkyl" is as previously defined herein. Examples of alkoxy moieties include, but are not limited to, chemical groups such as methoxy, ethoxy, iso-propoxy, sec-butoxy, tert-butoxy, and homologs, isomers, and the like. Alkoxy also refers to —O-alkyl moieties where the alkyl group is substituted by hydroxy, cyano, alkoxy, alkylamino, dialkylamino, alkylamide, dialkylamide, and the like, including without limitation, —O$C_1$-$C_4$alkyl-OH, —O$C_1$-$C_4$alkyl-OCH$_3$, —O$C_1$-$C_4$alkyl-NHCH$_3$, —O$C_1$-$C_4$alkyl-N(CH$_3$)$_2$, —O$C_1$-$C_4$alkyl-CONHCH$_3$, —O$C_1$-$C_4$alkyl-CON(CH$_3$)$_2$, —O$C_1$-$C_4$alkyl-NHCOCH$_3$, and —O$C_1$-$C_4$alkyl-N(CH$_3$)COCH$_3$.

As used herein, the term "cycloalkyl", employed alone or in combination with other terms, is defined herein, unless otherwise stated, as a cyclized alkyl group having from 3 to 8 ring carbon atoms, where "alkyl" is as defined herein. Examples of cycloalkyl moieties include, but are not limited to, chemical groups such as cyclopropyl, cyclobutyl, cyclopentyl, and cyclohexyl.

As used herein, the term "ketocycloalkyl", employed alone or in combination with other terms, is defined herein, unless otherwise stated, as a cycloalkyl having a keto radical attached thereto, where "cycloalkyl" is as defined herein. Examples include cyclopentanone or cyclohexanone.

The terms "halo" or "halogen", employed alone or in combination with other terms, is defined herein, unless otherwise stated, as fluoro, chloro, bromo, or iodo.

The term "aryl", employed alone or in combination with other terms, is defined herein, unless otherwise stated, as an aromatic hydrocarbon of up to 14 carbon atoms, which can be a single ring (monocyclic) or multiple rings (e.g., bicyclic, tricyclic, polycyclic) fused together or linked covalently. Any suitable ring position of the aryl moiety can be covalently linked to the defined chemical structure. Examples of aryl moieties include, but are not limited to, chemical groups such as phenyl, benzyl, 1-naphthyl, 2-naphthyl, and the like. An aryl group can be unsubstituted or substituted as described herein.

The term "heteroaryl" employed alone or in combination with other terms, is defined herein, unless otherwise stated, as a monocyclic or polycyclic (fused together or linked covalently) aromatic hydrocarbon ring comprising one or more heteroatoms independently selected from nitrogen, oxygen, and sulfur. A heteroaryl group comprises up to 14 carbon atoms and 1 to 6 heteroatoms. Examples of heteroaryl groups include, but are not limited to, pyridinyl, pyridazinyl, triazinyl, pyrrolyl, pyrazolyl, imidazolyl, (1,2,3,)- and (1,2,4)-triazolyl, pyrazinyl, pyrimidinyl, tetrazolyl, furyl, thienyl, isoxazolyl, thiazolyl, oxazolyl, 2-quinolinyl, 2-quinazolinyl, 3-phenyl-2-quinolinyl and the like. A heteroaryl group can be unsubstituted or substituted as described herein.

The term "heterocyclyl" employed alone or in combination with other terms, is defined herein, unless otherwise stated, as a univalent group formed by removing a hydrogen atom from any ring atom of a heterocycle.

The term "acyl" employed alone or in combination with other terms, is defined herein, unless otherwise stated, as groups of formula —C(O)-alkyl, where alkyl is a previously described herein; i.e., an alkylcarbonyl, such as formyl, acetyl and the like.

The term "aminoalkyl" employed alone or in combination with other terms, is defined herein, unless otherwise stated, as alkyl-amino, where the term "alkyl" is as previously defined herein and the term "amino" is —NH$_2$, —NH—, or —N<. Non-limiting examples include —CH$_3$NH—, CH$_3$CH$_2$NH—, ($C_1$-$C_3$alkyl)NH—, ($C_1$-$C_3$alkyl)$_2$N—, and the like.

The term "alkylamino" employed alone or in combination with other terms, is defined herein, unless otherwise stated, as amino-alkyl, where the term "alkyl" is as previously defined herein and the term "amino" is —NH$_2$, —NH—, or —N<. Non-limiting examples include —NHCH$_3$, —NHCH$_2$CH$_3$, —NH(C$_1$-C$_3$alkyl), —N(C$_1$-C$_3$alkyl)$_2$, and the like.

In some embodiments of the invention, R$^1$ and R$^2$ are both aryl. In some embodiments, R$^1$ and R$^2$ are both heteroaryl. In some embodiments, R$^1$ is aryl and R$^2$ is heteroaryl. In some embodiments of the invention, at least one aryl is phenyl. In some embodiments, at least one heteroaryl is pyridinyl, pyrimidinyl, pyridazinyl, thiazolyl, pyrazolyl, indazolyl, thiophenyl, furanyl, or benzofuranyl. In some embodiments, both aryls are phenyl. In some embodiments, both heteroaryls are selected from a group consisting of pyridinyl, pyrimidinyl, pyridazinyl, thiazolyl, pyrazolyl, indazolyl, thiophenyl, furanyl, and benzofuranyl.

In some embodiments of the invention, at least one aryl or heteroaryl is substituted as previously described. In some such embodiments, the 1, 2, or 3 substituents are independently selected from the group consisting of methyl, methoxy, dimethylamino-ethoxy, amino, methylamino, dimethylamino, cyano, chloro, fluoro, furanyl and thiophenyl.

In some embodiments, R$^1$ and R$^2$ each are independently selected from a group consisting of phenyl, 3 or 4-methyl-phenyl, 3 or 4-chloro-phenyl, 3 or 4-fluoro-phenyl, 3 or 4-dimethylamino-ethoxy-phenyl, 3 or 4-dimethylamino-phenyl, 3 or 4-cyano-phenyl, 3-(5-methyl-[1,2,4]oxadiazol-3-yl)-phenyl, 1H-indole-5-yl, 1H-indole-6-yl, 1H-benzimidazole-5-yl, pyridyl, 2-pyridyl, 4-pyridyl, 4- or 5-methyl-pyridin-2-yl, 6-methyl-pyridin-2-yl, 6-chloro-pyridin-2-yl, pyrazin-2-yl, thiazol-2-yl, 5-(thiophen-2-yl)-1H-pyrazol-3-yl, 1-methyl-5-(thiophen-2-yl)-1H-pyrazol-3-yl, 5-(furan-2-yl)-1-methyl-1H-pyrazol-3-yl, indazol-3-yl, 2-methyl-2H-indazol-3-yl, benzofuranyl, benzofuran-5-yl.

In some embodiments, the compound of the present invention is a compound disclosed in the Experimental Section below. In some embodiments, the compound is one from Table 1, 2, 3, or 4, below.

In some embodiments of the invention, R$^1$ and R$^2$ are both aryl. In some embodiments, R$^1$ and R$^2$ are both heteroaryl. In some embodiments, R$^1$ is aryl and R$^2$ is heteroaryl. In some embodiments, either R$^1$ or R$^2$ is heteroaryl. In some embodiments, either R$^1$ or R$^2$ is aryl.

In some embodiments of the invention, at least one aryl is phenyl. In some embodiments, at least one heteroaryl is benzofuranyl, benzo[c]isoxazolyl, benzooxazolyl, benzothiazolyl, dihydrothieno[3,4-b][1,4]dioxinyl, furanyl, imidazo[1,2-a]pyridinyl, indazolyl, indolinyl, indolyl, isoquinolinyl, isoxazolyl, naphthyridinyl, oxazolyl, pyrazinyl, pyrazolyl, pyridazinyl, pyridinyl, pyrimidinyl, pyrrolo[3,2-c]pyridine, quinolinyl, quinoxalinyl, thiazolyl, or thiophenyl.

In some embodiments, both aryls are phenyl. In some embodiments, both heteroaryls are selected from a group consisting of at least one heteroaryl is benzofuranyl, benzo[c]isoxazolyl, benzoxazolyl, benzothiazolyl, dihydrothieno[3,4-b][1,4]dioxinyl, furanyl, imidazo[1,2-a]pyridinyl, indazolyl, indolinyl, indolyl, isoquinolinyl, isoxazolyl, naphthyridinyl, oxazolyl, pyrazinyl, pyrazolyl, pyridazinyl, pyridinyl, pyrimidinyl, pyrrolo[3,2-c]pyridinyl, quinolinyl, quinoxalinyl, thiazolyl, or thiophenyl.

In some embodiments, the heteroaryl is pyridinyl, and the pyridinyl is mono-, di-, or tri-substituted as previously defined. In some such embodiments, the mono-, di-, or tri-substitutions are independently heteroaryl, heterocyclyl, heterocyclyl-R$^3$, —NHR$^3$, —N(alkyl)R$^3$, wherein R$^3$ is as previously defined.

In some embodiments of the invention, R$^1$ is aryl or heteroaryl and R$^2$ is cycloalkyl, ketocycloalkyl or heterocyclyl. In some embodiments, either R$^1$ or R$^2$ is cycloalkyl. In some embodiments, at least one cycloalkyl is cyclobutyl, cyclohexyl, cyclopentyl, or cyclopropyl. In some embodiments, the cycloalkyl is further substituted beyond the tri-substitution previously defined, i.e., the cycloalkyl is substituted more than three times as previously described; for example, the cycloalkyl is tetra-substituted with fluorine.

In some embodiments of the invention, at least one cycloalkyl, ketocycloalkyl, heterocyclyl, aryl, or heteroaryl is substituted as previously described. In some such embodiments, the 1, 2, or 3 substituents are independently selected from the group consisting of methyl, methoxy, dimethylamino-ethoxy, amino, methylamino, dimethylamino, cyano, chloro, fluoro, furanyl and thiophenyl.

In some embodiments, the mono-, di-, or tri-substituents are independently selected from the group consisting of amino, chloro, cyano, dimethylamino, dimethylamino-ethoxy, methyl, methylamino, methoxy, fluoro, —C(O)NHCH$_3$, furanyl, pyrrolidinyl, thiophenyl and trifluoromethyl.

In some embodiments, the compound of the present invention is a compound disclosed in the Experimental Section below. In some embodiments, the compound is one from Table 1, Table 2, Table 3 or Table 4, below.

Another aspect of the present invention is a composition that comprises a pharmaceutically effective amount of a compound according to the present invention, and a pharmaceutically acceptable carrier or excipient.

A composition of the present invention may be adapted to any mode of administration, such as orally (including sublingually), via implants, parentally (including intravenous, intraperitoneal, intraarticularly and subcutaneous injections), rectally, intranasally, topically, ocularly (via eye drops), vaginally, and transdermally.

A compound of the present invention can be used either as a free base or in the form of a salt derived from pharmaceutically acceptable acids or bases. The salt includes without limitation the following: salts with inorganic acids, e.g., hydrochloric acid, hydrobromic acid, sulfuric acid, nitric acid, and phosphoric acid, and organic acids e.g., acetic acid, oxalic acid, citric acid, tartaric acid, succinic acid, maleic acid, benzoic acid, benzene sulfonic acid, fumaric acid, malic acid, methane sulfonic acid, pamoic acid, and para-toluene sulfonic acid. Other salts include salts with alkali metals or alkaline earth metals, e.g., sodium, potassium, calcium and magnesium, or with organic bases, including quaternary ammonium salts. Further non-limiting examples of pharmaceutically acceptable inorganic and organic acid addition salts include those listed in [S. M. Berge et al., *J. Pharm. Sci.* 1977, 66, 1: 2, and G. S. Paulekuhn, et al., *J. Med. Chem.* 2007, 50, 26: 6665-6672].

A compound of the present invention can also be used in the form of an ester, carbamate and other conventional prodrug form, which generally will be a functional derivative of the compound that is readily converted to the active moiety in vivo. Also included are metabolites of a compound of the present invention defined as active species produced upon introduction of the compound into a biological system.

When a compound of the present invention is employed as described above, it may be combined with one or more pharmaceutically acceptable excipients or carriers, e.g., solvents, diluents and the like. Such pharmaceutical preparations may be administered orally in such forms as tablets, capsules (including, e.g., time release and sustained release formulations), pills, lozenges, aerosols, dispersible powders, granules, solutions, suspensions (containing, e.g., a suspending agent, at, e.g., from about 0.05 to about 5% of suspending agent), syrups (containing, e.g., sugar or a sugar substitute such as aspartame, at, e.g., about 10 to about 50% sugar or sugar substitute), elixirs and the like, or parenterally in the form of sterile injectable solutions, suspensions or emulsions containing, e.g., from about 0.05 to about 5% suspending agent in an isotonic medium. Such preparations may contain, e.g., from about 25 to about 90% of the active ingredient in combination with the carrier, more customarily from about 5% and about 60% by weight. The effective dosage of an active ingredient (e.g., a compound or salt of the present invention and a prodrug or metabolite thereof) employed may vary depending on the particular compound, salt, prodrug or metabolite used, the mode of administration, age, weight, sex and medical condition of the patient, and the severity of the disease, disorder, condition, and/or system being treated. The selection of the appropriate administration and dosage form for an individual mammal will be apparent to those skilled in the art. Such determinations are routine to a physician, veterinarian or clinician of ordinary skill in the art (see e.g., *Harrison's Principles of Internal Medicine*, Anthony Fauci et al. (eds.) 14$^{th}$ ed. New York: McGraw Hill (1998)). Further, the dosage regimen may be adjusted to provide the optimal therapeutic response. For example, several divided doses may be administered daily or the dose may be proportionally reduced as indicated by the needs of the therapeutic situation.

Solid carriers, e.g., starch, lactose, dicalcium phosphate, microcrystalline cellulose, sucrose and kaolin, liquid carriers, e.g., sterile water, polyethylene glycols, glycerol, non-ionic surfactants and edible oils such as corn, peanut and sesame oils, may be employed as are appropriate to the nature of the active ingredient and the particular form of administration desired. Adjuvants customarily employed in the preparation of pharmaceutical compositions may be advantageously included. Non-limiting examples of adjuvants include flavoring agents, coloring agents, preserving agents, and antioxidants, such as vitamin E, ascorbic acid, BHT and BHA.

An active compound also may be administered parenterally or intraperitoneally. Solutions or suspensions of the active compound as a free base, neutral compound or pharmacologically acceptable salt can be prepared in water suitably mixed with a surfactant such as hydroxypropylcellulose. Dispersions also can be prepared in glycerol, liquid polyethylene glycols and mixtures thereof in oils. These preparations may contain a preservative to prevent the growth of microorganisms under ordinary conditions of storage and use.

The pharmaceutical forms suitable for injectable or infusing use include sterile aqueous solutions, suspensions or dispersions, and sterile powders for the extemporaneous preparation of sterile injectable or infusing solutions, suspension or dispersions. In all cases, the form must be sterile and must be fluid to the extent that easy injectability and infusing exists. It must be stable under conditions of manufacture and storage and must be preserved against the contaminating action of microorganisms. The carrier can be a solvent or dispersion medium containing, for example, water, ethanol, and polyol (e.g., glycerol, propylene glycol, and liquid polyethylene glycol), suitable mixtures thereof, and vegetable oil.

Furthermore, active compounds of the present invention can be administered intranasally or transdermally using vehicles suitable for intranasal or transdermal delivery known to those ordinarily skilled in the art. Transdermal administration includes all administrations across the surface of the body and the inner linings of bodily passages including epithelial and mucosal tissues, using carrier systems such as lotions, creams, foams, pastes, patches, suspensions, solutions, and suppositories (rectal and vaginal). Creams and ointments may be viscous liquid or semisolid emulsions of either the oil-in-water or water-in-oil type. Pastes comprised of absorptive powders dispersed in petroleum or hydrophilic petroleum containing the active ingredient also may be suitable. A variety of occlusive devices may be used to release the active ingredient into the blood stream such as a semi-permeable membrane covering a reservoir containing the active ingredient with or without a carrier, or a matrix containing the active ingredient. Other occlusive devices are known in the literature. When using a transdermal delivery system, the dosage administration will be continuous rather than a single or divided daily dose.

A compound of the present invention can also be administered in the form of a liposome delivery system where the liposomal lipid bilayer is formed from a variety of phospholipids. A compound of the present invention also may be delivered by the use of a carrier such as monoclonal antibodies to which the compound is coupled. Other carriers to which a compound of the present invention also may be coupled are a soluble polymer or a biodegradable polymer useful in achieving controlled release of an active ingredient.

It is understood by those practicing the art that some of the compounds of the present invention may contain one or more asymmetric centers, and thus may give rise to enantiomers and diastereomers. The present invention includes all stereoisomers including individual diastereomers and resolved, enantiomerically pure stereoisomers, as well as racemates, and all other variations of stereoisomers, and mixtures and pharmaceutically acceptable salts thereof, which possess the indicated activity. Optical isomers may be obtained in pure form by customary procedures known to those skilled in the art, and include, but are not limited to, chiral chromatographic separations, diastereomeric salt formation, kinetic resolution, and asymmetric synthesis. It is also understood that this invention encompasses all possible regioisomers, endo-exo isomers, and mixtures thereof that possess the indicated activity. Such isomers can be obtained in pure form by customary procedures known to those skilled in the art, and include, but are not limited to, column chromatography, thin-layer chromatography, and high-performance liquid chromatography. It is understood by those practicing the art that some of the compounds of the present invention may be chiral due to hindered rotation, and give rise to atropisomers, which can be resolved and obtained in pure form by customary procedures known to those skilled in the art. It is further understood by those practicing the art that some of the compounds of the present invention include structural isomers, including tautomers.

Included also in this invention are all polymorphs and hydrates of the compounds of the present invention.

Another aspect of the present invention is a method for using the compounds of the invention. The invention is to be understood as embracing all simultaneous, sequential or separate use of any combination of the compounds of the invention with any pharmaceutical composition useful in the methods described herein.

In some embodiments, the method includes administering an effective amount of a combination of two or more of the compounds described herein, or salts thereof. It is specifically intended that the phrases "combination of two or more of the compounds described herein, or salts thereof," or "at least one compound as described herein, or a pharmaceutically acceptable salt thereof," or similar language describing specific compounds, includes the administration of such compounds in any proportion and combination of salt, neutral or free base forms; i.e., includes the administration of such compounds each in the base form, each in the neutral form or each in the salt form, or one or more in the base form and one or more in the neutral form, or one or more in the base form and one or more in the salt form, or one or more in the neutral form and one or more in the salt form, in any proportion of the neutral and/or basic compounds and/or salts.

As used herein, the phrase "effective amount" when applied to a compound of the invention, is intended to denote an amount sufficient to cause an intended biological effect. The phrase "therapeutically effective amount" when applied to a compound of the invention is intended to denote an amount of the compound that is sufficient to ameliorate, palliate, stabilize, reverse, slow or delay the progression of a disorder or disease state, or of a symptom of the disorder or disease. In some embodiments, the method of the present invention provides for administration of combinations of compounds. In such instances, the "effective amount" is the amount of the combination sufficient to cause the intended biological effect.

The term "treatment" or "treating" as used herein means curing, ameliorating or reversing the progress of a disease or disorder, or ameliorating or reversing one or more symptoms or side effects of such disease or disorder. "Treatment" or "treating", as used herein, also means to inhibit or block, as in retard, arrest, restrain, impede or obstruct, the progress of a system, condition or state of a disease or disorder. For purposes of this invention, "treatment" or "treating" further means an approach for obtaining beneficial or desired clinical results, where "beneficial or desired clinical results" include, without limitation, alleviation of a symptom, diminishment of the extent of a disorder or disease, stabilized (i.e., not worsening) disease or disorder state, delay or slowing of a disease or disorder state, amelioration or palliation of a disease or disorder state, and remission of a disease or disorder, whether partial or total, detectable or undetectable.

The term "prevent" or "preventing" as used herein means to keep from happening or existing. The term "administering" as used herein refers to either directly administering a compound of the present invention, or administering a prodrug, derivative, or analog of same, that will form an effective amount of the compound within a mammal.

The present invention also provides a method of treating a disease or disorder, the method comprises administering a therapeutically effective amount of at least one compound of the present invention or a pharmaceutically acceptable salt thereof to a mammal in need thereof, wherein the disease or disorder is a central nervous system disease or disorder.

A compound of the present invention can allosterically modulate the mGlu5 receptor. An allosteric modulator that enhances or potentiates the affinity of an orthosteric ligand for the mGluR5 receptor and/or enhances or potentiates an orthosteric agonist's efficacy is an allosteric enhancer (or potentiator) or positive allosteric modulator (PAM). See e.g., May, L. T. *Annu. Rev. Pharmacol. Toxicol.* 2007, 47, 1-51. An allosteric modulator that reduces or diminishes the affinity of an orthosteric ligand for the mGluR5 receptor and/or reduces or diminishes an orthosteric agonist's efficacy is an allosteric antagonist (or inhibitor) or negative allosteric modulator (NAM). Id.

In some embodiments, the mammal of the method of the invention is a human.

In some embodiments of the method of the invention, the central nervous system disease or disorder is a cognitive, neurodegenerative, psychiatric or neurological disease or disorder. In some such embodiments, the cognitive, neurodegenerative, psychiatric or neurological disease or disorder is selected from a group consisting of a mood disorder, an anxiety, a schizophrenia (including schizoaffective disorders), Alzheimer's disease, Parkinson's disease, multiple sclerosis, Huntington's chorea, amyotrophic lateral sclerosis, Creutzfeld-Jakob disease, a trauma-induced neurodegeneration, AIDS-induced encephalopathy, another infection-related encephalopathy (i.e., a non-AIDS-induced encephalopathy), Fragile X syndrome, an autism spectrum disorder, and a combination thereof.

As used herein, the phrase "mood disorder" refers to any of several psychological disorders characterized by abnormalities of emotional state, such as, without limitation, bipolar disorders, depressive disorders, cyclothymic disorders, dysthymic disorders, mood disorders due to a general medical condition, mood disorders not otherwise specified and substance-induced mood disorders; and as characterized by the *Diagnostic and Statistical Manual of Mental Disorders*, Fourth Edition (DSM-IV) (American Psychiatric Association: Arlington, Va., 1994).

As used herein, the phrase "autism spectrum disorder" (ASD) refers to a disorder that causes severe and pervasive impairment in thinking, feeling, language, and the ability to relate to others, which is often first diagnosed in early childhood and range from a severe form, called autistic disorder ("classic" autism), through pervasive development disorder not otherwise specified (PDD-NOS), to a much milder form, Asperger syndrome. The phrase, as used herein, also includes Rett syndrome and childhood disintegrative disorder, and as used herein, is synonymous with the phrase, "pervasive developmental disorders" (PDDs).

In some such embodiments, the mood disorder is a depression (i.e., a depressive disorder). In some such embodiments, the depression is selected from the group consisting of atypical depression, bipolar depression, unipolar depression, major depression, endogenous depression (i.e., acute depression with no obvious cause), involutional depression (i.e., depression that occurs in mid-life or the elderly), reactive depression (i.e., depression caused by an obvious traumatic life episode), postpartum depression, primary depression (i.e., depression that has no obvious physical or psychological cause such as a medical illness or disorder), psychotic depression, and secondary depression (i.e., depression that seems to be caused by some other underlying condition such another medical illness or disorder).

In some such embodiments, the anxiety disease or disorder is selected from a group comprising generalized anxiety disorder, panic anxiety, obsessive compulsive disorder, social phobia, performance anxiety, post-traumatic stress disorder, acute stress reaction, an adjustment disorder, a hypochondriacal disorder, separation anxiety disorder, agoraphobia, a specific phobia, anxiety disorder due to general medical condition, substance-induced anxiety disorder, alcohol withdrawal-induced anxiety, and a combination thereof.

In some embodiments, the central nervous system disease or disorder of the method of the invention is a seizure disease or disorder. In some embodiments, the seizure disease or disorder is selected from the group consisting of a convulsion, epilepsy, status epilepticus, and a combination thereof.

In some embodiments, the central nervous system disease or disorder of the method of the invention is a pain disease or disorder selected from the group consisting of inflammatory pain, neuropathic pain and migraine pain. In some embodiments, the neuropathic pain or migraine pain disease or disorder is selected from the group consisting of allodynia, hyperalgesic pain, phantom pain, neuropathic pain related to diabetic neuropathy, neuropathic pain related to migraine, and a combination thereof.

In some embodiments, the central nervous system disease or disorder of the method of the invention is a neuronal hyperexcitation state disease or disorder. In some embodiments, the neuronal hyperexcitation state disease or disorder is a neuronal hyperexcitation state in medicament withdrawal, a neuronal hyperexcitation state in intoxication, or a combination thereof.

In some embodiments of the method of the invention, at least one symptom of the cognitive neurodegenerative, psychiatric or neurological disease or disorder is treated.

In some embodiments, the cognitive, neurodegenerative, psychiatric or neurological disease or disorder is a depression. In some such embodiments, the at least one symptom of the depression is depressed feeling, depressed mood, loss of interest or pleasure in some or all activities, changes in appetite, changes in weight, changes in sleep patterns, lack of energy, fatigue, low self esteem, diminished capacity for thinking, concentration, or decisiveness, feelings of hopelessness or worthlessness, psychomotor agitation or retardation, self-reproach, inappropriate guilt, frequent thoughts of death or suicide, plans or attempts to commit suicide, or a combination thereof.

In some embodiments, the cognitive, neurodegenerative, psychiatric or neurological disease or disorder is an anxiety. In some such embodiments, the at least one symptom of anxiety is apprehension, fear, trembling, muscle aches, insomnia, abdominal upsets, dizziness, irritability, persistent, recurring thoughts, compulsions, heart palpitations, chest pain, chest discomfort, sweating, tingling sensations, feeling of choking, fear of losing control, flashbacks, nightmares, intrusive thoughts, intrusive recollections, avoidance behaviors, emotional numbing, an inability to sleep, anxious feelings, overactive startle response, hypervigilance, outbursts of anger, faintness, blushing, profuse sweating, or a combination thereof.

In some embodiments, the cognitive, neurodegenerative, psychiatric or neurological disease or disorder is schizophrenia. In some such embodiments, the at least one symptom of schizophrenia is a positive symptom selected from the group consisting of hallucination, delusion, paranoia, and a combination thereof. In some such embodiments, the symptom of schizophrenia is a negative symptom selected from the group consisting of social withdrawal, flat affect, anhedonia, decreased motivation, and a combination thereof. In some such embodiments, the symptom of schizophrenia is a cognitive symptom selected from the group consisting of severe deficit in attention, severe deficit in object naming, severe deficit in working memory, severe deficit in long-term memory storage, severe deficit in executive functioning, a slowing of information processing, a slowing of neural activity, long term depression, and a combination thereof.

In some embodiments of the method of the invention, the cognitive, neurodegenerative, psychiatric or neurological disease or disorder is Parkinson's disease. In some such embodiments, the at least one symptom of Parkinson's disease is levodopa-induced dyskinesia, poor balance, Parkinsonian gait, bradykinesia, rigidity, tremor, change in speech, loss of facial expression, micrographia, difficulty swallowing, drooling, pain, dementia, confusion, a sleep disturbance, constipation, a skin problem, depression, fear, anxiety, difficulty with memory, slowed thinking, sexual dysfunction, an urinary problem, fatigue, aching, loss of energy, or a combination thereof.

In some embodiments, the cognitive, neurodegenerative, psychiatric or neurological disease or disorder is Alzheimer's disease. In some such embodiments, the at least one symptom of Alzheimer's disease is impairment in memory, impairment in attention, impairment in judgment, impairment in decision-making, impairment in orientation to physical surroundings, language impairment, impairment in speed-dependent activities, impairment in abstract reasoning, impairment in visuospatial abilities, impairment in executive functioning, impairment in behavioral disturbances, disinterest and passivity, apathy, inappropriate dressing, poor self care, agitation, violent outburst, aggression, depression, anxiety, hallucination, delusion, change in personality, change in mood, dementia, or a combination thereof.

In some embodiments, the cognitive, neurodegenerative, psychiatric or neurological disease or disorder is multiple sclerosis. In some such embodiments, the at least one symptom of multiple sclerosis is optic neuritis blurred vision, eye pain, loss of color vision, blindness, diplopia double vision, nystagmus jerky eye movements, ocular dysmetria, constant under- or overshooting eye movements, internuclear ophthalmoplegia, nystagmus, diplopia, movement and sound phosphenes, diplopia, afferent pupillary defect, motor paresis, monoparesis, paraparesis, hemiparesis, quadraparesis plegia, paraplegia, hemiplegia, tetraplegia, quadraplegia, spasticity, dysarthria, muscle atrophy, spasms, cramps, hypotonia, clonus, myoclonus, myokymia, restless leg syndrome, footdrop dysfunctional reflexes (MRSs, Babinski's, Hoffman's, Chaddock's), paraesthesia, anaesthesia, neuralgia, neuropathic pain, neurogenic pain, l'hermitte's, proprioceptive dysfunction, trigeminal neuralgia, ataxia, intention tremor, dysmetria, vestibular ataxia, vertigo, speech ataxia, dystonia, dysdiadochokinesia, frequent micturation, bladder spasticity, flaccid bladder, detrusor-sphincter dyssynergia, erectile dysfunction, anorgasmy, retrograde ejaculation, frigidity, constipation, fecal urgency, depression, cognitive dysfunction, dementia, mood swings, emotional lability, euphoria, bipolar syndrome, anxiety, aphasia, dysphasia, fatigue, uhthoffs symptom, gastroesophageal reflux, a sleeping disorder, or a combination thereof.

The present invention further provides a method of treating gastroesophageal reflux, the method comprises administering a therapeutically effective amount of at least one compound of claim 1 or a pharmaceutically acceptable salt thereof to a mammal in need thereof.

The present invention further provides a method of treating alcohol dependence, the method comprises administering a therapeutically effective amount of at least one compound of claim 1 or a pharmaceutically acceptable salt thereof to a mammal in need thereof.

In some embodiments, the compound of the present invention is used in the preparation of a medicament for treatment of a central nervous system disease or disorder. In some embodiments, the central nervous disease or disorder is as previously disclosed herein.

Another aspect of the present invention is a process for producing the compounds of the present invention.

Preparation of the Compounds of the Present Invention

The compounds of the present invention may be prepared, without limitation, according to one of the general methods outlined below. For example, Schemes 1-11 that follow are intended as an illustration of some embodiments of the invention and no limitation of the present invention is implied because of them.

The following defines acronyms as used herein unless specified otherwise in a particular instance.

BOP=benzotriazole-1-yl-oxy-tris-(dimethylamino)-phosphonium hexafluorophosphate, CAS No. 56602-33-6
DCM=dichloromethane or methylene chloride
DIEA=N,N-diisopropylethylamine, CAS No. 7087-68-5
DMA=N,N-dimethylacetamide, CAS No. 127-19-5
DMC=dimethylimidazolinium chloride
DMF=N,N-dimethylformamide, CAS No. 68-12-2
DPPA=Diphenylphosphoryl azide, CAS No. 26386-88-9

EDCI=N-Ethyl-N'-(3-dimethylaminopropyl)carbodiimide hydrochloride, CAS No. 93128-40-6
HBTU=2-(1H-Benzotriazole-1-yl)-1,1,3,3-Tetramethyluronium hexafluorophosphate, CAS No. 94790-37-1
NMP=N-Methyl-Pyrrolidone, CAS No. 872-50-4
PyBOP=benzotriazol-1-yl-oxytripyrrolidinophosphonium hexafluorophosphate, CAS No. 128625-52-5
RT or rt=room temperature
TBTU=O-(Benzotriazol-1-yl)-N,N,N',N'-tetramethyluronium tetrafluoroborate, CAS No. 125700-67-6
TEA=triethanolamine, CAS No. 102-71-6
THF=tetrahydrofuran, CAS No. 109-99-9

Symmetrical amides of the formula (I) ($R^1=R^2$) can be prepared via the process outlined in Scheme 1 using customary amidation procedures from commercially available compound 1, adamantane-1,3-diamine, where $R^1$ is equal to $R^2$, and $R^1$ and $R^2$ are as previously defined herein.

Scheme 1

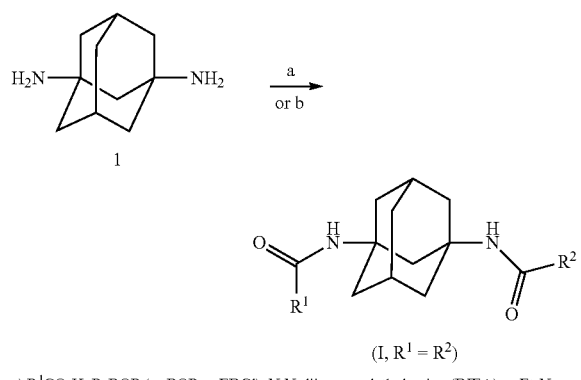

a) $R^1CO_2H$, PyBOP (or BOP or EDCl), N,N-diisopropylethylamine (DIEA) or $Et_3N$, $CH_2Cl_2$ (or THF or DMF)
b) $R^1COCl$, DIEA or $Et_3N$, $CH_2Cl_2$ Unsymmetrical amides of formula (I) ($R^1 \ne R^2$) also can be prepared via the processes outlined in Schemes 2 and 3, where $R^1$ and $R^2$ are as previously defined herein.

Scheme 2

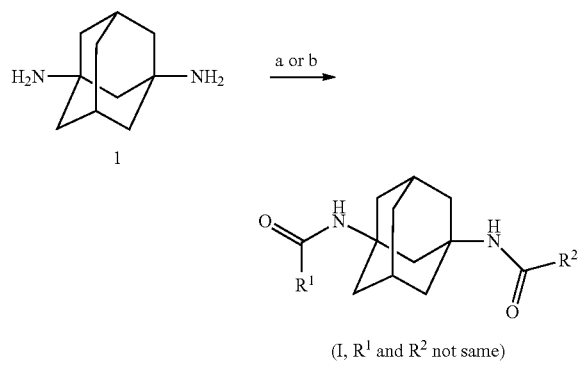

a) 1.1 eq. $R^1CO_2H$, 1.1 eq. $R^2CO_2H$, DIEA, PyBOP (or BOP, DMC, EDCl), $CH_2Cl_2$
b) 1.1 eq. $R^1COCl$, 1.1 eq. $R^2COCl$, DIEA, $CH_2Cl_2$

Amidation of compound 1 with a mixture of $R^1COCl$ and $R^2COCl$, or a mixture of $R^1CO_2H$ and $R^2CO_2H$ using customary amidation procedures affords unsymmetrical amides of formula (I).

Scheme 3

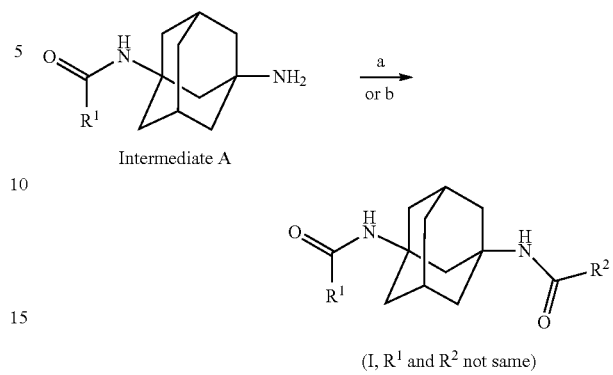

a) $R^2CO_2H$, PyBOP (or BOP or DMC or EDCl or HBTU etc.), DIEA or TEA, $CH_2Cl_2$ (or THF or DMF or $CH_3CN$ etc);
b) $R^2COCl$, DIEA or TEA, $CH_2Cl_2$; or $R^2COCl$, aq. NaOH, THF/$CH_2Cl_2$ Amidation of Intermediate A with $R^2CO_2H$ or $R^2COCl$ using customary amidation procedures affords unsymmetrical amides of formula (I).

Intermediate A can be prepared via the processes outlined in Schemes 4-6.

Scheme 4

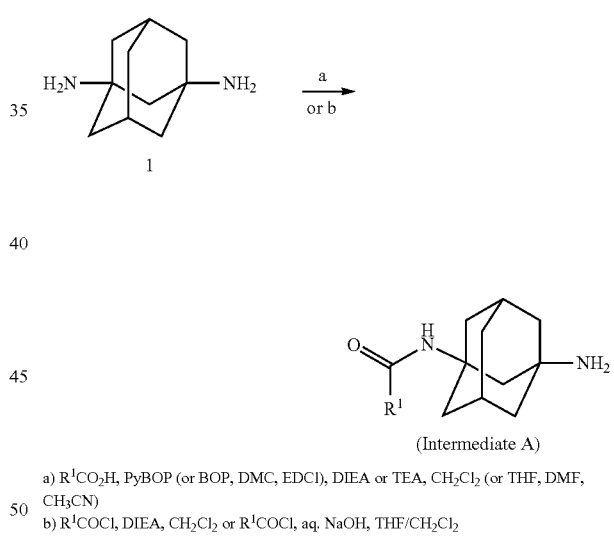

a) $R^1CO_2H$, PyBOP (or BOP, DMC, EDCl), DIEA or TEA, $CH_2Cl_2$ (or THF, DMF, $CH_3CN$)
b) $R^1COCl$, DIEA, $CH_2Cl_2$ or $R^1COCl$, aq. NaOH, THF/$CH_2Cl_2$

Amidation of compound 1 with $R^1CO_2H$ or $R^1COCl$ using customary amidation procedures yields Intermediate A. The yield of this route is low due to the formation of bis-amides.

Scheme 5

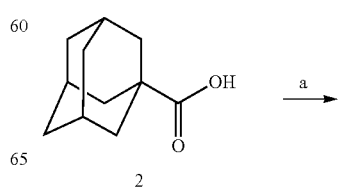

15
-continued

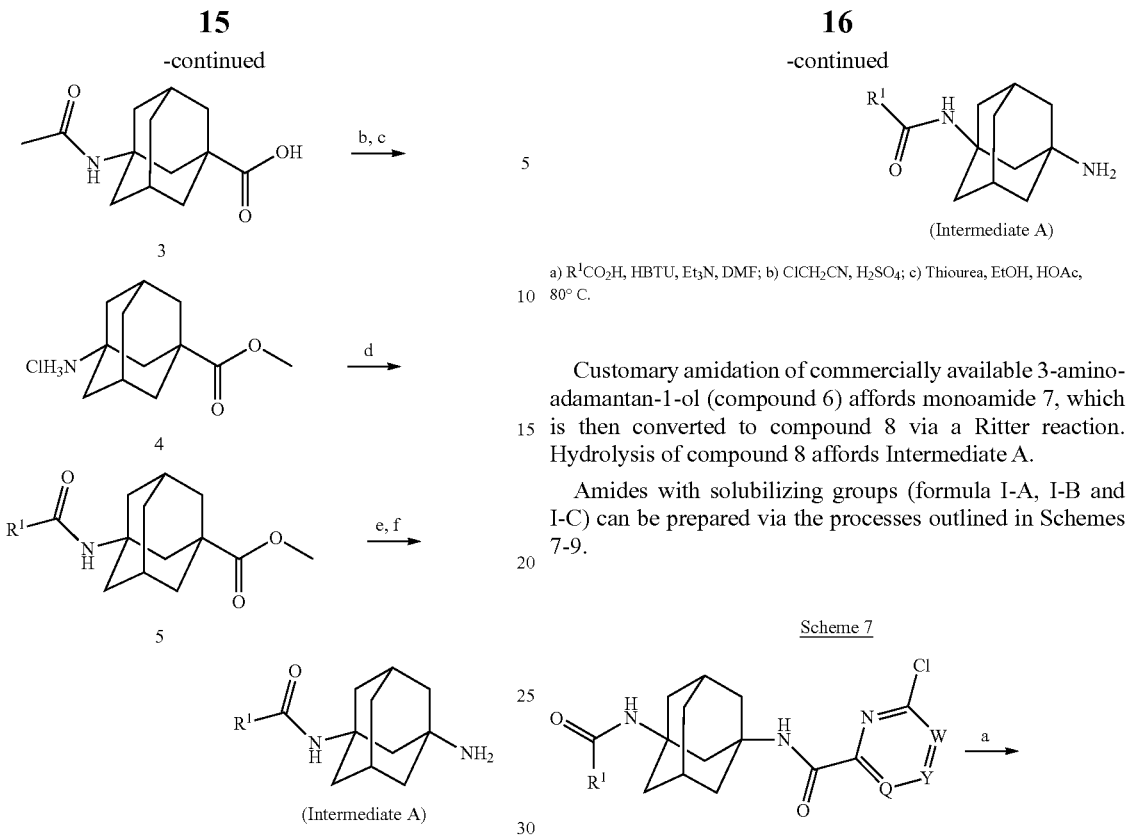

a) H₂SO₄, HNO₃, MeCN; b) HCl, H₂O; c) SOCl₂, MeOH; d) R¹COCl, NEt₃, DCM; or R¹CO₂H, PyBOP, NEt₃, DCM;
e) LiOH, H₂O, THF; f) DPPA, NEt₃, Toluene then HCl, H₂O Commercially available 1-adamantanecarboxylic acid (compound 2) can be converted to acetamide 3 via a Ritter reaction. Hydrolysis of compound 3 under acidic conditions affords the corresponding amine salt, which is then converted to methyl ester 4. Customary amidation of compound 4 affords compound 5. Hydrolysis of ester 5 followed by a standard Curtius rearrangement yields Intermediate A.

Scheme 6

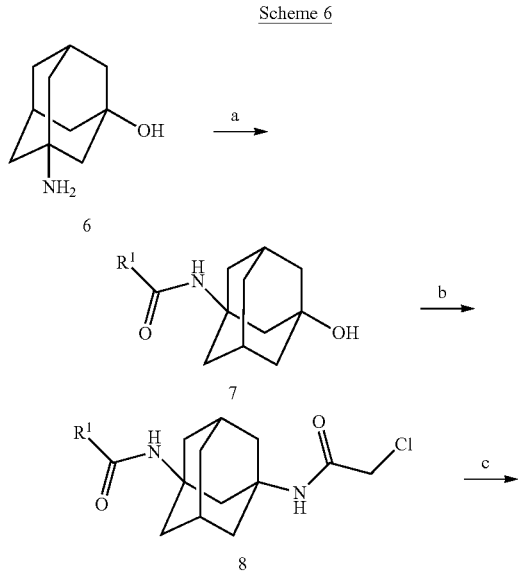

16
-continued

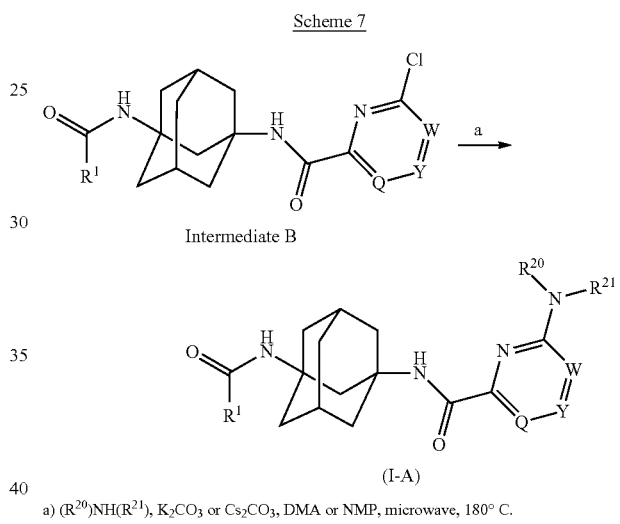

a) R¹CO₂H, HBTU, Et₃N, DMF; b) ClCH₂CN, H₂SO₄; c) Thiourea, EtOH, HOAc, 80° C.

Customary amidation of commercially available 3-aminoadamantan-1-ol (compound 6) affords monoamide 7, which is then converted to compound 8 via a Ritter reaction. Hydrolysis of compound 8 affords Intermediate A.

Amides with solubilizing groups (formula I-A, I-B and I-C) can be prepared via the processes outlined in Schemes 7-9.

Scheme 7 a) (R²⁰)NH(R²¹), K₂CO₃ or Cs₂CO₃, DMA or NMP, microwave, 180° C.

Displacement of chloride of Intermediate B with amines (R²⁰)NH(R²¹) under basic conditions with microwave irradiation yields compounds of formula (I-A), where R²⁰ and R²¹ are alkyl or linked together to form a heterocycle that is optionally substituted by hydroxyl, alkoxy, amine, alkylamine, dialkylamine, —C(O)NH-alkyl, —C(O)N(dialkyl), —NHC(O)-alkyl, —N(alkyl)-C(O)-alkyl; or one of R²⁰ and R²¹ is H and the other is alkyl, cycloalkyl or heterocycle that is optionally substituted by hydroxyl, cyano, alkoxy, amine, alkylamine, dialkylamine, —C(O)—NH₂, —C(O)NH-alkyl, —C(O)N(dialkyl), —NHC(O)-alkyl, —N(alkyl)-C(O)-alkyl; Q, Y and W are CR²³, where R²³ is H, alkyl or cycloalkyl; or one of Q, Y and W is nitrogen.

Scheme 8

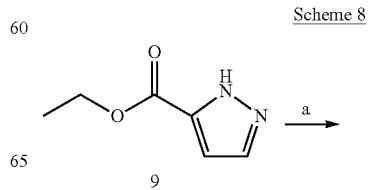

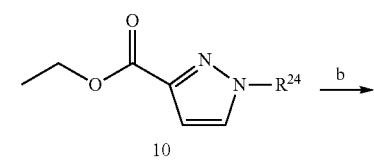

10

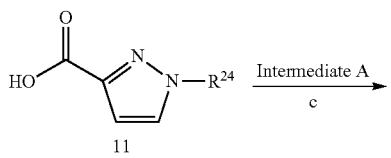

11

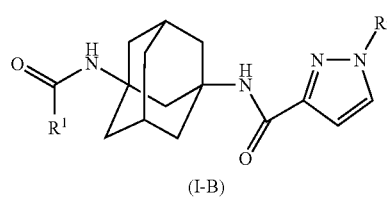

(I-B)

a) $R^{24}Br$ or $R^{24}OMs$ or $R^{24}OTs$, base, DMF; b) aq. NaOH, EtOH; c) Et$_3$N, PyBOP, DCM Alkylation of commercially available compound 9 with $R^{24}Br$, $R^{24}OMs$ or $R^{24}OTs$ under basic conditions such as $K_2CO_3$ or $Cs_2CO_3$ in DMF affords compound 10. $R^{24}OMs$ or $R^{24}OTs$ could be easily made from corresponding $R^{24}OH$ and MeSO$_2$Cl or 4-methylbenzenesulfonyl chloride. Saponification of ester 10 gives carboxylic acid 11. Amidation of compound 11 with Intermediate A using customary procedures could yield compounds of formula (I-B), where $R^{24}$ is alkyl, cycloalkyl or heterocycle that is optionally substituted by hydroxyl, alkoxy, amine, alkylamine, dialkylamine, —C(O)NH-alkyl, —C(O)N(dialkyl), —NHC(O)-alkyl, —N(alkyl)-C(O)-alkyl.

Scheme 9

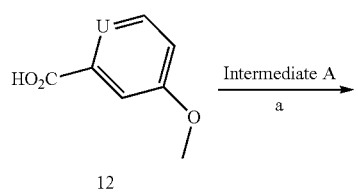

12

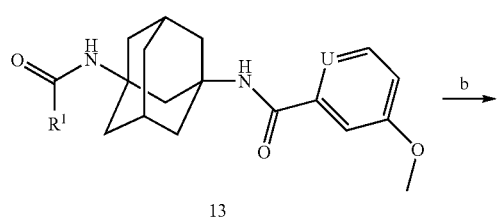

13

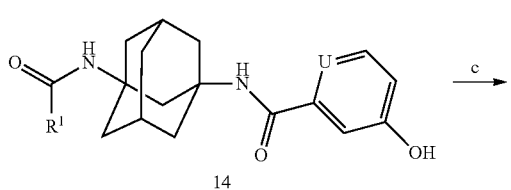

14

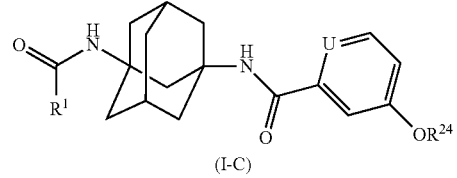

(I-C)

a) PyBOP, Et$_3$N, DCM; b) BBr$_3$, DCM;
c) $R^{24}$OH, Mitsunobu reaction; or $R^{24}$Br ($R^{24}$OMs or $R^{24}$OTs), base, DMF (or THF), 60-100° C.

Customary amidation of commercially available carboxylic acid 12 with Intermediate A affords compound 13, which upon demethylation gives compound 14. Mitsunobu reaction of compound 14 with $R^{24}$OH, or alkylation of compound 14 with $R^{24}$Br, $R^{24}$OMs or $R^{24}$OTs under basic conditions, such as $K_2CO_3$ or $Cs_2CO_3$ in DMF, THF or CH$_3$CN, yields compounds of formula of (I-C), where U is CH or N, and $R^{24}$ is as previously defined herein.

Intermediate B can be made via the process outlined in Scheme 10.

Scheme 10

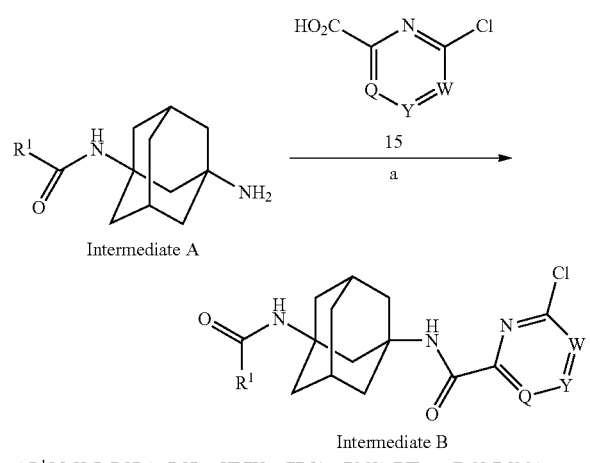

a) $R^1CO_2H$, PyBOP (or BOP or HBTU or EDCl or DMC), DIEA or Et$_3$N, DCM (or DMF or CH$_3$CN)

Customary amidation of Intermediate A with carboxylic acid 15 affords Intermediate B.

Non-commercially available carboxylic acids can be made via the process outlined in Scheme 11.

Scheme 11 heteroaryl-X $\xrightarrow{a}$ heteroaryl-CN $\xrightarrow{b}$ heteroaryl-CO$_2$H 16   17   (Intermediate C)

a) Zn(CN)$_2$, Ph$_2$-pentedienone Pd and (Ph$_2$P)$_2$-ferrocene, DMF, 100° C.
b) HCl, water, reflux; or 1) NaOH, water, 90° C.; 2) HCl and water Displacement of halogen X (X=F, Cl, Br or I) of compound 16 with cyano using customary procedures, such as Zn(CN)$_2$, and catalyst Ph$_2$-pentedienone Pd with ligand (Ph$_2$P)-2-ferrocene in DMF at 100° C. to afford compound 17, which upon hydrolysis under acidic or basic conditions yields Intermediate C.

EXPERIMENTAL SECTION

1. General Methods

Unless specifically stated otherwise, the experimental procedures were performed under the following conditions. All operations were carried out at room temperature (about 18° C. to about 25° C.) under nitrogen atmosphere. Evaporation of solvent was carried out using a rotary evaporator under reduced pressure or in a high performance solvent evaporation system HT-4X (Genevac Inc., Gardiner, N.Y., USA). The course of the reaction was followed by thin layer chromatography (TLC) or liquid chromatography-mass spectrometry (LC-MS), and reaction times are given for illustration only. Silica gel chromatography was carried out on a CombiFlash® system (Teledyne Isco, Inc., Lincoln, Nebr., USA) with pre-packed silica gel cartridge or performed on Merck silica gel 60 (230-400 mesh). The structure and purity of all final products was assured by at least one of the following analytical methods: nuclear magnetic resonance (NMR) and LC-MS. NMR spectra was recorded on a Bruker Avance™ 300 spectrometer (Bruker BioSpin Corp., Billerica, Mass., USA) or a Varian UNITY INOVA® 400 (Varian, Inc., Palo Alto, Calif., USA) using the indicated solvent. Chemical shift ($\delta$) is given in parts per million (ppm) relative to tetramethylsilane (TMS) as an internal standard. Coupling constants (J) are expressed in hertz (Hz), and conventional abbreviations used for signal shape are: s=singlet; d=doublet; t=triplet; m=multiplet; br=broad; etc. Unless stated otherwise, mass spectra were obtained using electrospray ionization (ESMS) via either a Micromass® Platform II system or a Quattro Micro™ system (both from Waters Corp., Milford, Mass., USA) and $(M+H)^+$ is reported.

2. Preparation of Intermediates of the Invention

Unless specified otherwise, the reagents used in the preparation of compounds, including intermediates, of the present invention were purchased from Sigma-Aldrich Corporation (St. Louis, Mo., USA).

Intermediate 1: 6-Methyl-pyridine-2-carboxylic acid (3-amino-adamantan-1-yl)-amide

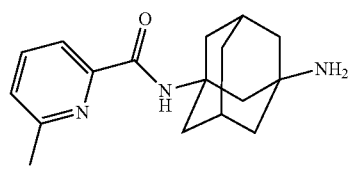

Intermediate 1 was prepared via the process of Scheme 4, supra, as follows:

To a flask containing 6-methyl-pyridine-2-carboxylic acid and (3-amino-adamantan-1-yl)-amide (1.0 g, 7 mmol) in DCM (75 mL), was added DIEA (2 mL, 10 mmol), and benzotriazol-1-yloxytris(dimethylamino)-phosphonium hexafluorophosphate (3.2 g, 7.3 mmol), followed by a solution of adamantane-1,3-diamine (1.3 g, 8 mmol, Zerenex Molecular Ltd., Greater Manchester, UK) in DCM (25 mL) dropwise. After stirring at rt for 16 h, the reaction mixture was washed with saturated sodium bicarbonate. The organic layer was dried over sodium sulfate and concentrated under reduced pressure. The residue was purified on a reversed phase liquid chromatography/mass spectrometry (RP-HPLC/MS) purification system (Gradient: acetonitrile in water, 18-95%, in 3.9 min with a cycle time of 5 min. A shallow gradient between 19-30% of acetonitrile was used between 0.7-2.5 min to separate close-eluting impurities. Flow rate: 100 mL/min. Mobile phase additive: 25 mM of ammonium formate. Column: Inertsil® C18, 30×50 mm, 5 μm particle size (GL Sciences, Tokyo, Japan)) to afford 0.5 g (20%) of the title compound, 6-methyl-pyridine-2-carboxylic acid (3-amino-adamantan-1-yl)-amide, as a white solid. $^1$H NMR (400 MHz, $CD_3OD$) $\delta$ 7.89-7.81 (m, 2H), 7.46-7.42 (m, 1H), 2.59 (s, 3H), 2.44-2.06 (m, 6H), 2.09-1.67 (m, 8H). ESI-MS m/z: 286.1 $(M+H)^+$.

Intermediate 1 was also made via the same synthetic procedures for Intermediate 2 (see below). Starting from 3-amino-adamantane-1-carboxylic acid methyl ester hydrochloride (14.9 g, 60.8 mmol), coupling with 6-methyl-pyridine-2-carboxylic acid afforded 3-[(6-methyl-pyridine-2-carbonyl)-amino]-adamantane-1-carboxylic acid methyl ester (14.9 g, 75%). The methyl ester was then hydrolyzed to give 3-[(6-methyl-pyridine-2-carbonyl)-amino]-adamantane-1-carboxylic acid (12.2 g, 86%). Finally, the Curtius rearrangement of 3-[(6-methyl-pyridine-2-carbonyl)-amino]-adamantane-1-carboxylic acid (10.0 g, 31.8 mmol) yielded Intermediate 1 (8.48 g, 93%).

Intermediate 2: Pyridine-2-carboxylic acid (3-amino-adamantan-1-yl)-amide

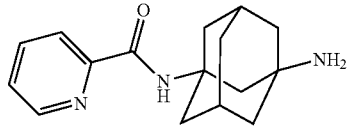

Intermediate 2 was synthesized via the process of Scheme 5, supra, as follows:

Step 1: 3-Acetylamino-adamantane-1-carboxylic acid

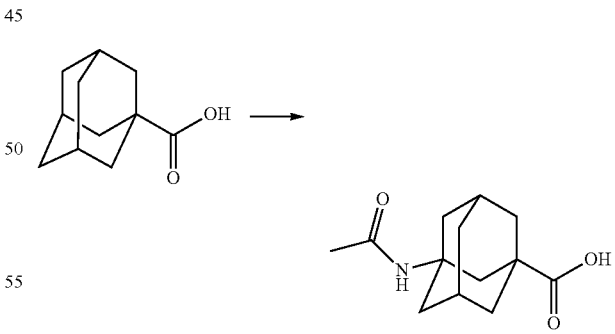

To a 10-L reactor was added 1-adamantanecarboxylic acid (503 g, 2.79 mol; TCI America, Wellesley Hills, Mass., USA) and 70% nitric acid (400 mL, 6.72 mol), and the resulting suspension was cooled at 0° C. with a recirculating chiller. To the mixture was slowly added 98% sulfuric acid (3.00 L, 55.5 mol) at such a rate that the temperature was kept below 10° C. Once the addition completed, acetonitrile (2.00 L, 38.5 mol) was added at such a rate that the temperature was kept below 10° C. After all the acetonitrile was added, the reaction was stirred at 0° C. for 1 hour. The crude reaction was then added to a 20-L reactor filled with about 10-L of ice mixed with a small amount of water and the resulting mixture was stirred and allowed to warm to room temperature. The solids were then filtered and washed with water. More solids precipitated from the acidic aqueous layer and these were filtered as well and washed with water. The combined solid material was then dried under high vacuum at 50° C. for 2 days to afford 432 g (73%) of the title compound, 3-acetylamino-adamantane-1-carboxylic acid, as a white solid.

Step 2: 3-Amino-adamantane-1-carboxylic acid hydrochloride

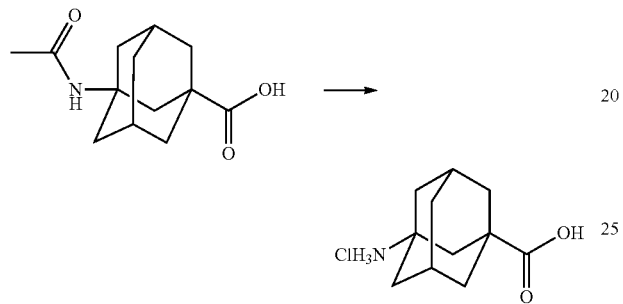

To a 3-neck 5-L flask equipped with a reflux condenser, a mechanical stirrer and a temperature probe was added 3-acetylamino-adamantane-1-carboxylic acid (432 g, 1.82 mol), water (1.00 L) and concentrated hydrochloric acid (2.44 L), and the resulting mixture was heated at 95° C. for 6 days. During this time, solid material precipitated from the solution. After cooling at 0° C., the solids were filtered and washed with acetone. The solid was then dried under high vacuum at 50° C. for about 2 hours to afford 328 g (78%) of the title compound, 3-amino-adamantane-1-carboxylic acid hydrochloride, as a white solid. $^1$H NMR (300 MHz, DMSO-$d_6$) δ 12.35 (br s, 1H), 8.27 (br s, 3H), 2.22-2.12 (m, 2H), 1.92-1.85 (m, 2H), 1.83-1.71 (m, 6H), 1.69-1.48 (m, 4H).

Step 3: 3-Amino-adamantane-1-carboxylic acid methyl ester hydrochloride

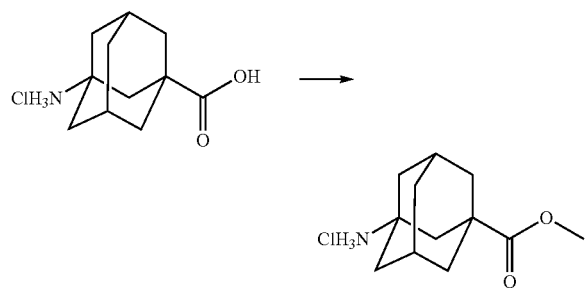

To a 3-neck 2-L flask equipped with a reflux condenser and a temperature probe was added 3-amino-adamantane-1-carboxylic acid hydrochloride (100 g, 432 mmol) and methanol (1.0 L). To this solution was slowly added thionyl chloride (15.7 mL, 216 mmol) and the reaction was heated at 60° C. for 4 hours. Once cooled to room temperature, the crude reaction mixture was concentrated under reduced pressure to remove most of the methanol. Heptane (about 1-L) was then added and the mixture was once again concentrated under reduced pressure at which point a solid began to precipitate. This process was repeated three more times, then the solids were filtered off, washed with heptane and allowed to dry in open air to afford 97.2 g (92%) of the title compound, 3-amino-adamantane-1-carboxylic acid methyl ester hydrochloride, as a white solid. $^1$H NMR (300 MHz, CDCl$_3$) δ 8.46 (br s, 3H), 3.65 (s, 3H), 2.33-2.24 (m, 2H), 2.23-2.16 (m, 2H), 2.11-1.95 (m, 4H), 1.94-1.78 (m, 4H), 1.75-1.62 (m, 2H).

Step 4: 3-[(Pyridine-2-carbonyl)-amino]adamantane-1-carboxylic acid methyl ester

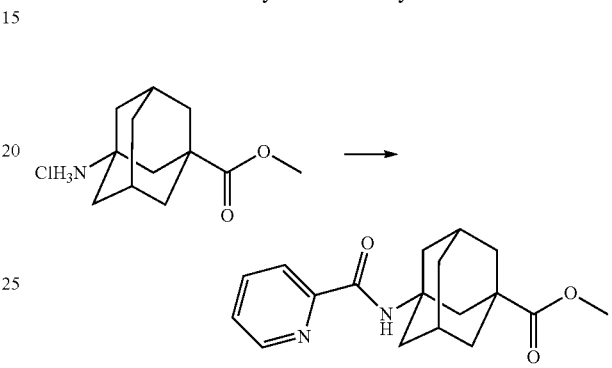

To a round bottom flask was added 3-amino-adamantane-1-carboxylic acid methyl ester hydrochloride (20.0 g, 81.4 mmol) and methylene chloride (500 mL) and the solution was cooled at 0° C. To this solution was then added triethylamine (57 mL, 0.41 mol) followed by picolinoyl chloride hydrochloride (15.2 g, 85.4 mmol; TCI America, Wellesley Hills, Mass., USA) and the reaction was stirred at 0° C. for 30 minutes, then at room temperature for 6 hours. To the reaction was added saturated aqueous sodium bicarbonate (500 mL) and the biphasic mixture was stirred vigorously for a few minutes, then transferred to a 2-L separatory funnel. The mixture was extracted, the layers separated and the aqueous layer was extracted again with methylene chloride (2×200 mL). The combined organic layers were washed with brine (300 mL), dried over sodium sulfate, filtered and concentrated under reduced pressure to afford 24.8 g (97%) of the title compound, 3-[(pyridine-2-carbonyl)-amino]-adamantane-1-carboxylic acid methyl ester, as a pale brown solid. $^1$H NMR (400 MHz, CDCl$_3$) δ 8.54-8.49 (m, 1H), 8.16 (dt, J=7.8, 1.0 Hz, 1H), 7.96 (br s, 1H), 7.83 (td, J=7.8, 1.8 Hz, 1H), 7.40 (ddd, J=7.6, 4.8, 1.3 Hz, 1H), 3.66 (s, 3H), 2.34-2.30 (m, 2H), 2.29-2.23 (m, 2H), 2.17-2.13 (m, 4H), 1.97-1.80 (m, 4H), 1.78-1.62 (m, 2H). ESI-MS m/z: 315.0 (M+H)$^+$.

Step 5: 3-[(Pyridine-2-carbonyl)-amino]adamantane-1-carboxylic acid

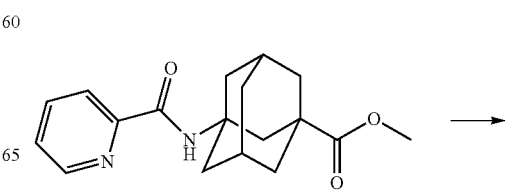

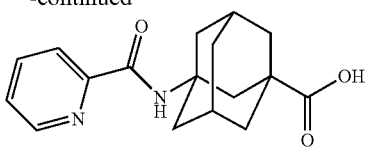

To a round bottom flask was added 3-[(pyridine-2-carbonyl)-amino]-adamantane-1-carboxylic acid methyl ester (24.8 g, 78.9 mmol), tetrahydrofuran (250 mL), water (250 mL) and lithium hydroxide monohydrate (14.9 g, 355 mmol) and the mixture was stirred vigorously at room temperature for 25 hours. The crude mixture was concentrated under reduced pressure to remove most of the tetrahydrofuran, then the aqueous solution was diluted with water (200 mL) and the pH was adjusted to about 3-4 by adding solid citric acid monohydrate. A voluminous white precipitate appeared which was filtered, washed with water and dried under high vacuum at 50° C. to afford 22.1 g (93%) of the title compound, 3-[(pyridine-2-carbonyl)-amino]-adamantane-1-carboxylic acid, as a white solid. $^1$H NMR (400 MHz, CDCl$_3$) δ 8.55-8.50 (m, 1H), 8.18 (d, J=7.7 Hz, 1H), 7.97 (br s, 1H), 7.85 (td, J=7.8, 1.8 Hz, 1H), 7.42 (ddd, J=7.6, 4.8, 1.3 Hz, 1H), 2.35-2.31 (m, 2H), 2.31-2.25 (m, 2H), 2.25-2.09 (m, 4H), 2.00-1.86 (m, 4H), 1.80-1.64 (m, 2H). ESI-MS m/z: 301.0 (M+H)$^+$.

Step 6: Pyridine-2-carboxylic acid (3-amino-adamantan-1-yl)-amide

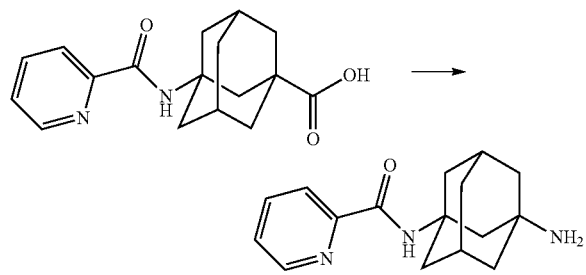

To a round bottom flask was added 3-[(pyridine-2-carbonyl)-amino]-adamantane-1-carboxylic acid (10.0 g, 33.3 mmol) and toluene (100 mL). To the suspension was added triethylamine (5.6 mL, 40 mmol) and the mixture was stirred for a few minutes until most of the solids were dissolved. To the mixture was then added diphenylphosphonic azide (7.9 mL, 37 mmol) and the reaction was stirred at room temperature for 1 hour. The reaction mixture was transferred to an addition funnel and added dropwise to a 3-neck round bottom flask equipped with a reflux condenser containing toluene (70 mL) heated at 90° C. After the addition, the reaction was stirred at 90° C. for two more hours, then allowed to cool down to room temperature. The reaction mixture was then slowly added to a flask containing 6.0 N aqueous hydrochloric acid (55 mL, 330 mmol) and stirred vigorously for 1 hour. The biphasic mixture was transferred to a separatory funnel and the toluene layer was discarded. The aqueous acidic layer was then slowly treated with solid sodium carbonate until a pH of 10 was obtained. The aqueous layer was transferred to a 500-mL separatory funnel and extracted with methylene chloride (3×100 mL). The combined organic layers were then washed with brine, dried over sodium sulfate, filtered and concentrated under reduced pressure to afford 8.38 g (93%) of the title compound, pyridine-2-carboxylic acid (3-amino-adamantan-1-yl)-amide, as a gummy foam. $^1$H NMR (300 MHz, CDCl$_3$) δ 8.55-8.50 (m, 1H), 8.16 (d, J=7.9 Hz, 1H), 7.94 (br s, 1H), 7.84 (td, J=7.7, 1.7 Hz, 1H), 7.40 (ddd, J=7.6, 4.7, 1.3 Hz, 1H), 2.31-2.21 (m, 2H), 2.13-1.97 (m, 6H), 1.71-1.51 (m, 6H). ESI-MS m/z: 272 (M+H)$^+$.

Intermediate 2 was also made via the process of Scheme 6, supra, as follows:

Step 1: Pyridine-2-carboxylic acid (3-hydroxy-adamantan-1-yl)-amide

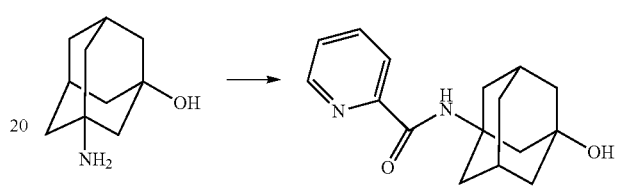

To a 40 ml vial was added picolinic acid (0.68 g, 5.5 mmol), DMF (15 ml), triethylamine (0.90 mL, 6.4 mmol), and O-(Benzotriazol-1-yl)-N,N,N',N'-tetramethyluronium hexafluorophosphate (HBTU, 2.3 g, 6.0 mmol). The mixture was stirred at rt for 5 minutes to get a clear solution. 3-Amino-adamantanol (0.84 g, 5.0 mmol; AK Scientific, 897-4G Independence Ave., Mountain View, Calif. 94043) was added to the above solution and stirred at rt for 2 hours. DMF was removed in Genevac and the residue was dissolved in DCM (20 mL), washed with 1N aqueous NaOH, water and brine, dried over Na$_2$SO$_4$, and concentrated under reduced pressure to afford 1.32 g (97%) of crude title compound, pyridine-2-carboxylic acid (3-hydroxy-adamantan-1-yl)-amide, as an oil, which became a colorless solid upon standing at room temperature. LC/MS (Gradient: acetonitrile in water, 20-85%, in 1.7 minutes with a cycle time of 2 min. Flow rate: 5.0 mL/min. Mobile phase additive: 30 mM of ammonium formate. Column: Inertsil® ODS-3, 50×4.6 mm, 3 μm particle size (GL Sciences, Tokyo, Japan)): Retention time: 0.79 min; purity (UV$_{254}$): 100%; ESI-MS m/z: 273 (M+H)$^+$. It was used in the next step without further purification.

Step 2: Pyridine-2-carboxylic acid [3-(2-chloro-acetylamino)-adamantan-1-yl]amide

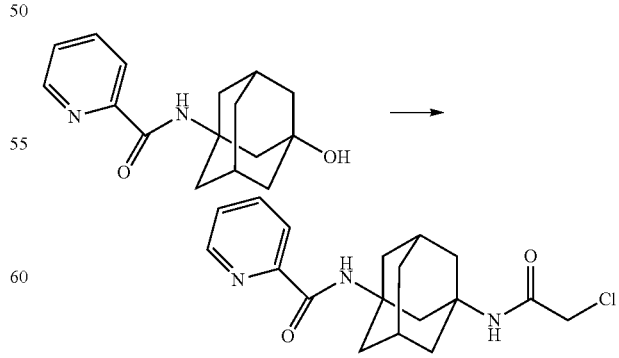

Chloroacetonitrile (2.0 mL, 32 mmol) was cooled to 0° C. Sulfuric acid (1.0 mL, 19 mmol) was added slowly at 0° C. After addition completed, the mixture was stirred at 0° C. for 5 minutes. Pyridine-2-carboxylic acid (3-hydroxy-adamantan-1-yl)-amide (0.42 g, 1.56 mmol, from step 1) was added in one portion and the mixture was stirred at rt overnight. The thick solution was poured into ice-water (10 mL). DCM (10 mL) was added. While the mixture was cooled with an ice-bath, the pH of the aqueous phase (top) was adjusted to 10-13 with 10 N aq. NaOH. The aqueous layer was extracted with DCM. The combined organic layer was washed with water and brine, dried over $Na_2SO_4$, and concentrated under reduced pressure to afford 0.53 g (96.9%) of crude title compound, pyridine-2-carboxylic acid [3-(2-chloro-acetylamino)-adamantan-1-yl]-amide, as an oil, which became a colorless solid upon standing at room temperature. LC-MS (Gradient: acetonitrile in water, 20-85%, in 1.7 minutes with a cycle time of 2 min. Flow rate: 5.0 mL/min. Mobile phase additive: 30 mM of ammonium formate. Column: Inertsil® ODS, 50×4.6 mm, 3 μm particle size (GL Sciences, Tokyo, Japan)): Retention time: 1.08 min; purity ($UV_{254}$): 100%; ESI-MS m/z: 348 (M+H)$^+$. It was used in the next step without further purification.

Step 3: Pyridine-2-carboxylic acid (3-amino-adamantan-1-yl)-amide

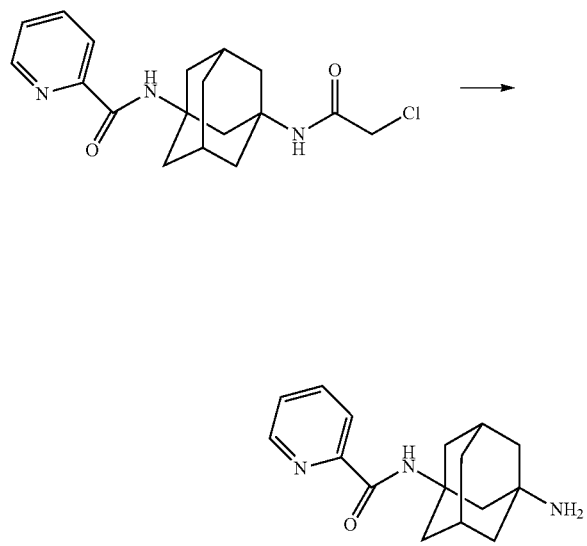

To a 40 ml vial containing pyridine-2-carboxylic acid [3-(2-chloro-acetylamino) adamantan-1-yl]-amide (1.69 g, 4.85 mmol, from step 2) and thiourea (0.56 g, 7.4 mmol), was added ethanol (20.0 mL), and acetic acid (4.0 mL). The mixture was stirred at 78° C. overnight. The reaction solution was cooled to rt, poured into water (100 mL), and the pH of the solution was adjusted to 10-13 using 10 N aq. NaOH. The mixture was transferred into a separation funnel, extracted with DCM (3×150 mL). Combined organic layer was washed with water and brine, dried over $Na_2SO_4$, and concentrated under reduced pressure to afford 1.35 g (95.4%) of crude title compound, pyridine-2-carboxylic acid (3-amino-adamantan-1-yl)-amide, as an oil, which became a colorless solid upon standing at room temperature. LC-MS (Gradient: acetonitrile in water, 10-85%, in 1.7 minutes with a cycle time of 2 min. Flow rate: 5.0 mL/min. Mobile phase additive: 30 mM of ammonium formate. Column: Inertsil® C8, 50×4.6 mm, 3 μm particle size (GL Sciences, Tokyo, Japan)): Retention time: 0.63 min; purity ($UV_{254}$): 93%; ESI-MS m/z: 272 (M+H)$^+$. It was used in the next step, amidation, without further purification.

Intermediate 3:
N-(3-Amino-adamantan-1-yl)-3-fluoro-benzamide

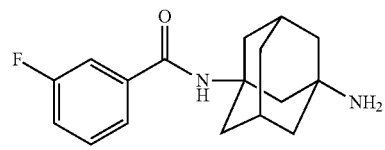

Using the same procedures as in the synthesis of Intermediate 2, Intermediate 3 was made at 4.33 mmol reaction scale, and 1.26 g (95.6%) of crude product was obtained. LC-MS (Gradient: acetonitrile in water, 10-85%, in 1.7 minutes with a cycle time of 2 min. Flow rate: 5.0 mL/min. Mobile phase additive: 30 mM of ammonium formate. Column: Inertsil® C8, 50×4.6 mm, 3 μm particle size (GL Sciences, Tokyo, Japan)): Retention time: 0.70 min; purity ($UV_{254}$): 95%. ESI-MS m/z: 289 (M+H)$^+$. It was used in the next step without further purification.

Intermediate 4: 6-Chloro-pyridine-2-carboxylic acid {3-[(pyridine-2-carbonyl)-amino]-adamantan-1-yl}-amide

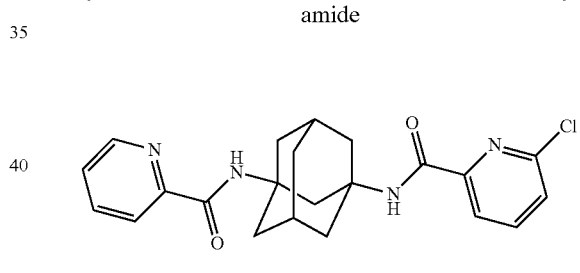

Intermediate 4 was prepared from Intermediate 2 via the process of Scheme 10, supra, as follows:

To a 40 ml vial was added 6-chloropyridine-2-carboxylic acid (0.79 g, 5.0 mmol), DMF (15 ml), triethylamine (0.90 mL, 6.4 mmol), and O-(benzotriazol-1-yl)-N,N,N',N'-tetramethyluronium hexafluorophosphate (2.3 g, 6.0 mmol). The mixture was stirred at room temperature for 5 minutes to get a clear solution. Pyridine-2-carboxylic acid (3-amino-adamantan-1-yl)-amide (Intermediate 2, 1.38 g, 4.73 mmol) was added to the solution, and the reaction mixture was stirred at room temperature for 2 hours. DMF was removed in Genevac. The residue was dissolved in DCM (20 mL), washed with aq. 1 N NaOH (15 mL), water (15 mL) and brine (15 mL), and dried over $Na_2SO_4$. Solvent was removed under reduced pressure to afford 1.85 g (95.2%) of crude title compound, 6-chloro-pyridine-2-carboxylic acid {3-[(pyridine-2-carbonyl)-amino]-adamantan-1-yl}-amide. LC-MS (Gradient: acetonitrile in water, 30-90%, in 1.7 minutes with a cycle time of 2 min. Flow rate: 5.0 mL/min. Mobile phase additive: 30 mM of ammonium formate. Column: Inertsil® C8, 50×4.6 mm, 3 μm particle size (GL Sciences, Tokyo, Japan)): Retention time: 1.17 min; purity (UV$_{254}$): 100%. ESI-MS m/z: 411 (M+H)$^+$. It was used in the next step without further purification.

Intermediate 5: 6-Chloro-pyridine-2-carboxylic acid {3-[(6-methylpyridine-2-carbonyl)-amino]-adamantan-1-yl}-amide

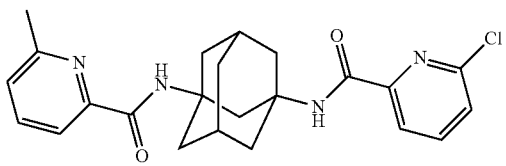

In a similar manner to Intermediate 4, Intermediate 5 was prepared from Intermediate 1 (2.00 g, 7.01 mmol). After purification by silica gel chromatography, Intermediate 5 (1.94 g, 65%) was obtained as a white solid. $^1$H NMR (300 MHz, CDCl$_3$) δ 8.13 (br s, 1H), 8.09 (d, J=7.5 Hz, 1H), 7.98 (d, J=7.7 Hz, 1H), 7.84-7.69 (m, 3H), 7.44 (d, J=7.7 Hz, 1H), 7.26 (d, 1H), 2.60-2.55 (m, 5H), 2.40-2.32 (m, 2H), 2.31-2.12 (m, 8H), 1.76-1.70 (m, 2H). ESI-MS m/z: 425.0 (M+H)$^+$.

Intermediate 6: 6-Chloro-pyridine-2-carboxylic acid [3-(3-fluoro-benzoylamino)-adamantan-1-yl]-amide

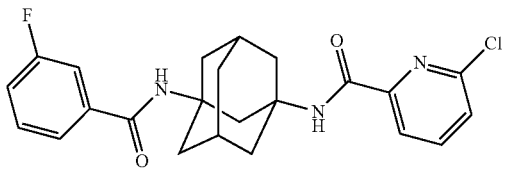

In a similar manner to Intermediate 4, Intermediate 6 was prepared from Intermediate 3 at a 4.6 mmol reaction scale. Crude product (1.99 g, 97%) was obtained. LC-MS (Gradient: acetonitrile in water, 30-90%, in 1.7 minutes with a cycle time of 2 min. Flow rate: 5.0 mL/min. Mobile phase additive: 30 mM of ammonium formate. Column: Inertsil® C8, 50×4.6 mm, 3 μm particle size (GL Sciences, Tokyo, Japan)): Retention time: 1.21 min; purity (UV$_{254}$): 100%. ESI-MS m/z: 428 (M+H)$^+$. It was used in the next step without further purification.

Intermediate 7: Pyrazine-2-carboxylic acid (3-amino-adamantan-1-yl)-amide

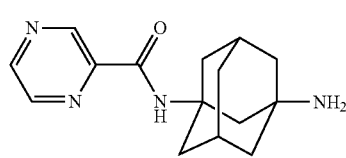

Intermediate 7 was synthesized via the process of Scheme 5 from compound 4, supra, as follows:

Step 1: 3-[(Pyrazine-2-carbonyl)-amino]adamantane-1-carboxylic acid

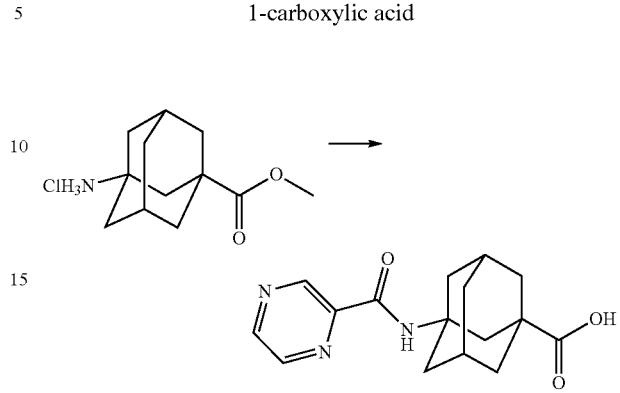

To a round bottom flask was added 3-amino-adamantane-1-carboxylic acid methyl ester hydrochloride (7.00 g, 28.5 mmol), 2-pyrazinecarboxylic acid (3.71 g, 29.9 mmol) and methylene chloride (200 mL). The mixture was stirred vigorously and treated with PyBOP® (15.6 g, 29.9 mmol) followed by triethylamine (9.9 mL, 71 mmol), and then stirred at room temperature for 16 hours. To the reaction was added saturated aqueous sodium bicarbonate (200 mL) and the biphasic mixture was stirred vigorously for a few minutes, then transferred to a 1-L separatory funnel. The mixture was extracted, the layers separated and the aqueous layer was extracted again with methylene chloride (200 mL). The combined organic layers were washed with brine, dried over sodium sulfate, filtered and concentrated under reduced pressure. The residue was then dissolved in tetrahydrofuran (200 mL) and water (200 mL) was added. To the biphasic mixture was added lithium hydroxide monohydrate (5.38 g, 128 mmol), and the resultant mixture stirred vigorously at room temperature for 22 hours. Most of the volatiles were removed under reduced pressure and the resulting aqueous solution was transferred to a 500-mL separatory funnel and washed with methylene chloride (3×150 mL). The aqueous layer was diluted with water (200 mL) and the pH was adjusted to about 3-4 by adding solid citric acid monohydrate. A voluminous white precipitate appeared that was filtered, washed with water and dried under high vacuum at 50° C. to afford 8.11 g (95%) of the title compound, 3-[(pyrazine-2-carbonyl)-amino]-adamantane-1-carboxylic acid, as a white solid. $^1$H NMR (300 MHz, CDCl$_3$) δ 11.14-10.07 (br s, 1H), 9.38 (d, J=1.5 Hz, 1H), 8.74 (d, J=2.5 Hz, 1H), 8.50 (dd, J=2.4, 1.5 Hz, 1H), 7.68 (br s, 1H), 2.35-2.25 (m, 4H), 2.23-2.08 (m, 4H), 2.00-1.86 (m, 4H), 1.81-1.64 (m, 2H). ESI-MS m/z: 301.9 (M+H)$^+$.

Step 2: Pyrazine-2-carboxylic acid (3-amino-adamantan-1-yl)-amide

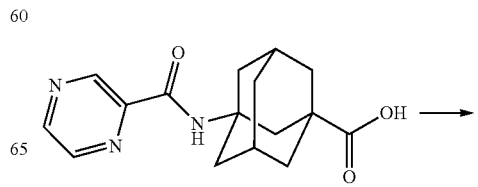

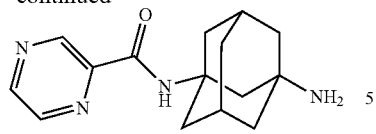

Using the same procedure as that used to prepare Intermediate 2 in step 6, from 3-[(pyrazine-2-carbonyl)-amino]-adamantane-1-carboxylic acid (4.00 g, 13.3 mmol), the Curtius rearrangement afforded 3.56 g (99%) of the title compound, pyrazine-2-carboxylic acid (3-amino-adamantan-1-yl)-amide, as an off-white solid. $^1$H NMR (300 MHz, CDCl$_3$) δ 9.37 (d, J=1.4 Hz, 1H), 8.73 (d, J=2.5 Hz, 1H), 8.49 (dd, J=2.4, 1.5 Hz, 1H), 7.64 (br s, 1H), 2.31-2.21 (m, 2H), 2.14-1.95 (m, 6H), 1.71-1.51 (m, 6H) (Note: the —NH$_2$ is hidden between 2.52-1.78 ppm). ESI-MS m/z: 273.0 (M+H)$^+$.

Intermediate 8: 6-Methyl-pyrazine-2-carboxylic acid (3-amino-adamantan-1-yl)-amide

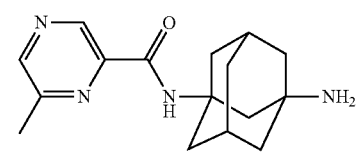

Intermediate 8 was synthesized via the process of Scheme 5 from compound 4, supra, as follows:

Step 1: 3-[(6-Methyl-pyrazine-2-carbonyl)-amino]-adamantane-1-carboxylic acid

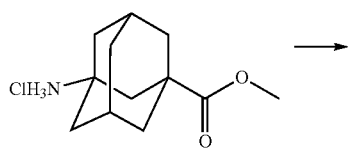

Using the same procedure as that used to prepare Intermediate 7 in step 1, from 3-amino-adamantane-1-carboxylic acid methyl ester hydrochloride (7.00 g, 28.5 mmol) and 6-methylpyrazine-2-carboxylic acid (4.13 g, 29.9 mmol, RihaChem, Kostalov Czech Republic), the coupling reaction with PyBOP®, followed by basic hydrolysis of the methyl ester group, afforded 8.01 g (89%) of the title compound, 3-[(6-methyl-pyrazine-2-carbonyl)-amino]-adamantane-1-carboxylic acid, as a white solid. $^1$H NMR (400 MHz, CDCl$_3$) δ 12.03-10.32 (br s, 1H), 9.17 (s, 1H), 8.60 (s, 1H), 7.72 (br s, 1H), 2.60 (s, 3H), 2.35-2.26 (m, 4H), 2.26-2.18 (m, 2H), 2.16-2.07 (m, 2H), 2.00-1.86 (m, 4H), 1.80-1.65 (m, 2H). ESI-MS m/z: 316.0 (M+H)$^+$.

Step 2: 6-Methyl-pyrazine-2-carboxylic acid (3-amino-adamantan-1-yl)amide

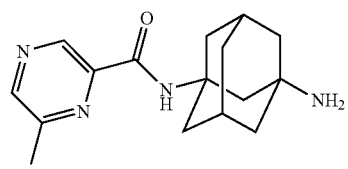

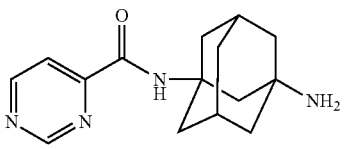

Using the same procedure as that used to prepare Intermediate 2 in step 6, from 3-[(6-methyl-pyrazine-2-carbonyl)-amino]-adamantane-1-carboxylic acid (3.00 g, 9.51 mmol), the Curtius rearrangement afforded 2.65 g (97%) of the title compound, 6-methyl-pyrazine-2-carboxylic acid (3-amino-adamantan-1-yl)amide, as an off-white solid. $^1$H NMR (400 MHz, CDCl$_3$) δ 9.17 (s, 1H), 8.59 (s, 1H), 7.69 (br s, 1H), 2.60 (s, 3H), 2.32-2.21 (m, 2H), 2.13-1.97 (m, 6H), 1.70-1.52 (m, 6H) (Note: the —NH$_2$ is hidden between 2.41-1.29 ppm). ESI-MS m/z: 287.0 (M+H)$^+$.

Intermediate 9: Pyrimidine-4-carboxylic acid (3-amino-adamantan-1-yl)-amide

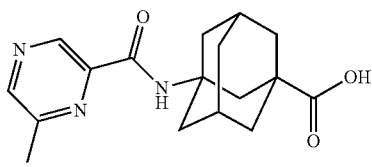

Using the same procedures as in the synthesis of Intermediate 7, Intermediate 9 was made at 16.8 mmol reaction scale from 3-amino-adamantane-1-carboxylic acid methyl ester hydrochloride and pyrimidine-4-carboxylic acid (Ark Pharm Inc., Libertyville, Ill., USA), and 4.00 g (88%) of crude product was obtained. LC-MS (Gradient: acetonitrile in water, 20-85%, in 1.7 minutes with a cycle time of 2 min. Flow rate: 5.0 mL/min. Mobile phase additive: 30 mM of ammonium formate. Column: Inertsil® ODS, 50×4.6 mm, 3 µm particle size (GL Sciences)): Retention time: 0.24 min;

purity (UV$_{254}$): 95%. ESI-MS m/z: 273 (M+H)$^+$. It was used in the next step without further purification.

Intermediate 10: 2-Methyl-pyrimidine-4-carboxylic acid (3-amino-adamantan-1-yl)-amide

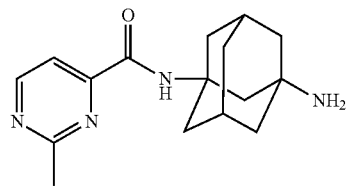

Using the same procedures as in the synthesis of Intermediate 7, Intermediate 10 was made at 15.8 mmol reaction scale from 3-amino-adamantane-1-carboxylic acid methyl ester hydrochloride and 2-methyl-pyrimidine-4-carboxylic acid (Ark Pharm Inc.), and 4.6 g (100%) of crude product was obtained. LC-MS (Gradient: acetonitrile in water, 20-85%, in 1.7 minutes with a cycle time of 2 min. Flow rate: 5.0 mL/min. Mobile phase additive: 30 mM of ammonium formate. Column: Inertsil® ODS, 50×4.6 mm, 3 μm particle size (GL Sciences)): Retention time: 0.30 min; purity (UV$_{254}$): 82%. ESI-MS m/z: 287 (M+H)$^+$. It was used in the next step without further purification.

Intermediate 11:
4-Trifluoromethyl-pyrimidine-2-carboxylic acid

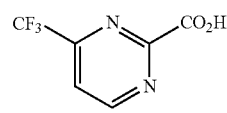

Intermediate 11 was made via the process of Scheme 11, supra, as follows:

Step 1: 4-Trifluoromethyl-pyrimidine-2-carbonitrile

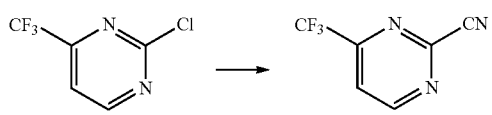

To a solution 2-chloro-4-(trifluoromethyl)pyrimidine (5.00 g, 27.4 mmol) in dimethyl sulfoxide (25 mL) was added sodium cyanide (1.68 g, 34.2 mmol). The reaction was stirred at room temperature for 30 minutes and poured into cold saturated aqueous NaHCO$_3$ solution. The mixture was transferred to a 100 mL reparatory funnel and extracted with ethyl ether (3×50 mL). The combined organic layers were washed with brine (50 mL), dried over sodium sulfate, filtered, and concentrated under reduced pressure to afford the title compound, 4-trifluoromethyl-pyrimidine-2-carbonitrile, as a brown oil, which was used in the next step without further purification. $^1$H NMR (400 MHz, CDCl$_3$) δ 9.16 (d, J=5.1 Hz, 1H), 7.88 (d, J=5.1 Hz, 1H).

Step 2: 4-Trifluoromethyl-pyrimidine-2-carboxylic acid

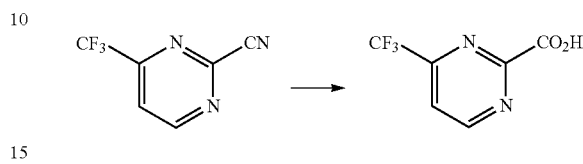

The crude 4-trifluoromethyl-pyrimidine-2-carbonitrile from Step 1 was dissolved in a solution of hydrogen chloride in water (6 M, 20.0 mL) and heated at reflux temperature overnight. The reaction mixture was cooled to room temperature, and concentrated under reduced pressure. Toluene (20 mL) was then added and the mixture was concentrated under reduced pressure. This process was repeated with 1,4-dioxane and ethyl ether, then the solids were filtered off. The filtrate was concentrated under reduced pressure to afford 4.80 g (82.1%) of the title compound, 4-trifluoromethyl-pyridine-2-carboxylic acid, as brown solid, which was used in the next step without further purification. $^1$H NMR (400 MHz, DMSO-d$_6$) δ9.35 (d, J=5.0 Hz, 1H), 8.25 (d, J=5.1 Hz, 1H).

Intermediate 12: 4-Methyl-pyrimidine-2-carboxylic acid

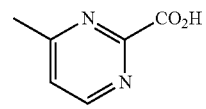

Step 1: 4-Methyl-pyrimidine-2-carbonitrile

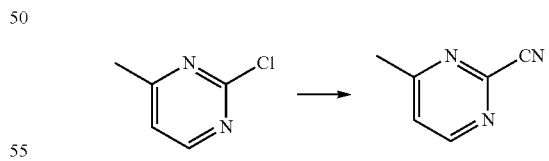

To a solution of 2-chloro-4-methylpyrimidine (3.00 g, 23.3 mmol; 3B Pharmachem International, China) in ethyl ether (24 mL) was added a solution of sodium cyanide (2.86 g, 58.3 mmol) in trimethylamine solution (1:3, trimethylamine:water, 24.0 mL). The reaction mixture was stirred at room temperature overnight. The aqueous layer was extracted with ethyl ether (3×20 mL). The combined organic layers were dried over MgSO$_4$, filtered, and concentrated under reduced pressure to yield the title compound, 4-methyl-pyrimidine-2-carbonitrile (1.80 g; 64.8%), which was used in the next step without further purification. $^1$H NMR (400 MHz, D$_2$O) δ 8.64 (d, J=5.4 Hz, 1H), 7.59 (d, J=5.5 Hz, 1H).

Step 2: 4-Methyl-pyrimidine-2-carboxylic acid

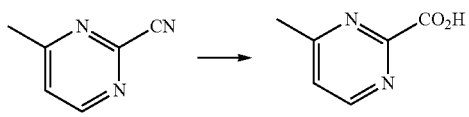

The solution of 4-methyl-pyrimidine-2-carbonitrile (500 mg, 4.20 mmol) and sodium hydroxide (504 mg, 12.6 mmol) in water (12.5 mL) was stirred at 60° C. for 1 hour. The reaction mixture was cooled to room temperature, acidified to pH ~2 with citric acid and extracted with CHCl$_3$:i-PrOH (3:1, 2×20 mL). The combined organic layers were dried over MgSO$_4$ and concentrated under reduced pressure to afford 0.294 g of the title compound, 4-methyl-2-pyrimidinecarboxylic acid (51%), which was used in the next step without further purification. $^1$H NMR (300 MHz, D$_2$O) δ 8.50 (d, J=5.2 Hz, 1H), 7.31 (d, J=5.3 Hz, 1H).

3. Preparation of Compounds of the Invention

Unless specified otherwise, the reagents used in the preparation of compounds, including intermediates, of the present invention were purchased from Sigma-Aldrich Corporation (St. Louis, Mo., USA).

Example 1

N,N'-(1,3-adamantylene)bis(6-methyl-pyridine-2-carboxamide)

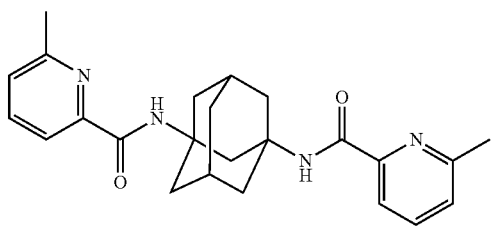

Example 1 was prepared via the process of Scheme 1, supra, as follows:

To a vial containing 6-methyl picolinic acid (40 mg, 0.3 mmol), methylene chloride (10 mL) and N,N-diisopropylethylamine (60 mg, 0.5 mmol), was added N-(3-dimethylaminopropyl)-N'-ethylcarbodiimide hydrochloride (60 mg, 0.3 mmol). The mixture was stirred for 5 minutes. Adamantane-1,3-diamine hydrochloride salt (20 mg, 0.1 mmol; Zerenex™ Molecular Ltd., Greater Manchester, UK) was added and the reaction was allowed to proceed for 16 h. The reaction mixture was washed with saturated sodium bicarbonate, dried over sodium sulfate and concentrated under reduced pressure. The residue was purified on a reversed phase liquid chromatography/mass spectrometry (RP-HPLC/MS) purification system (Gradient: acetonitrile in water, 25-95%, in 3.9 min with a cycle time of 5 min. A shallow gradient between 28-58% of acetonitrile was used between 0.75-3.5 min to separate close-eluting impurities. Flow rate: 100 mL/min. Mobile phase additive: 25 mM of ammonium acetate. Column: Inertsil® C8, 30×50 mm, 5 um particle size) to afford the title compound (33 mg, 80%) as an off white oil. $^1$H NMR (400 MHz, CDCl$_3$) δ 8.09 (s, br, 2H), 7.96 (d, J=7.76 Hz, 2H), 7.70 (t, J=7.70 Hz, 2H), 7.27-7.22 (m, 2H), 2.58-2.55 (m, 2H), 2.38-2.13 (m, 10H), 1.75-1.71 (m, 2H). ESI-MS m/z: 405.0 (M+H)$^+$.

Example 2

N,N'-(1,3-adamantylene)bis(2-pyridinecarboxamide)

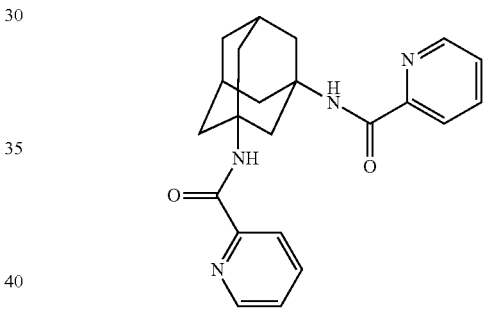

Example 2 was prepared via the process of Scheme 1, supra, as follows:

Into a vial containing adamantane-1,3-diamine (50 mg, 0.3 mmol; Zerenex™ Molecular Ltd., Greater Manchester, UK) and methylene chloride (10 mL) at 0° C. was added N,N-diisopropylethylamine (200 mg, 2 mmol; Alfa Aesar®, Ward Hill, Mass., USA). Into the reaction was added pyridine-2-carbonyl chloride (60 mg, 0.4 mmol; TCI America, Wellesley Hills, Mass., USA). After stirring at room temperature for 16 h, the reaction mixture was washed with saturated sodium bicarbonate, dried over sodium sulfate and concentrated under reduced pressure. The residue was purified on a reversed phase liquid chromatography/mass spectrometry (RP-HPLC/MS) purification system (Gradient: acetonitrile in water, 30-95%, in 3.9 min with a cycle time of 5 min. Flow rate: 100 mL/min. Mobile phase additive: 25 mM of ammonium formate. Column: Inertsil® C8, 30×50 mm, 5 um particle size) to obtain the title compound as a brownish oil. (58 mg, 50%). $^1$H NMR (300 MHz, CDCl$_3$) δ 8.51 (d, J=4.86 Hz, 2H), 8.15 (d, J=7.85 Hz, 2H), 8.03 (s, br 2H), 7.83 (d, J=7.70 Hz, 2H), 7.43-7.37 (m, 2H), 2.58 (s, br, 2H), 2.38-2.31 (m, 2H), 2.20-2.13 (m, 8H), 1.76-1.71 (m, 2H). ESI-MS m/z: 377.0 (M+H)$^1$.

In an analogous manner to Example 2, Examples 3-5 of Table 1 (below) were made from commercially available aryl or heteroaryl carbonyl chloride on 0.1 to 0.3 mmol reaction scales.

Example 6

Pyridine-2-carboxylic acid [3-(3-chloro-benzoylamino)-adamantan-1-yl]-amide

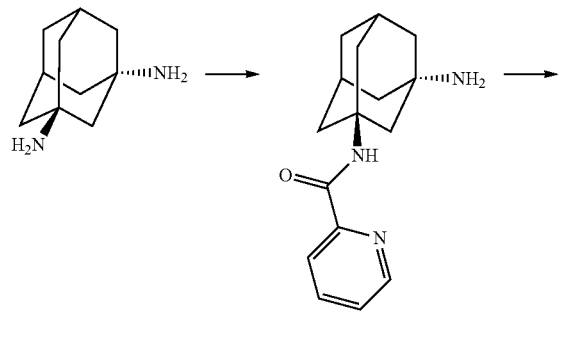

Example 6 was prepared via the process of Schemes 4 and 3, supra, as follows:

To a vial containing adamantane-1,3-diamine (50 mg, 0.3 mmol) and tetrahydrofuran (5 mL) was added dropwise, 5M aq NaOH (0.6 mL, 3 mmol). With vigorous stirring, picolinoyl chloride hydrochloride (50 mg, 0.3 mmol) was added in portions. After stirring at room temperature for 16 h, the reaction mixture was partitioned into dichloromethane and saturated sodium bicarbonate. The organic layer was dried over sodium sulfate and concentrated under reduced pressure. The residue was retaken into 5 mL of DCM (dichloromethane). To the suspension was added DIEA (N,N-diisopropyl-ethylamine) (160 mg, 1.2 mmol) and 3-chloro-benzoyl chloride (79 mg, 0.45 mmol). The reaction mixture was stirred at room temperature for 16 h, washed with saturated sodium bicarbonate, dried over sodium sulfate and concentrated under reduced pressure. The residue was purified on a reversed phase liquid chromatography/mass spectrometry (RP-HPLC/MS) purification system (Gradient: acetonitrile in water, 25-95%, in 3.9 min with a cycle time of 5 min. A shallow gradient between 35-65% of acetonitrile was used between 0.75-3.5 min to separate close-eluting impurities. Flow rate: 100 mL/min. Mobile phase additive: 25 mM of ammonium acetate. Column: Inertsil® C8, 30×50 mm, 5 um particle size) to afford the title compound (28 mg, 22%) as an off white oil. $^1$H NMR (400 MHz, CDCl$_3$) δ 8.51 (d, J=4.75 Hz, 1H), 8.15 (d, J=7.84 Hz, 1H), 8.03 (s, br 1H), 7.83 (t, J=7.72 Hz, 1H), 7.69 (t, J=1.82 Hz, 1H), 7.57 (d, J=7.60 Hz, 1H), 7.46-7.31 (m, 3H), 5.87 (s, br 1H), 2.56 (s, br, 2H), 2.38-2.31 (m, 2H), 2.24-2.12 (m, 8H), 1.76-1.69 (m, 2H). ESI-MS m/z: 410.0 (M+H)$^+$.

In an analogous manner to Example 6, Examples 7-10 in Table 1 (below) were made from commercially available aryl or heteroaryl carbonyl chloride on a 0.3 mmol reaction scale.

Example 11

N,N'-(1,3-Adamantylene)bis(4-methyl-pyridine-2-carboxamide)

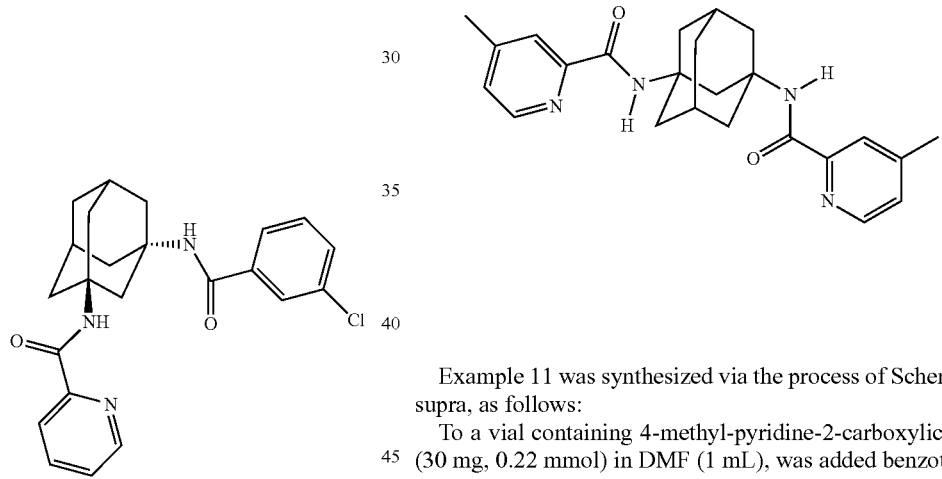

Example 11 was synthesized via the process of Scheme 1, supra, as follows:

To a vial containing 4-methyl-pyridine-2-carboxylic acid (30 mg, 0.22 mmol) in DMF (1 mL), was added benzotriazole-1-yl-oxy-tris-(dimethylamino)-phosphonium hexafluorophosphate (97 mg, 0.22 mmol), DIEA (40 mg, 0.3 mmol; Alfa Aesar, Ward Hill, Mass., USA), followed by adamantane-1,3-diamine (20 mg, 0.1 mmol in 1 mL of THF; Zerenex Molecular Ltd., Greater Manchester, UK). After stirring for 16 h at rt, the reaction mixture was partitioned into dichloromethane and saturated sodium bicarbonate. The organic layer was dried over sodium sulfate, filtered and concentrated under reduced pressure. The residue was purified on a reversed phase liquid chromatography/mass spectrometry (RP-HPLC/MS) purification system (Gradient: acetonitrile in water, 30-95%, in 3.7 minutes with a cycle time of 5 min. Flow rate: 100 mL/min. Mobile phase additive: 25 mM of ammonium formate. Column: Inertsil® C8, 30×50 mm, 5 μm particle size (GL Sciences, Tokyo, Japan)) to afford 18 mg (40%) of the title compound, N,N'-(1,3-adamantylene)bis(4-methyl-pyridine-2-carboxamide, as an off-white oil. $^1$H NMR (400 MHz, CDCl$_3$) δ 8.35 (d, J=4.9 Hz, 2H), 8.02 (s, br, 2H), 7.98-7.96 (m, 2H), 7.21-7.19 (m, 2H), 2.57-2.55 (m, 2H), 2.41 (s, 6H), 2.36-2.31 (m, 2H), 2.25-2.13 (m, 8H), 1.74-1.70 (m, 2H). ESI-MS m/z: 405.0 (M+H)$^+$.

In an analogous manner to Example 11, Examples 12-16 in Table 1 (below) were made from commercially available aryl or heteroaryl carboxylic acids on 0.1 to 0.3 mmol reaction scales.

Example 17

N,N'-(1,3-Adamantylene)bis(1-methyl-1H-pyrazole-3-carboxamide)

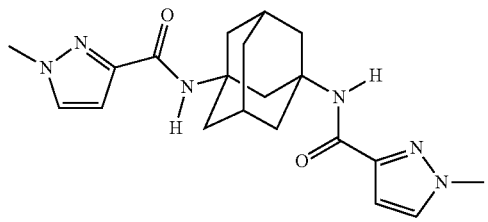

Example 17 was synthesized from heteroaryl carbonyl chloride via the process of Scheme 1, supra, as follows:

To a solution of adamantane-1,3-diamine (20 mg, 0.1 mmol; Zerenex Molecular Ltd., Greater Manchester, UK) in THF (4 mL), was added 1-methyl-1H-pyrazole-3-carbonyl chloride (40 mg, 0.3 mmol) and DIEA (40 mg, 0.3 mmol). After stirring for 16 h at rt, the reaction mixture was partitioned into dichloromethane and saturated sodium bicarbonate. The organic layer was dried over sodium sulfate, filtered and concentrated under reduced pressure. The residue was purified on a RP-HPLC/MS purification system (Gradient: acetonitrile in water, 18-95%, in 3.9 minutes with a cycle time of 5 min. Flow rate: 100 mL/min. Mobile phase additive: 25 mM of ammonium acetate. Column: Inertsil® C8, 30×50 mm, 5 µm particle size (GL Sciences, Tokyo, Japan)) to afford 19 mg (50%) of the title compound, N,N'-(1,3-adamantylene) bis(1-methyl-1H-pyrazole-3-carboxamide, as a colorless oil. $^1$H NMR (400 MHz, CDCl$_3$) δ 7.32 (d, J=2.3 Hz, 2H), 6.74-6.71 (m, 4H), 3.89 (s, 6H), 2.49 (s, br, 2H), 2.33-2.26 (m, 2H), 2.23-2.06 (m, 8H), 1.72-1.64 (m, 2H). ESI-MS m/z: 383.1 (M+H)$^+$.

Example 18

5-Methyl-pyrazine-2-carboxylic acid {3-[(1-methyl-1H-pyrazole-3-carbonyl)-amino]-adamantan-1-yl}-amide

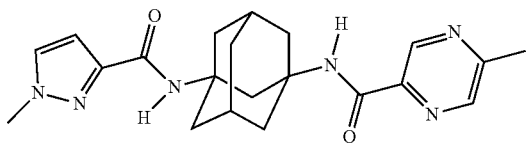

Example 18 was synthesized via the process of Scheme 2 using commercially available carboxylic acids, supra, as follows:

To a solution of adamantane-1,3-diamine (20 mg, 0.1 mmol; Zerenex Molecular Ltd., Greater Manchester, UK) in DCM (2 mL) was added DIEA (26 mg, 0.15 mmol), 1-methyl-1H-pyrazole-3-carboxylic acid (14 mg, 0.11 mmol), 5-methyl-pyrazine-2-carboxylic acid (15 mg, 0.11 mmol) and benzotriazol-1-yl-oxytripyrrolidinophosphonium hexafluorophosphate (110 mg, 0.20 mmol). After stirring for 3 hours at rt, the reaction mixture was partitioned into dichloromethane and saturated sodium bicarbonate. The organic layer was dried over sodium sulfate, filtered and concentrated under reduced pressure. The residue was purified on a RP-HPLC/MS purification system (Gradient: acetonitrile in water, 25-95%, in 3.4 minutes with a cycle time of 5 min. A shallow gradient between 25-50% of acetonitrile was used between 0.75-3.3 min to separate close-eluting impurities. Flow rate: 100 mL/min. Mobile phase additive: 25 mM of ammonium formate. Column: Inertsil® C8, 30×50 mm, 5 µm particle size (GL Sciences, Tokyo, Japan)) to afford 15 mg (37%) of the title compound, 5-methyl-pyrazine-2-carboxylic acid {3-[(1-methyl-1H-pyrazole-3-carbonyl)-amino]-adamantan-1-yl}-amide, as a colorless oil. $^1$H NMR (400 MHz, CDCl$_3$) δ 9.22 (s, 1H), 8.34-8.33 (m, 1H), 7.67 (s, br, 1H), 7.33 (d, J=2.3 Hz, 1H), 6.76-6.72 (m, 2H), 3.89 (s, 3H), 2.64 (s, 3H), 2.54 (s, br, 2H), 2.37-2.09 (m, 10H), 1.73-1.68 (m, 2H). ESI-MS m/z: 395.0 (M+H)$^+$.

Example 19

Thiazole-2-carboxylic acid {3-[(1-methyl-1H-pyrazole-3-carbonyl)-amino]-adamantan-1-yl}-amide

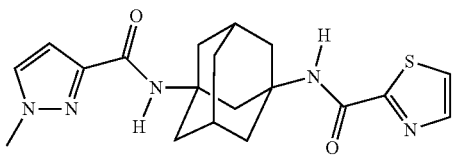

Example 19 was synthesized via the process of Scheme 2 using commercially available carboxylic acid chlorides, supra, as follows:

To a solution of adamantane-1,3-diamine (17 mg, 0.1 mmol, Zerenex Molecular Ltd., Greater Manchester, UK) in DCM (2 mL) was added DIEA (20 mg, 0.15 mmol), 1-methyl-1H-pyrazole-3-carbonyl chloride (16 mg, 0.11 mmol; Maybridge Chemical Co., Cornwall, UK) and thiazole-2-carbonyl chloride (16 mg, 0.11 mmol; Maybridge Chemical Co., Cornwall, UK). After stirring at room temperature for 3 h, the reaction mixture was partitioned into dichloromethane and saturated sodium bicarbonate. The organic layer was dried over sodium sulfate and concentrated under reduced pressure. The residue was purified on a RP-HPLC/MS purification system (Gradient: acetonitrile in water, 25-95%, in 3.9 minutes with a cycle time of 5 min. A shallow gradient between 27-53% of acetonitrile was used between 0.75-3.3 min to separate close-eluting impurities. Flow rate: 100 mL/min. Mobile phase additive: 25 mM of ammonium formate. Column: Inertsil® C8, 30×50 mm, 5 µm particle size (GL Sciences, Tokyo, Japan)) to afford 15 mg (38%) of the title compound, thiazole-2-carboxylic acid {3-[(1-methyl-1H-pyrazole-3-carbonyl)-amino]-adamantan-1-yl}-amide, as a colorless oil. $^1$H NMR (400 MHz, CDCl$_3$) δ 7.81 (d, J=3.2 Hz, 1H), 7.53 (d, J=3.2 Hz, 1H), 7.33 (d, J=2.3 Hz, 1H), 7.14 (d, J=2.3 Hz, 1H), 6.74-6.71 (m, 2H), 3.89 (s, 3H), 2.55-2.51 (m, 2H), 2.35-2.29 (m, 2H), 2.19-2.11 (m, 8H), 1.71-1.67 (m, 2H), ESI-MS m/z: 386.0 (M+H)+.

Example 20

6-Methyl-pyridine-2-carboxylic acid {3-[(1-methyl-1H-pyrazole-3-carbonyl)-amino]-adamantan-1-yl}-amide

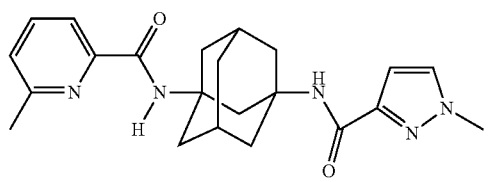

Example 20 was synthesized from Intermediate 1 via the process of Scheme 3, supra, as follows:

To a solution of 6-methyl-pyridine-2-carboxylic acid (3-amino-adamantan-1-yl)-amide (Intermediate 1, 20 mg, 0.07 mmol) in DCM (5 mL) was added DIEA (30 mg, 0.2 mmol) and 1-methyl-1H-pyrazole-3-carbonyl chloride (20 mg, 0.1 mmol, Maybridge Chemical Co., Cornwall, UK). After stirring at room temperature for 16 h, the reaction mixture was partitioned into dichloromethane and saturated sodium bicarbonate. The organic layer was dried over sodium sulfate and concentrated under reduced pressure. The residue was purified on a RP-HPLC/MS purification system (Gradient: acetonitrile in water, 25-95%, in 3.9 minutes with a cycle time of 5 min. Flow rate: 100 mL/min. Mobile phase additive: 25 mM of ammonium formate. Column: Inertsil® C8, 30×50 mm, 5 µm particle size (GL Sciences, Tokyo, Japan)) to afford 10 mg (30%) of the title compound, 6-methyl-pyridine-2-carboxylic acid {3-[(1-methyl-1H-pyrazole-3-carbonyl)-amino]-adamantan-1-yl}-amide, as a white solid. ¹H NMR (400 MHz, CDCl₃) δ 8.07 (s, br, 1H), 7.95 (d, J=7.7 Hz, 1H), 7.69 (t, J=7.8 Hz, 1H), 7.33 (d, J=2.3 Hz, 1H), 7.26-7.21 (m, 1H), 6.76-6.72 (m, 2H), 3.89 (s, 3H), 2.55 (s, 3H), 2.54-2.52 (m, 2H), 2.35-2.08 (m, 10H), 1.72-1.69 (m, 2H). ESI-MS m/z: 394.1 (M+H)+.

In an analogous manner to Example 20, Examples 21-57 in Table 1 (below) were made from commercially available aryl, heteroaryl or aliphatic carboxylic acids, or aryl, heteroaryl or aliphatic carbonyl chlorides on 0.05-7.0 mmol reaction scales.

In an analogous manner to Example 20, Examples 114-130, 132-139 and 142 in Table 1 (below) were made from commercially available aryl, heteroaryl or aliphatic carboxylic acids, or aryl, heteroaryl or aliphatic carbonyl chlorides.

In an analogous manner to Example 20, Examples 131 and 141 in Table 1 (below) were made from 4-trifluoromethyl-pyrimidine-2-carboxylic acid (Intermediate 11) and 4-methyl-pyrimidine-2-carboxylic acid (Intermediate 12).

Example 58

6-Methyl-pyrazine-2-carboxylic acid {3-[(pyridine-2-carbonyl)-amino]-adamantan-1-yl}-amide

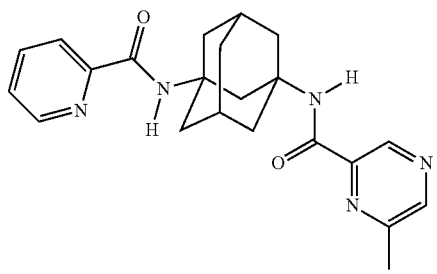

Example 58 was synthesized from Intermediate 2 via the process of Scheme 3, supra, as follows:

To a round bottom flask was added pyridine-2-carboxylic acid (3-amino-adamantan-1-yl)-amide (3.10 g, 11.0 mmol, Intermediate 2), 6-methylpyrazine-2-carboxylic acid (1.83 g, 13.3 mmol; RihaChem, Kostalov, Czech Republic) and methylene chloride (120 mL). To the solution was then added PyBOP® (6.90 g, 13.3 mmol) followed by triethylamine (3.85 mL, 27.6 mmol) and the reaction was stirred for two hours at room temperature. The reaction was transferred to a 500-mL reparatory funnel with methylene chloride (50 mL) and saturated aqueous sodium bicarbonate (150 mL), and extracted with methylene chloride. The organic layer was separated and the aqueous layer was extracted again with methylene chloride (2×75 mL). The combined organic layers were washed with brine (150 mL), dried over sodium sulfate, filtered and concentrated under reduced pressure. The residue was purified on a RP-HPLC/MS purification system (Gradient: acetonitrile in water, 27-95%, in 3.5 min with a shallow gradient from 30-60% between 0.75-3.4 min and a cycle time of 5 min. Flow rate: 100 mL/min. Mobile phase additive: 38 mM of ammonium acetate. Column: Inertsil® C8, 30×50 mm, 5 µm particle size (GL Sciences, Tokyo, Japan). Mobile phase and column temperature: 50° C.). Fractions were then concentrated under reduced pressure to remove most of the acetonitrile, the resulting aqueous layer was made basic with solid sodium carbonate (pH>10) and the aqueous layer was extracted with ethyl acetate (3×200 mL). The combined organic layers were washed with brine, dried over sodium sulfate, filtered and concentrated under reduced pressure to afford 3.21 g (74%) of the title compound, 6-methyl-pyrazine-2-carboxylic acid {3-[(pyridine-2-carbonyl)-amino]-adamantan-1-yl}-amide, as a white solid. ¹H NMR (400 MHz, CDCl₃) δ 9.17 (s, 1H), 8.58 (s, 1H), 8.54-8.50 (m, 1H), 8.17 (dt, J=7.8, 1.0 Hz, 1H), 8.06 (br s, 1H), 7.85 (td, J=7.7, 1.7 Hz, 1H), 7.77 (br s, 1H), 7.42 (ddd, J=7.6, 4.8, 1.3 Hz, 1H), 2.61-2.57 (m, 5H), 2.40-2.28 (m, 4H), 2.27-2.19 (m, 2H), 2.18-2.08 (m, 4H), 1.78-1.68 (m, 2H). ESI-MS m/z: 392.0 (M+H)+.

In an analogous manner to Example 58, Examples 59-92 in Table 1 (below) were made from commercially available aryl, heteroaryl or aliphatic carboxylic acids, or aryl, heteroaryl or aliphatic carbonyl chlorides on 0.05-0.5 mmol reaction scales.

In an analogous manner to Example 58, Examples 105-111 in Table 1 (below) were made from commercially available aryl, heteroaryl or aliphatic carboxylic acids, or aryl, heteroaryl or aliphatic carbonyl chlorides.

In an analogous manner to Example 58, Example 113 in Table 1 (below) was made from 4-trifluoromethyl-pyrimidine-2-carboxylic acid (Intermediate 11).

In a similar manner to Example 58, Example 93-104 in Table 1 (below) were made from Intermediate 3, N-(3-amino-adamantan-1-yl)-3-fluoro-benzamide, and commercially available heteroaryl carboxylic acids on 0.05-0.5 mmol reaction scales.

In a similar manner to Example 58, Example 182 and 184 were made from Intermediate 3, N-(3-amino-adamantan-1-yl)-3-fluoro-benzamide, and 4-methyl-pyrimidine-2-carboxylic acid (Intermediate 12) and 4-trifluoromethyl-pyrimidine-2-carboxylic acid (Intermediate 11), respectively.

In a similar manner to Example 58, Example 183 in Table 1 (below) was made from Intermediate 3, N-(3-amino-adamantan-1-yl)-3-fluoro-benzamide, and a commercially available heteroaryl carboxylic acid.

In a similar manner to Example 58, Examples 145-179 in Table 1 (below) were made from Intermediate 8,6-methyl-pyrazine-2-carboxylic acid (3-amino-adamantan-1-yl)-amide, and commercially available aryl or heteroaryl carboxylic acids, while Example 181 in Table 1 (below) was made from Intermediate 8 and 4-trifluoromethyl-pyrimidine-2-carboxylic acid (Intermediate 11).

In a similar manner to Example 58, Examples 185-188 in Table 1 (below) was made from Intermediate 7, pyrazine-2-carboxylic acid (3-amino-adamantan-1-yl)-amide, and commercially available heteroaryl carboxylic acids; Example 189 and was made from the Intermediate 7 and 4-methyl-pyrimidine-2-carboxylic acid (Intermediate 12).

In a similar manner to Example 58, Examples 191-193 in Table 1 (below) were made from Intermediate 10, 2-methyl-pyrimidine-4-carboxylic acid (3-amino-adamantan-1-yl)-amide, and commercially available 5-fluoro-pyridine-2-carboxylic acid (Beta Pharm, Inc., New Haven, Conn., USA), 4-trifluoromethyl-pyrimidine-2-carboxylic acid (Intermediate 11) or 4-methyl-pyrimidine-2-carboxylic acid (Intermediate 12).

In a similar manner to Example 58, Examples 194-196 in Table 1 (below) were made from Intermediate 9, pyrimidine-4-carboxylic acid (3-amino-adamantan-1-yl)-amide, and 4-methyl-pyrimidine-2-carboxylic acid (Intermediate 12), commercially available 5-fluoro-pyridine-2-carboxylic acid or 4-trifluoromethyl-pyrimidine-2-carboxylic acid (Intermediate 11).

Example 143

6-Methyl-pyridine-2-carboxylic acid {3-[(6-(1-hydroxy-ethyl)-pyridine-2-carbonyl)-amino]-adamantan-1-yl}-amide

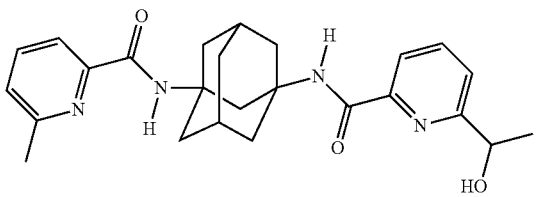

Example 143 in Table 1 (below) was made from Example 142 via NaBH₄ reduction, supra, as follows:

Into a vial containing 6-methyl-pyridine-2-carboxylic acid {3-[(6-acetyl-pyridine-2-carbonyl)-amino]-adamantan-1-yl}-amide (50 mg, 0.1 mmol, Example 142) in MeOH (2 mL) was added sodium borohydride (6 mg, 0.17 mmol) at 0° C. After stirring for 2 h, the reaction mixture was concentrated and partitioned into dichloromethane and saturated sodium bicarbonate. The organic layer was dried over sodium sulfate and concentrated under reduced pressure. The residue was purified on a RP-HPLC/MS purification system (Gradient: acetonitrile in water, 25-95%, in 3.6 min with a shallow gradient from 33-63% of acetonitrile between 0.75-3.3 min and a cycle time of 5 min. Flow rate: 100 mL/min. Mobile phase additive: 48 mM of ammonium formate. Column: Inertsil® C18, 30×50 mm, 5 um particle size) to afford 45 mg (90%) of the title compound, 6-methyl-pyridine-2-carboxylic acid {3-[(6-(1-hydroxy-ethyl)-pyridine-2-carbonyl)-amino]-adamantan-1-yl}-amide. $^1$H NMR (400 MHz, CDCl$_3$) δ 8.07-8.00 (m, 2H), 7.90 (d, J=7.9 Hz, 1H), 7.78 (t, J=7.9 Hz, 1H), 7.74 (s, b, 1H), 7.64 (t, J=7.8 Hz, 1H), 7.41 (d, J=7.8 Hz, 1H), 7.20-7.06 (m, 1H), 4.91-4.85 (m, 1H), 2.50 (s, b, 5H), 2.31-2.26 (m, 2H), 2.21-2.06 (m, 8H), 1.69-1.64 (m, 2H), 1.48 (s, 3H). ESI-MS m/z: 435.0 (M+H)⁺.

Example 144

6-Methyl-pyridine-2-carboxylic acid (3-{[6-(1-hydroxy-1-methyl-ethyl)-pyridine-2-carbonyl]-amino}-adamantan-1-yl)-amide

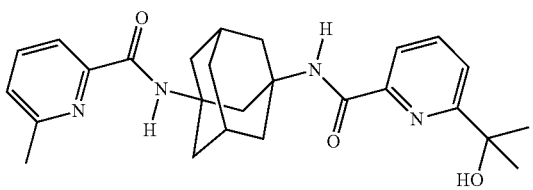

Example 144 in Table 1 (below) was made from Example 142 via Grignard reaction, supra, as follows:

Into a vial containing 6-methyl-pyridine-2-carboxylic acid {3-[(6-acetyl-pyridine-2-carbonyl)-amino]-adamantan-1-yl}-amide (35 mg, 0.08 mmol, Example 142) in THF (2 mL) was added 1M methyl lithium (0.4 mL) at −40° C. After stirring for 2 h, the reaction mixture was quenched with cold water, concentrated and partitioned into dichloromethane and saturated sodium bicarbonate. The organic layer was dried over sodium sulfate and concentrated under reduced pressure. The residue was purified on a RP-HPLC/MS purification system (Gradient: acetonitrile in water, 28-95%, in 3.6 min with a shallow gradient from 33-60% of acetonitrile between 0.75-3.4 min and a cycle time of 5 min. Flow rate: 100 mL/min. Mobile phase additive: 48 mM of ammonium formate. Column: Inertsil® C8, 30×50 mm, 5 um particle size) to afford 25 mg (69%) of the title compound, 6-methyl-pyridine-2-carboxylic acid (3-{[6-(1-hydroxy-1-methyl-ethyl)-pyridine-2-carbonyl]-amino}-adamantan-1-yl)-amide. $^1$H NMR (400 MHz, CDCl$_3$) δ 8.10-8.06 (m, 2H), 7.95 (d, J=7.6 Hz, 1H), 7.86 (t, J=7.8 Hz, 1H), 7.75 (s, 1H), 7.70 (t, J=7.8 Hz, 1H), 7.59 (d, J=7.9 Hz, 1H), 7.26-7.22 (m, 1H), 2.58-2.55 (m, 5H), 2.39-2.13 (m, 10H), 1.76-1.71 (m, 2H), 1.59 (s, 6H). ESI-MS m/z: 449.0 (M+H)+.

Example 180

2-Trifluoromethyl-pyrimidine-4-carboxylic acid {3-[(6-methyl-pyrazine-2-carbonyl)-amino]-adamantan-1-yl}-amide

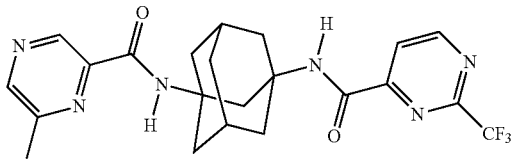

Example 180 in Table 1 (below) was made via the process of Scheme 3 from Intermediate 8 and 2-trifluoromethyl-pyrimidine-4-carboxylic acid, which was prepared from the corresponding ester, supra, as follows:

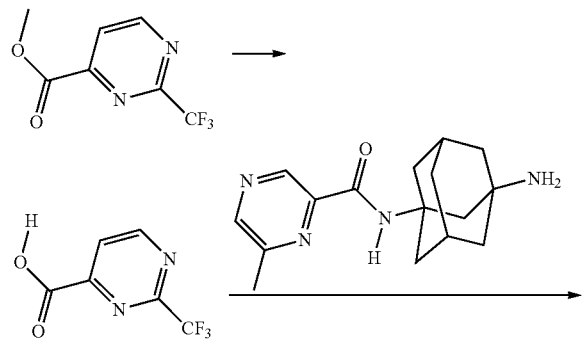

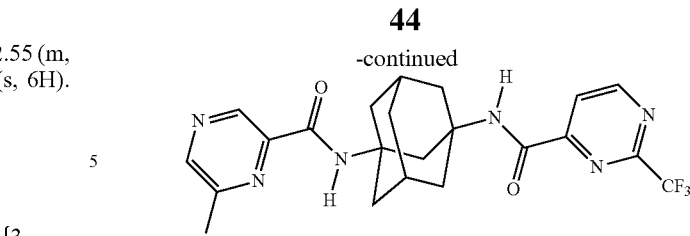

To a microwave vial was added 2-trifluoromethyl-pyrimidine-4-carboxylic acid methyl ester (110 mg, 0.52 mmol, CNH Tech, MA), THF (2 mL), and lithium hydroxide (18 mg, 0.75 mmol) in 200 µL of water. The mixture was heated in a microwave oven for 5 min at 100° C., and then concentrated to dryness under reduced pressure. To the residue was added Intermediate 8, 6-methyl-pyrazine-2-carboxylic acid (3-amino-adamantan-1-yl)-amide (100 mg, 0.4 mmol), THF (5 mL), DIEA (90 mg, 0.7 mmol) and TBTU (140 mg, 0.42 mmol, AKSCI, CA). After stirring at rt for 16 h, the reaction mixture was concentrated and partitioned into DCM and saturated sodium bicarbonate. The organic layer was separated, dried over sodium sulfate, filtered and concentrated to dryness under reduced pressure. The crude product was purified on a RP-HPLC/MS system (Gradient: acetonitrile in water, 30-95%, in 3.6 min with a cycle time of 5 min. with a shallow gradient from 40-68% of acetonitrile between 0.75-3.4 min. Flow rate: 100 mL/min. Mobile phase additive: 48 mM of ammonium formate. Column: Inertsil® C8, 30×50 mm, 5 um particle size) to give 60 mg (40%) of the title compound, 2-trifluoromethyl-pyrimidine-4-carboxylic acid {3-[(6-methyl-pyrazine-2-carbonyl)-amino]-adamantan-1-yl}-amide. 1H NMR (400 MHz, CDCl3) δ 9.16 (s, 1H), 9.12 (d, J=5.0, 1H), 8.6 (s, 1H), 8.28 (d, J=5.0, 1H), 7.80-7.75 (m, 2H), 2.6 (s, b, 5H), 2.42-2.36 (m, 2H), 2.23-2.17 (m, 8H), 1.77-1.73 (m, 2H). ESI-MS m/z: 460.9 (M+H)+.

In a similar manner to Example 180, Examples 112, 140 and 190 in Table 1 (below) were made from Intermediate 2, pyridine-2-carboxylic acid (3-amino-adamantan-1-yl)-amide, Intermediate 1, 6-methyl-pyridine-2-carboxylic acid (3-amino-adamantan-1-yl)-amide, and Intermediate 7, pyrazine-2-carboxylic acid (3-amino-adamantan-1-yl)-amide, respectively.

TABLE 1

| EXAMPLE | STRUCTURE | CHEMICAL NAME |
| --- | --- | --- |
| 1 | 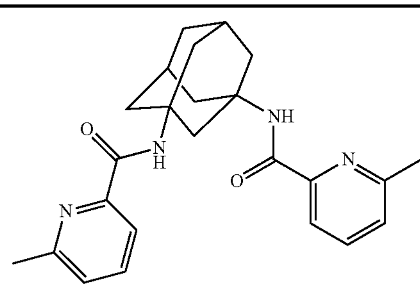 | N,N'-(1,3-adamantylene)bis(6-methyl-pyridine-2-carboxamide) |
| 2 | 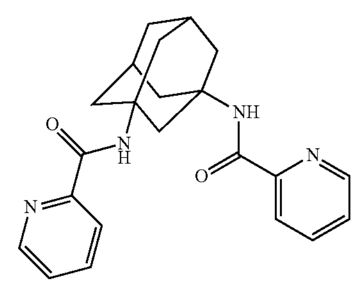 | N,N'-(1,3-adamantylene)bis(2-pyridinecarboxamide) |

TABLE 1-continued

| EXAMPLE | STRUCTURE | CHEMICAL NAME |
| --- | --- | --- |
| 3 | 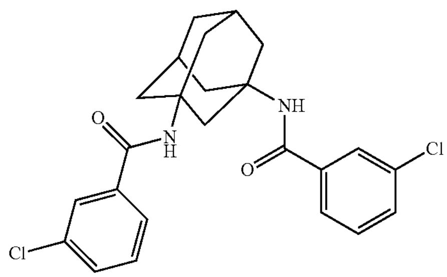 | N,N'-(1,3-adamantylene)bis(3-chloro-benzamide) |
| 4 | 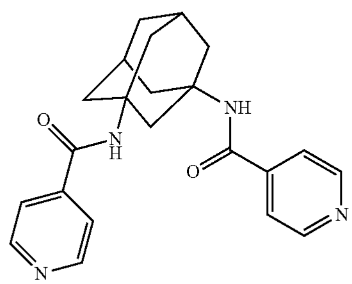 | N,N'-(1,3-adamantylene)bis(4-pyridinecarboxamide) |
| 5 | 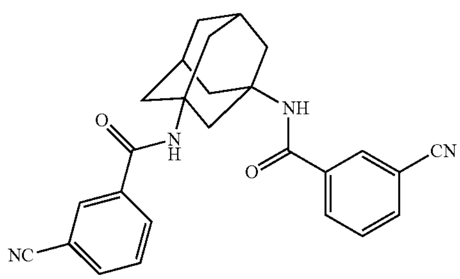 | N,N'-(1,3-adamantylene)bis(3-cyano-benzamide) |
| 6 | 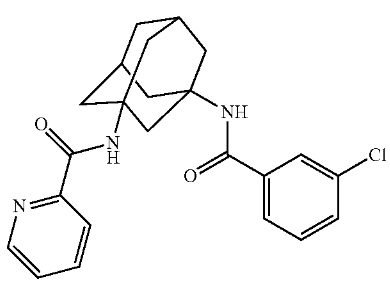 | Pyridine-2-carboxylic acid[3-(3-chloro-benzoylamino)-adamantan-1-yl]-amide |
| 7 | 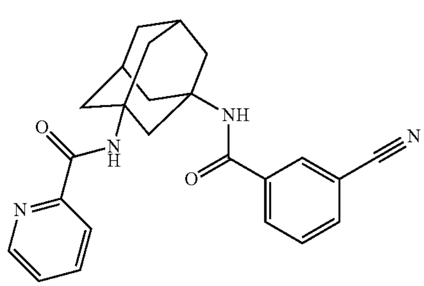 | Pyridine-2-carboxylic acid[3-(3-cyano-benzoylamino)-adamantan-1-yl]-amid |
| 8 | 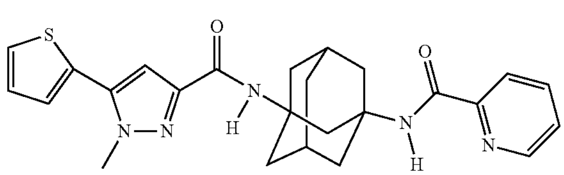 | Pyridine-2-carboxylic acid {3-[(1-methyl-5-thiophen-2-yl-1H-pyrazole-3-carbonyl)-amino]-adamantan-1-yl}-amide |

TABLE 1-continued

| EXAMPLE | STRUCTURE | CHEMICAL NAME |
|---|---|---|
| 9 | 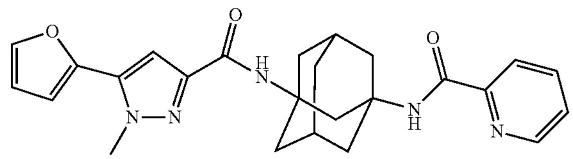 | Pyridine-2-carboxylic acid {3-[(5-furan-2-yl-1-methyl-1H-pyrazole-3-carbonyl)-amino]-adamantan-1-yl}-amide |
| 10 | 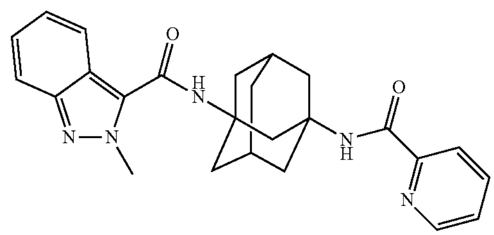 | 2-Methyl-2H-indazole-3-carboxylic acid {3-[(pyridine-2-carbonyl)-amino]-adamantan-1-yl}-amide |
| 11 | 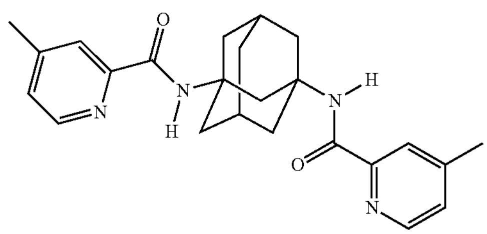 | N,N'-(1,3-adamantylene)bis(4-methyl-pyridine-2-carboxamide) |
| 12 | 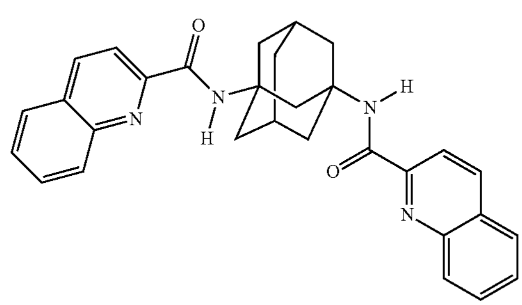 | N,N'-(1,3-adamantylene)bis(quinoline-2-carboxamide) |
| 13 | 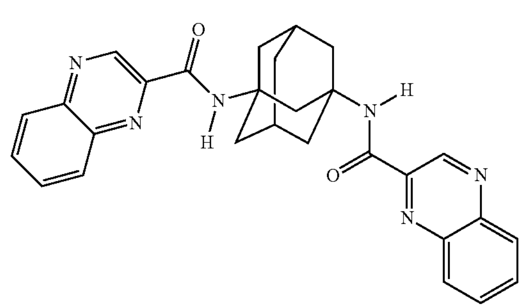 | N,N'-(1,3-adamantylene)bis(quinoxaline-2-carboxamide |
| 14 | 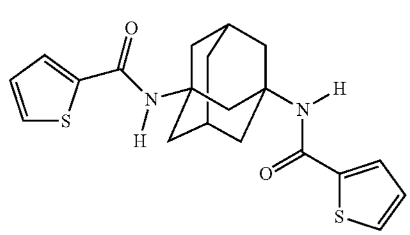 | N,N'-(1,3-adamantylene)bis(thiophene-2-carboxamide) |

TABLE 1-continued

| EXAMPLE | STRUCTURE | CHEMICAL NAME |
|---|---|---|
| 15 | 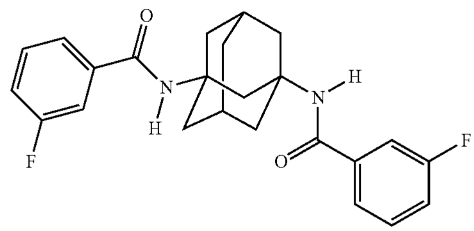 | N,N'-(1,3-adamantylene)bis(3-fluorobenzamide) |
| 16 | 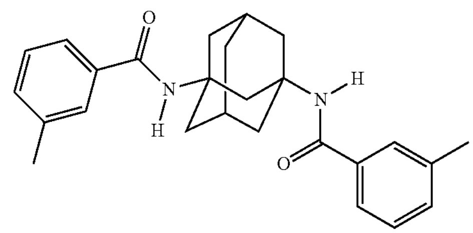 | N,N'-(1,3-adamantylene)bis(3-methylbenzamide) |
| 17 | 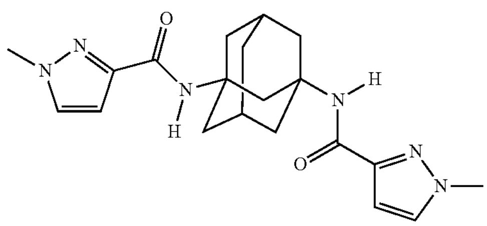 | N,N'-(1,3-adamantylene)bis(1-methyl-1H-pyrazole-3-carboxamide) |
| 18 | 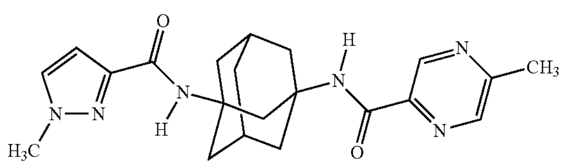 | 5-Methyl-pyrazine-2-carboxylic acid {3-[(1-methyl-1H-pyrazole-3-carbonyl)-amino]-adamantan-1-yl}-amide |
| 19 | 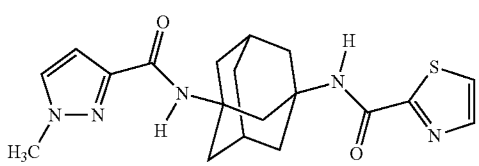 | Thiazole-2-carboxylic acid {3-[(1-methyl-1H-pyrazole-3-carbonyl)-amino]-adamantan-1-yl}-amide |
| 20 | 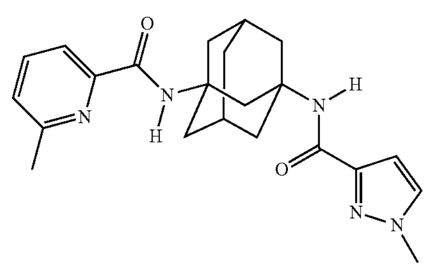 | 6-Methyl-pyridine-2-carboxylic acid {3-[(1-methyl-1H-pyrazole-3-carbonyl)-amino]-adamantan-1-yl}-amide |
| 21 | 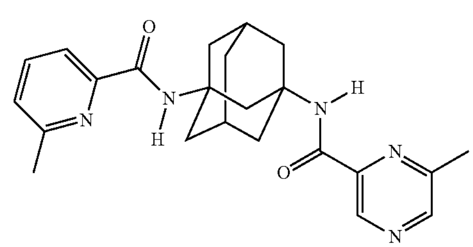 | 6-Methyl-pyrazine-2-carboxylic acid {3-[(6-methyl-pyridine-2-carbonyl)-amino]-adamantan-1-yl}-amide |

TABLE 1-continued

| EXAMPLE | STRUCTURE | CHEMICAL NAME |
|---|---|---|
| 22 | 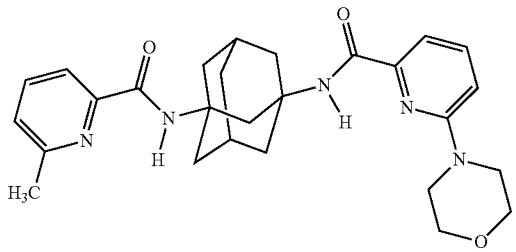 | 6-Morpholin-4-yl-pyridine-2-carboxylic acid-{3-[(6-methyl-pyridine-2-carbonyl)-amino]-adamantan-1-yl}-amide |
| 23 | 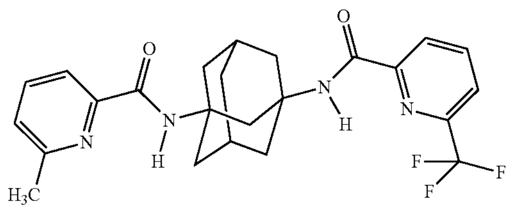 | 6-Trifluoromethyl-pyridine-2-carboxylic acid {3-[(6-methyl-pyridine-2-carobnyl)-amino]-adamantan-1-yl}-amide |
| 24 | 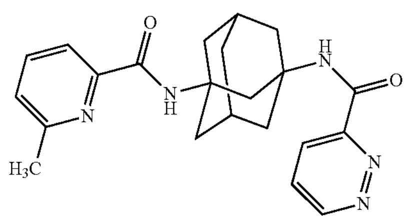 | Pyridazine-3-carboxylic acid {3-[(6-methyl-pyridine-2-carbonyl)-amino]-adamantan-1-yl}-amide |
| 25 | 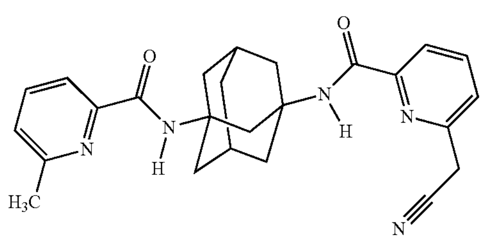 | 6-Cyanomethyl-pyridine-2-carboxylic acid {3-[(6-methyl-pyridine-2-carbonyl)-amino]-adamantan-1-yl}-amide |
| 26 | 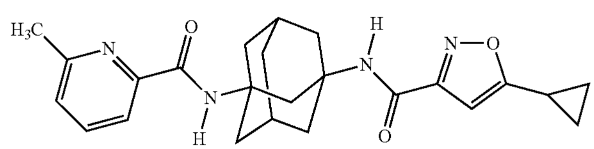 | 6-Methyl-pyridine-2-carboxylic acid {3-[(5-cyclopropyl-isoxazole-3-carbonyl)-amino]-adamantan-1-yl}-amide |
| 27 | 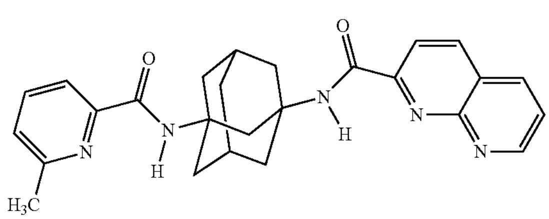 | [1,8]Naphthyridine-2-carboxylic acid {3-[(6-methyl-pyridine-2-carbonyl)-amino]-adamantan-1-yl}-amide |
| 28 | 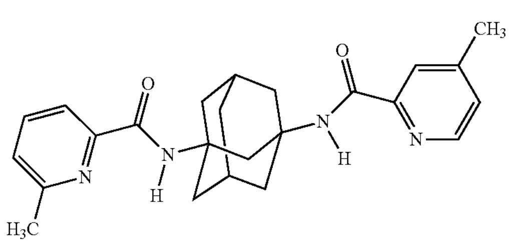 | 4-Methyl-pyridine-2-carboxylic acid {3-[(6-methyl-pyridine-2-carbonyl)-amino]-adamantan-1-yl}-amide |

TABLE 1-continued

| EXAMPLE | STRUCTURE | CHEMICAL NAME |
|---|---|---|
| 29 | 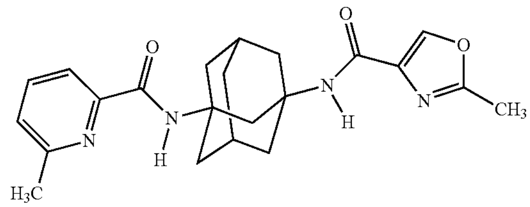 | 6-Methyl-pyridine-2-carboxylic acid {3-[(2-methyl-oxazole-4-carbonyl)-amino]-adamantan-1-yl}-amide |
| 30 | 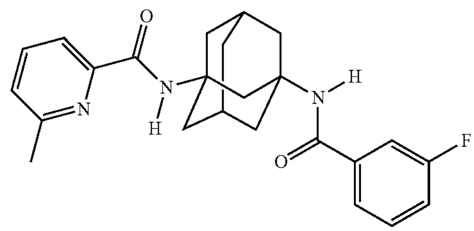 | 6-Methyl-pyridine-2-carboxylic acid [3-(3-fluoro-benzoylamino)-adamantan-1-yl]-amide |
| 31 | 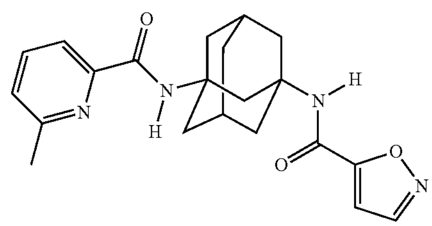 | 6-Methyl-pyridine-2-carboxylic acid {3-[(isoxazole-5-carbonyl)-amino]-adamantan-1-yl}-amide |
| 32 | 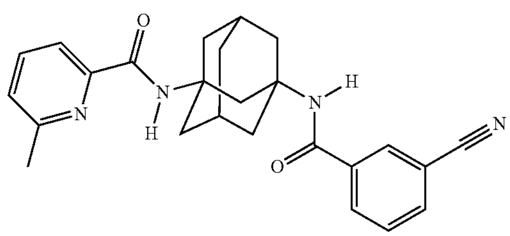 | 6-Methyl-pyridine-2-carboxylic acid [3-(3-cyano-benzoylamino)-adamantan-1-yl]-amide |
| 33 | 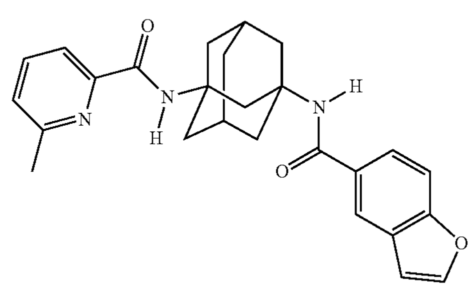 | 6-Methyl-pyridine-2-carboxylic acid {3-[(benzofuran-5-carbonyl)-amino]-adamantan-1-yl}-amide |
| 34 | 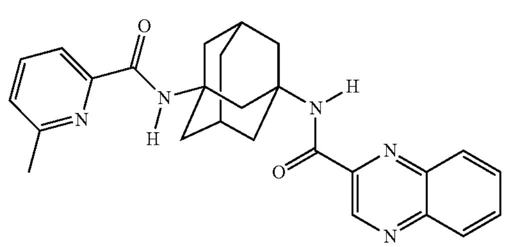 | Quinoxaline-2-carboxylic acid {3-[(6-methyl-pyridine-2-carbonyl)-amino]-adamantan-1-yl}-amide |

TABLE 1-continued

| EXAMPLE | STRUCTURE | CHEMICAL NAME |
|---|---|---|
| 35 | 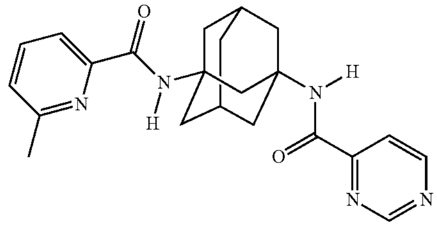 | Pyrimidine-4-carboxylic acid {3-[(6-methyl-pyridine-2-carbonyl)-amino]-adamantan-1-yl}-amide |
| 36 | 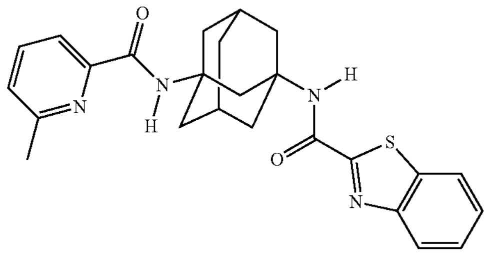 | Benzothiazole-2-carboxylic acid {3-[(6-methyl-pyridine-2-carbonyl)-amino]-adamantan-1-yl}-amide |
| 37 | 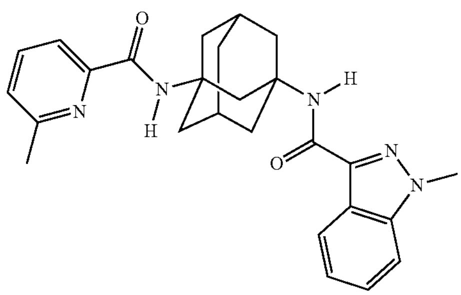 | 1-Methyl-1H-indazole-3-carboxylic acid {3-[(6-methyl-pyridine-2-carbonyl)-amino]-adamantan-1-yl}-amide |
| 38 | 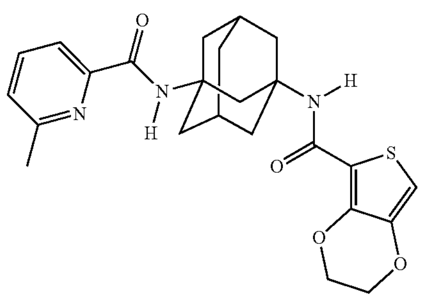 | 6-Methyl-pyridine-2-carboxylic acid {3-[(2,3-dihydro-thieno[3,4-b][1,4]dioxine-5-carbonyl)-amino]-adamantan-1-yl}-amide |
| 39 | 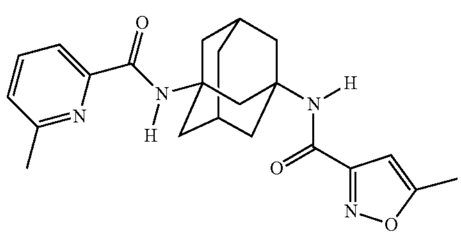 | 6-Methyl-pyridine-2-carboxylic acid {3-[(5-methyl-isoxazole-3-carbonyl)-amino]-adamantan-1-yl}-amide |
| 40 | 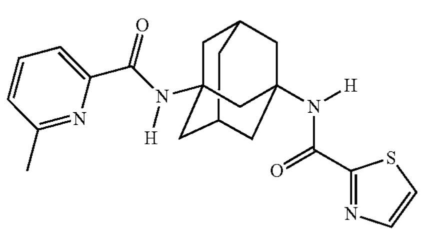 | 6-Methyl-pyridine-2-carboxylic acid {3-[(thiazole-2-carbonyl)-amino]-adamantan-1-yl}-amide |

| EXAMPLE | STRUCTURE | CHEMICAL NAME |
|---|---|---|
| 41 | 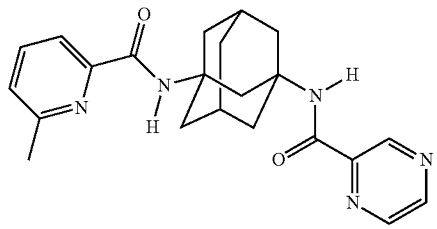 | Pyrazine-2-carboxylic acid {3-[(6-methyl-pyridine-2-carbonyl)-amino]-adamantan-1-yl}-amide |
| 42 | 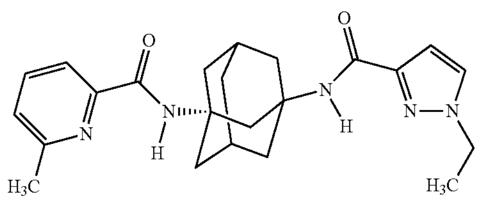 | 6-Methyl-pyridine-2-carboxylic acid {3-[(1-ethyl-1H-pyrazole-3-carbonyl)-amino]-adamantan-1-yl}-amide |
| 43 | 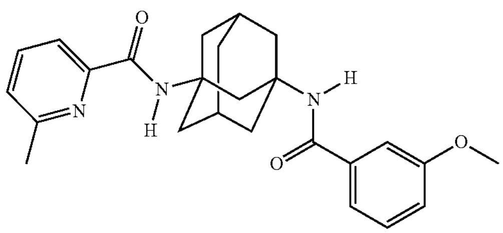 | 6-Methyl-pyridine-2-carboxylic acid [3-(3-methoxy-benzoylamino)-adamantan-1-yl]-amide |
| 44 | 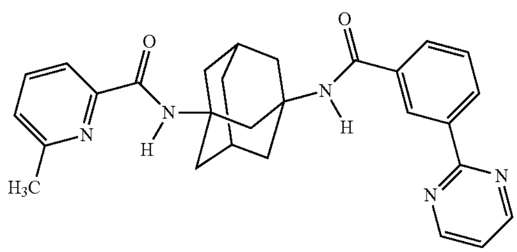 | 6-Methyl-pyridine-2-carboxylic acid [3-(3-pyrimidin-2-yl-benzoylamino)-adamantan-1-yl]-amide |
| 45 | 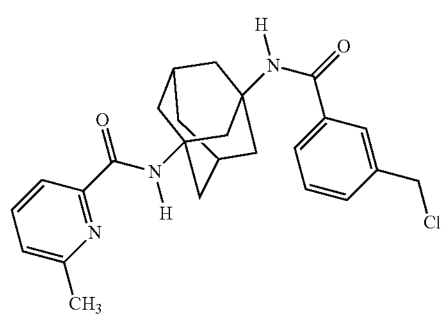 | 6-Methyl-pyridine-2-carboxylic acid [3-(3-chloromethyl-benzoylamino)-adamantan-1-yl]-amide |
| 46 | 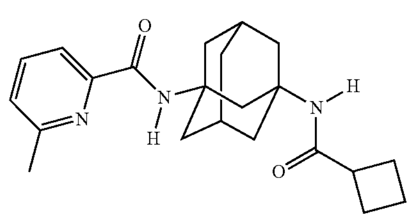 | 6-Methyl-pyridine-2-carboxylic acid [3-(cyclobutanecarbonyl-amino)-adamantan-1-yl]-amide |

| EXAMPLE | STRUCTURE | CHEMICAL NAME |
|---|---|---|
| 47 | 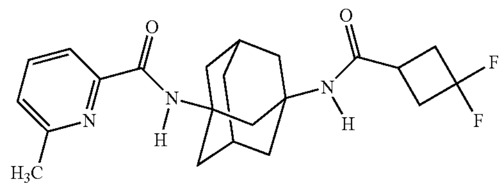 | 6-Methyl-pyridine-2-carboxylic acid {3-[(3,3-difluoro-cyclobutanecarbonyl)-amino]-adamantan-1-yl}-amide |
| 48 | 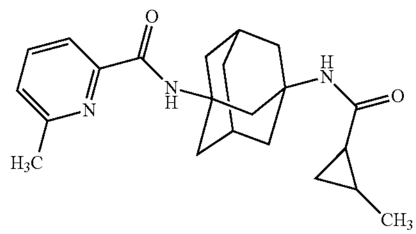 | 6-Methyl-pyriidne-2-carboxylic acid {3-[(2-methyl-cyclopropanecarbonyl)-amino]-adamantan-1-yl}-amide |
| 49 | 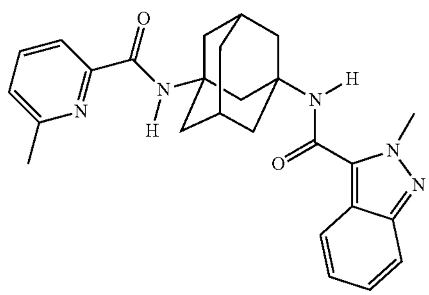 | 2-Methyl-2H-indazole-3-carboxylic acid {3-[(6-methyl-pyridine-2-carbonyl)-amino]-adamantan-1-yl}-amide |
| 50 | 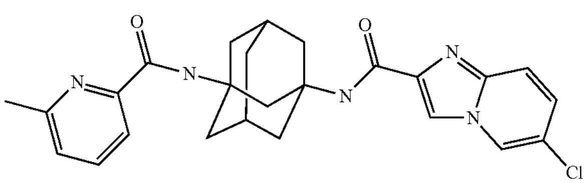 | 6-Chloro-imidazo[1,2-a]pyridine-2-carboxylic acid {3-[(6-methyl-pyridine-2-carbonyl)-amino]-adamantan-1-yl}-amide |
| 51 | 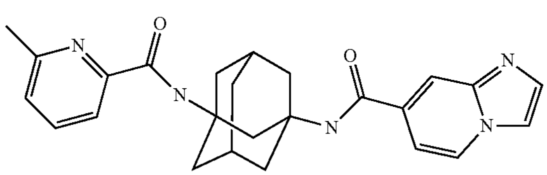 | Imidazo[1,2-a]pyridine-7-carboxylic acid {3-[(6-methyl-pyridine-2-carbonyl)-amino]-adamantan-1-yl}-amide |
| 52 | 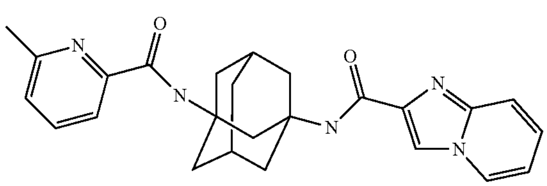 | Imidazo[1,2-a]pyridine-2-carboxylic acid {3-[(6-methyl-pyridine-2-carbonyl)-amino]-adamantan-1-yl}-amide |
| 53 | 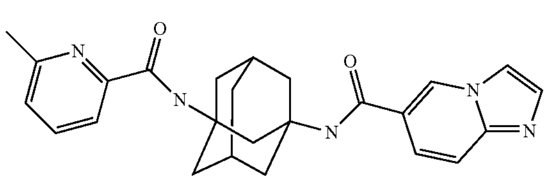 | Imidazo[1,2-a]pyridine-6-carboxylic acid {3-[(6-methyl-pyridine-2-carbonyl)-amino]-adamantan-1-yl}-amide |

| EXAMPLE | STRUCTURE | CHEMICAL NAME |
|---|---|---|
| 54 | 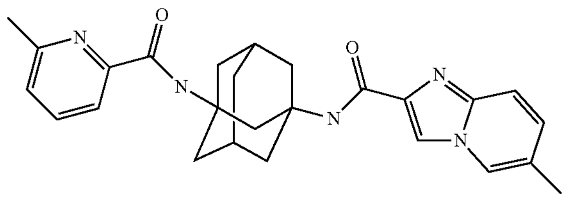 | 6-Methyl-imidazo[1,2-a]pyridine-2-carboxylic acid {3-[(6-methyl-pyridine-2-carbonyl)-amino]-adamantan-1-yl}-amide |
| 55 | 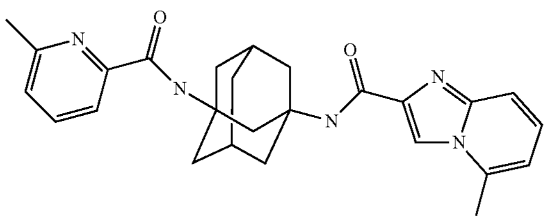 | 5-Methyl-imidazo[1,2-a]pyridine-2-carboxylic acid {3-[(6-methyl-pyridine-2-carbonyl)-amino]-adamantan-1-yl}-amide |
| 56 | 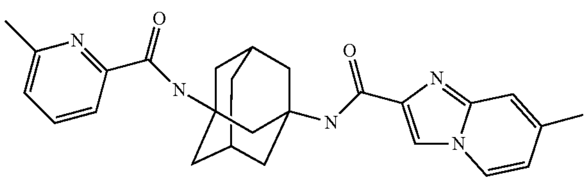 | 7-Methyl-imidazo[1,2-a]pyridine-2-carboxylic acid {3-[(6-methyl-pyridine-2-carbonyl)-amino]-adamantan-1-yl}-amide |
| 57 | 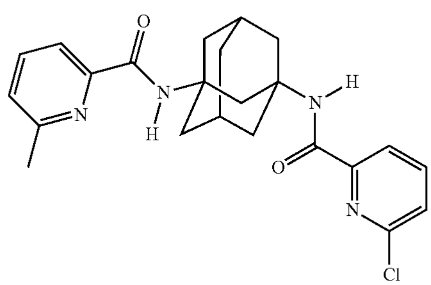 | 6-Chloro-pyridine-2-carboxylic acid {3-[(6-methyl-pyridine-2-carbonyl)-amino]-adamantan-1-yl}-amide |
| 58 | 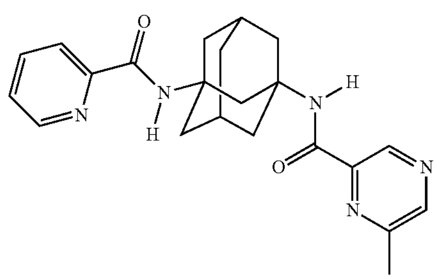 | 6-Methyl-pyrazine-2-carboxylic acid {3-[(pyridine-2-carbonyl)-amino]-adamantan-1-yl}-amide |
| 59 | 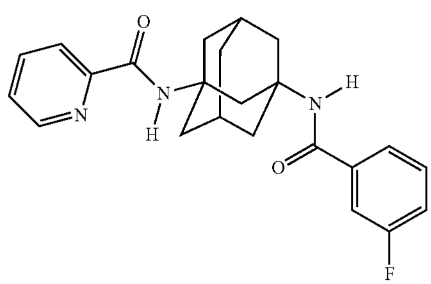 | Pyridine-2-carboxylic acid [3-(3-fluoro-benzoylamino)-adamantan-1-yl]-amide |

TABLE 1-continued

| EXAMPLE | STRUCTURE | CHEMICAL NAME |
|---|---|---|
| 60 | 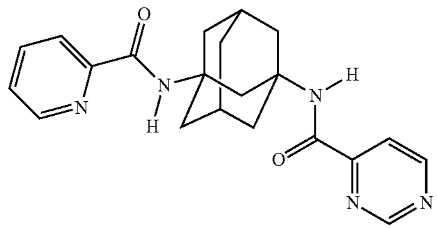 | Pyrimidine-4-carboxylic acid {3-[(pyridine-2-carbonyl)-amino]-adamantan-1-yl}-amide |
| 61 | 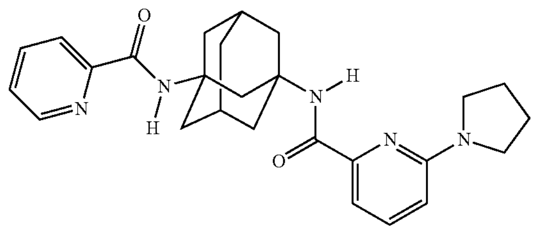 | 6-Pyrrolidin-1-yl-pyridine-2-carboxylic acid {3-[(pyridine-2-carbonyl)-amino]-adamantan-1-yl}-amide |
| 62 | 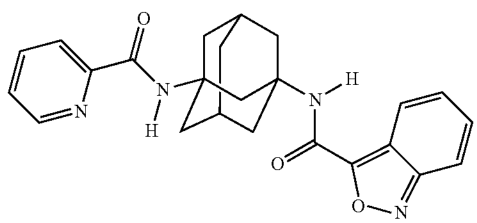 | Benzo[c]isoxazole-3-carboxylic acid {3-[(pyridine-2-carbonyl)-amino]-adamantan-1-yl}-amide |
| 63 | 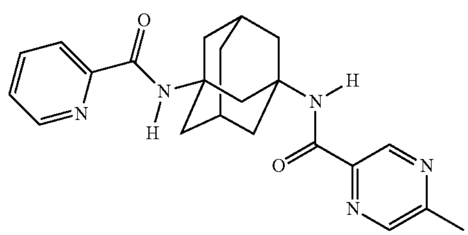 | 5-Methyl-pyrazine-2-carboxylic acid {3-[(pyridine-2-carbonyl)-amino]-adamantan-1-yl}-amide |
| 64 | 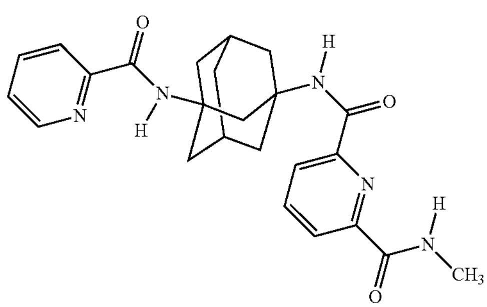 | Pyridine-2,6-dicarboxylic acid 2-methylamide 6-({3-[(pyridine-2-carbonyl)-amino]-adamantan-1-yl}-amide) |
| 65 | 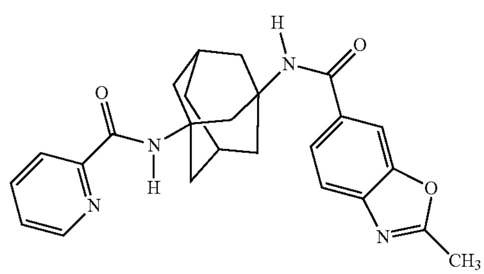 | 2-Methyl-benzoxazole-6-carboxylic acid {3-[(pyridine-2-carbonyl)-amino]-adamantan-1-yl}-amide |

TABLE 1-continued

| EXAMPLE | STRUCTURE | CHEMICAL NAME |
| --- | --- | --- |
| 66 | 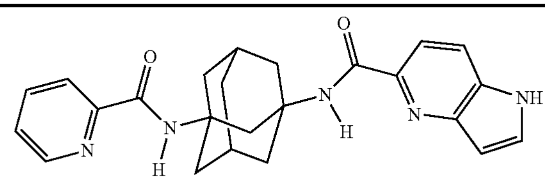 | 1H-Pyrrolo[3,2-b]pyridine-5-carboxylic acid {3-[(pyridine-2-carbonyl)-amino]-adamantan-1-yl}-amide |
| 67 | 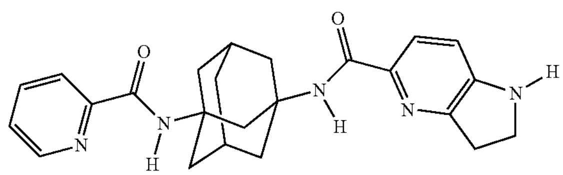 | 2,3-Dihydro-1H-indole-5-carboxylic acid {3-[(pyridine-2-carbonyl)-amino]-adamantan-1-yl}-amide |
| 68 | 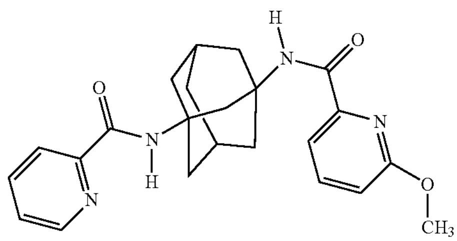 | 6-Methoxy-pyridine-2-carboxylic acid {3-[(pyridine-2-carbonyl)-amino]-adamantan-1-yl}-amide |
| 69 | 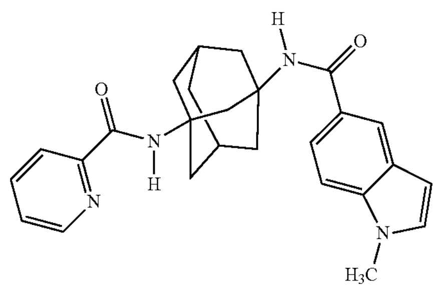 | 1-Methyl-1H-indole-5-carboxylic acid {3-[(pyridine-2-carbonyl)-amino]-adamantan-1-yl}-amide |
| 70 | 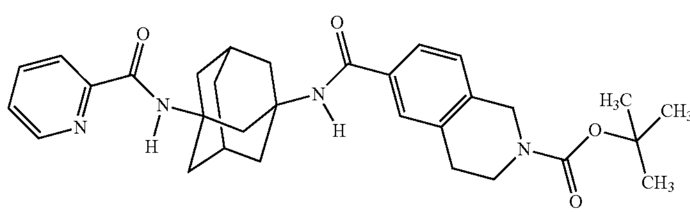 | 6-{3-[(Pyridine-2-carbonyl)-amino]-adamantan-1-yl-carbamoyl}-3,4-dihydro-1H-isoquinoline-2-carboxylic acid tert-butyl ester |
| 71 | 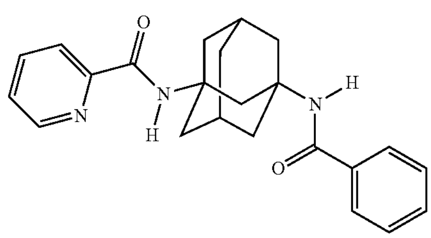 | Pyridine-2-carboxylic acid (3-benzoylamino-adamantan-1-yl)-amide |
| 72 | 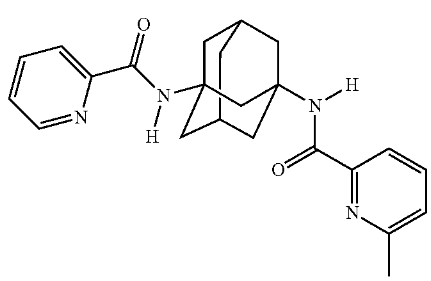 | 6-Methyl-pyridine-2-carboxylic acid {3-[(pyridine-2-carbonyl)-amino]-adamantan-1-yl}-amide |

TABLE 1-continued

| EXAMPLE | STRUCTURE | CHEMICAL NAME |
| --- | --- | --- |
| 73 | 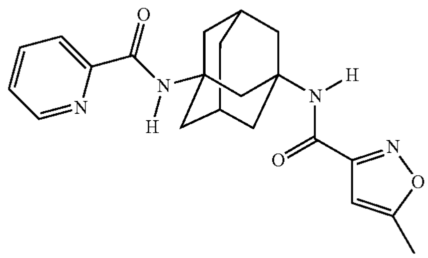 | Pyridine-2-carboxylic acid {3-[(5-methyl-isoxazole-3-carbonyl)-amino]-adamantan-1-yl}-amide |
| 74 | 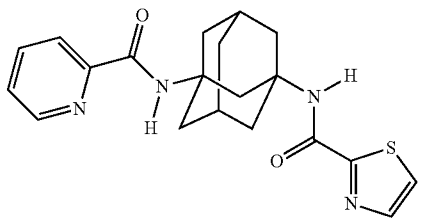 | Pyridine-2-carboxylic acid {3-[(thiazole-2-carbonyl)-amino]-adamantan-1-yl}-amide |
| 75 | 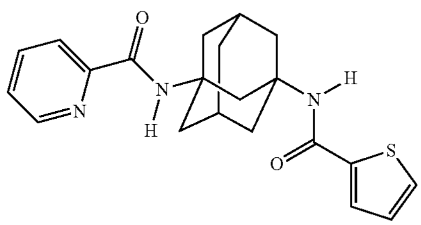 | Pyridine-2-carboxylic acid {3-[(thiophene-2-carbonyl)-amino]-adamantan-1-yl}-amide |
| 76 | 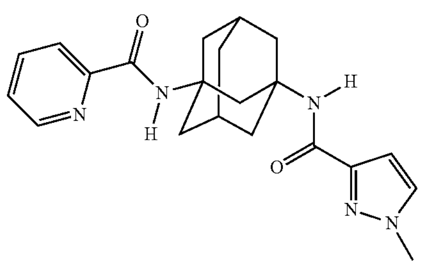 | Pyridine-2-carboxylic acid {3-[(1-methyl-1H-pyrazole-3-carbonyl)-amino]-adamantan-1-yl}-amide |
| 77 | 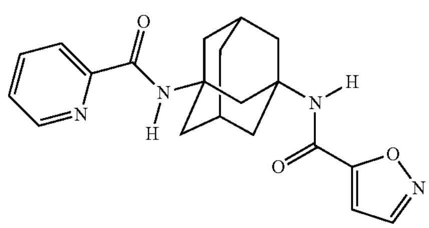 | Pyridine-2-carboxylic acid {3-[(isoxazole-5-carbonyl)-amino]-adamantan-1-yl}-amide |
| 78 | 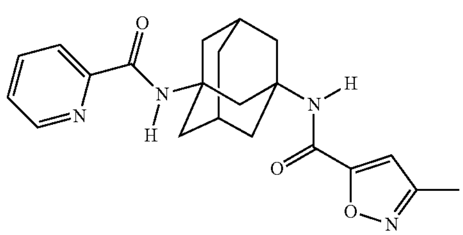 | Pyridine-2-carboxylic acid {3-[(3-methyl-isoxazole-5-carbonyl)-amino]-adamantan-1-yl}-amide |

TABLE 1-continued

| EXAMPLE | STRUCTURE | CHEMICAL NAME |
| --- | --- | --- |
| 79 | 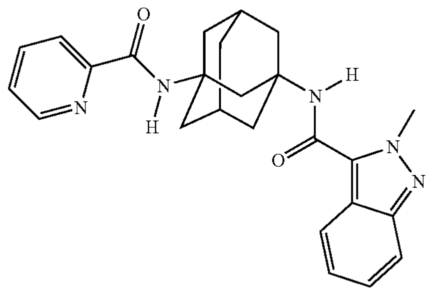 | 2-Methyl-2H-indazole-3-carboxylic acid {3-[(pyridine-2-carbonyl)-amino]-adamantan-1-yl}-amide |
| 80 | 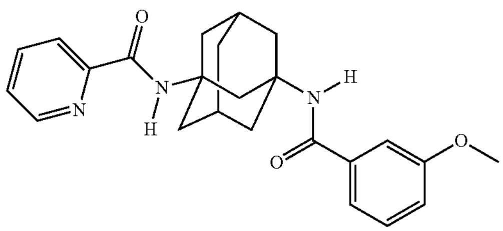 | Pyridine-2-carboxylic acid [3-(3-methoxy-benzoylamino)-adamantan-1-yl]-amide |
| 81 | 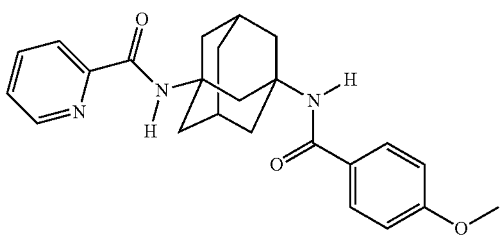 | Pyridine-2-carboxylic acid [3-(4-methoxy-benzoylamino)-adamantan-1-yl]-amide |
| 82 | 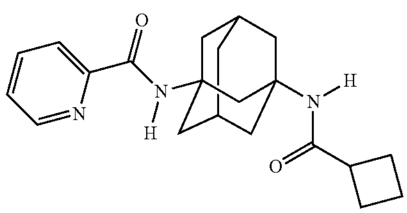 | Pyridine-2-carboxylic acid [3-(cyclobutanecarbonyl-amino)-adamantan-1-yl]-amide |
| 83 | 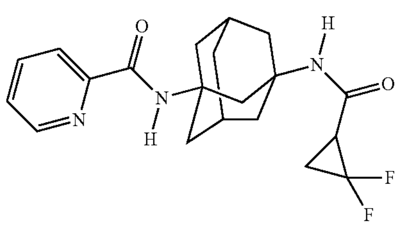 | Pyridine-2-carboxylic acid {3-[(2,2-difluoro-cyclopropanecarbonyl)-amino]-adamantan-1-yl}-amide |
| 84 | 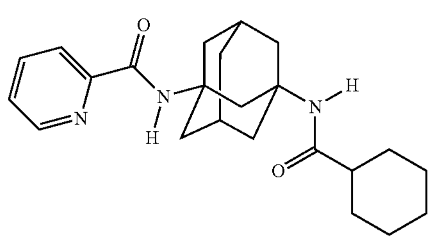 | Pyridine-2-carboxylic acid [3-(cyclohexanecarbonyl-amino)-adamantan-1-yl]-amide |

TABLE 1-continued

| EXAMPLE | STRUCTURE | CHEMICAL NAME |
|---|---|---|
| 85 | 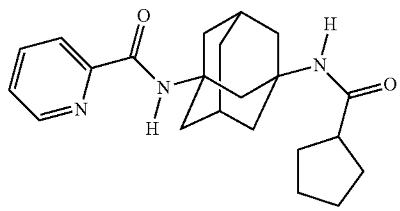 | Pyridine-2-carboxylic acid [3-(cyclopentanecarbonyl-amino)-adamantan-1-yl]-amide |
| 86 | 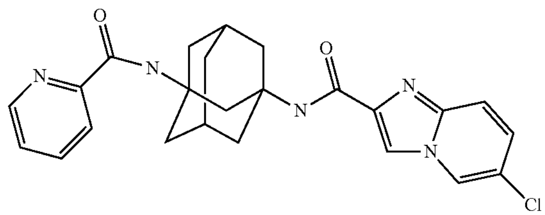 | 6-Cloro-imidazo[1,2-a]pyridine-2-carboxylic acid {3-[(pyridine-2-carbonyl)-amino]-adamantan-1-yl}-amide |
| 87 | 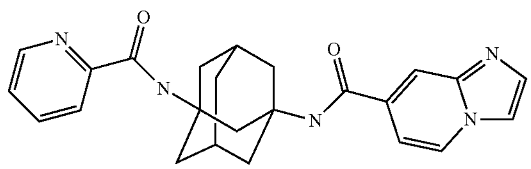 | Imidazo[1,2-a]pyridine-7-carboxylic acid {3-[(pyridine-2-carbonyl)-amino]-adamantan-1-yl}-amide |
| 88 | 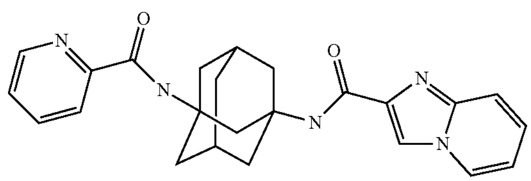 | Imidazo[1,2-a]pyridine-2-carboxylic acid {3-[(pyridine-2-carbonyl)-amino]-adamantan-1-yl}-amide |
| 89 | 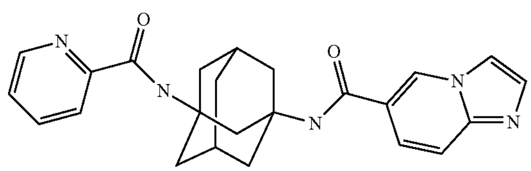 | Imidazo[1,2-a]pyridine-6-carboxylic acid {3-[(pyridine-2-carbonyl)-amino]-adamantan-1-yl}-amide |
| 90 | 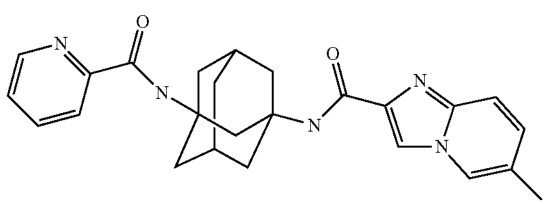 | 6-Methyl-imidazo[1,2-a]pyridine-2-carboxylic acid {3-[(pyridine-2-carbonyl)-amino]-adamantan-1-yl}-amide |
| 91 | 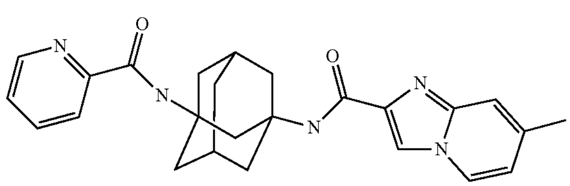 | 7-Methyl-imidazo[1,2-a]pyridine-2-carboxylic acid {3-[(pyridine-2-carbonyl)-amino]-adamantan-1-yl}-amide |
| 92 | 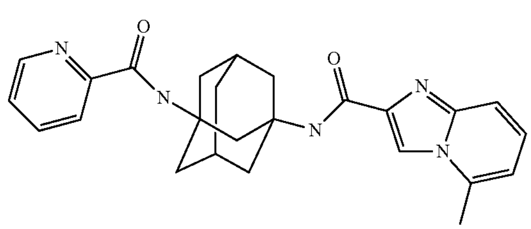 | 5-Methyl-imidazo[1,2-a]pyridine-2-carboxylic acid {3-[(pyridine-2-carbonyl)-amino]-adamantan-1-yl}-amide |

TABLE 1-continued

| EXAMPLE | STRUCTURE | CHEMICAL NAME |
|---|---|---|
| 93 | 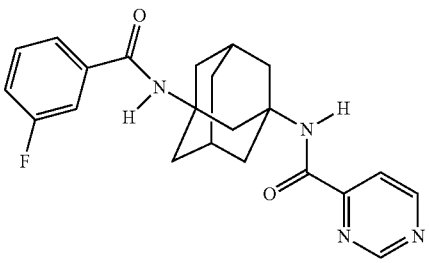 | Pyrimidine-4-carboxylic acid [3-(3-fluoro-benzoylamino)-adamantan-1-yl]-amide |
| 94 | 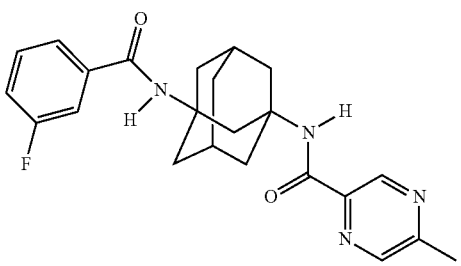 | 5-Methyl-pyrazine-2-carboxylic acid [3-(3-fluoro-benzoylamino)-adamantan-1-yl]-amide |
| 95 | 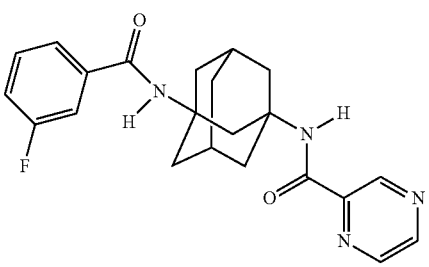 | Pyrazine-2-carboxylic acid [3-(3-fluoro-benzoylamino)-adamantan-1-yl]-amide |
| 96 | 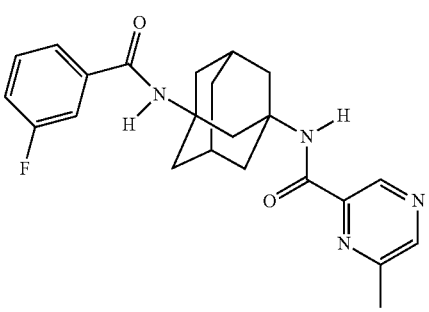 | 6-Methyl-pyrazine-2-carboxylic acid [3-(3-fluoro-benzoylamino)-adamantan-1-yl]-amide |
| 97 | 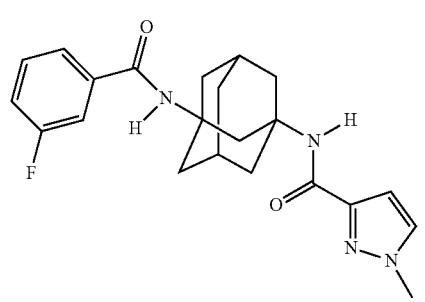 | 1-Methyl-1H-pyrazole-3-carboxylic acid [3-(3-fluoro-benzoylamino)-adamantan-1-yl]-amide |
| 98 | 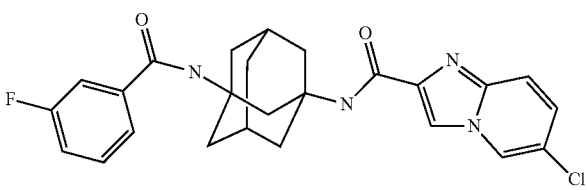 | 6-Chloro-imidazo[1,2-a]pyridine-2-carboxylic acid [3-(3-fluoro-benzoylamino)-adamantan-1-yl]-amide |

TABLE 1-continued

| EXAMPLE | STRUCTURE | CHEMICAL NAME |
| --- | --- | --- |
| 99 | 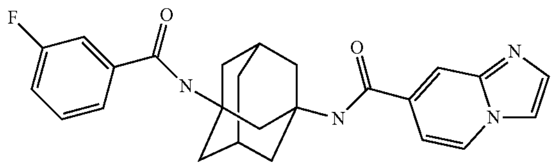 | Imidazo[1,2-a]pyridine-7-carboxylic acid [3-(3-fluoro-benzoylamino)-adamantan-1-yl]-amide |
| 100 | 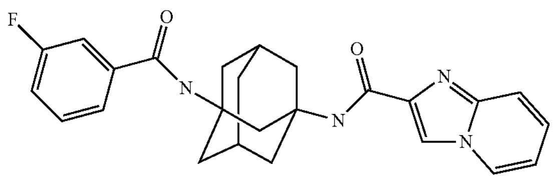 | Imidazo[1,2-a]pyridine-2-carboxylic acid [3-(3-fluoro-benzoylamino)-adamantan-1-yl]-amide |
| 101 | 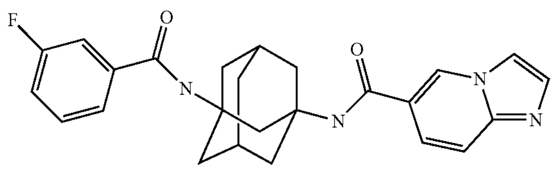 | Imidazo[1,2-a]pyridine-6-carboxylic acid [3-(3-fluoro-benzoylamino)-adamantan-1-yl]-amide |
| 102 | 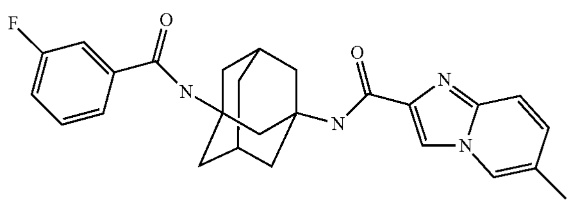 | 6-Methyl-imidazo[1,2-a]pyridine-2-carboxylic acid [3-(3-fluoro-benzoylamino)-adamantan-1-yl]-amide |
| 103 | 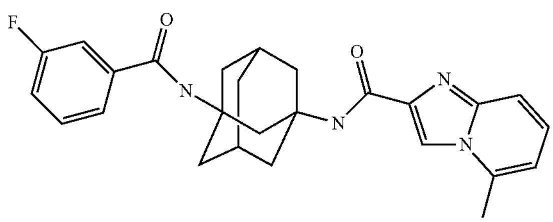 | 5-Methyl-imidazo[1,2-a]pyridine-2-carboxylic acid [3-(3-fluoro-benzoylamino)-adamantan-1-yl]-amide |
| 104 | 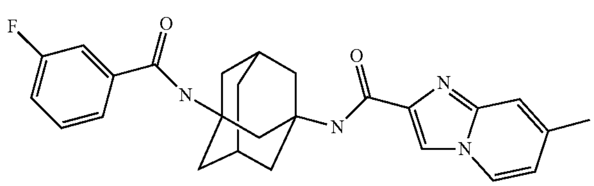 | 7-Methyl-imidazo[1,2-a]pyridine-2-carboxylic acid [3-(3-fluoro-benzoylamino)-adamantan-1-yl]-amide |
| 105 | 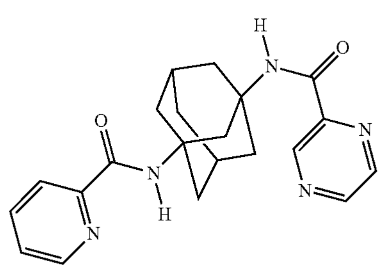 | Pyrazine-2-carboxylic acid {3-[(pyridine-2-carbonyl)-amino]-adamantan-1-yl}-amide |

TABLE 1-continued

| EXAMPLE | STRUCTURE | CHEMICAL NAME |
| --- | --- | --- |
| 106 | 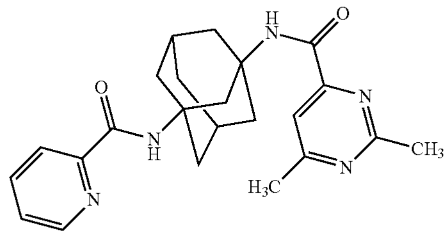 | 2,6-Dimethyl-pyrimidine-4-carboxylic acid {3-[(pyridine-2-carbonyl)-amino]-adamantan-1-yl}-amide |
| 107 | 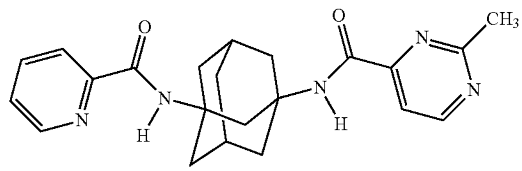 | 2-Methyl-pyrimidine-4-carboxylic acid {3-[(pyridine-2-carbonyl)-amino]-adamantan-1-yl}-amide |
| 108 | 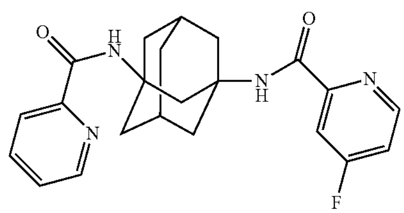 | 4-Fluoro-pyridine-2-carboxylic acid{3-[(pyridine-2-carbonyl)-amino]-adamantan-1-yl}-amide |
| 109 | 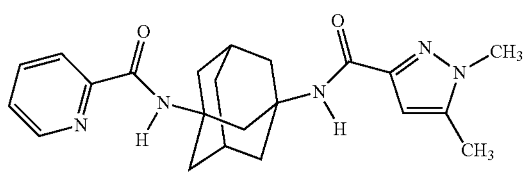 | Pyridine-2-carboxylic acid {3-[(1,5-dimethyl-1H-pyrazole-3-carbonyl)-amino]-adamantan-1-yl}-amide |
| 110 | 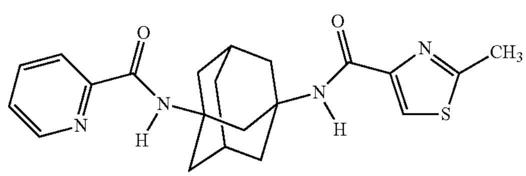 | Pyridine-2-carboxylic acid {3-[(2-methyl-thiazole-4-carbonyl)-amino]-adamantan-1-yl}-amide |
| 111 | 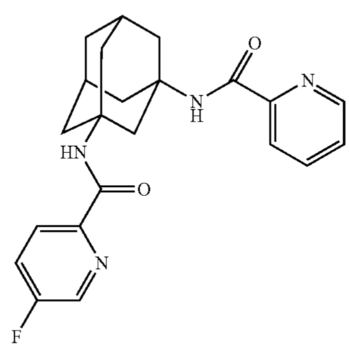 | 5-Fluoro-pyridine-2-carboxylic acid {3-[(pyridine-2-carbonyl)-amino]-adamantan-1-yl}-amide |
| 112 | 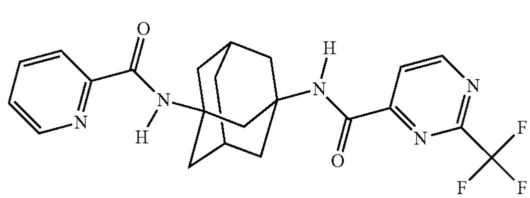 | 2-Trifluoromethyl-pyrimidine-4-carboxylic acid {3-[(pyridine-2-carbonyl)-amino]-adamantan-1-yl}-amide |

TABLE 1-continued

| EXAMPLE | STRUCTURE | CHEMICAL NAME |
|---|---|---|
| 113 | 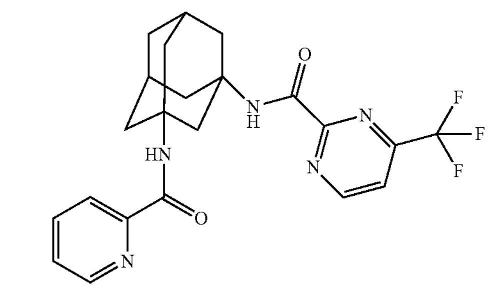 | 4-Trifluoromethyl-pyrimidine-2-carboxylic acid {3-[(pyridine-2-carbonyl)-amino]-adamantan-1-yl}-amide |
| 114 | 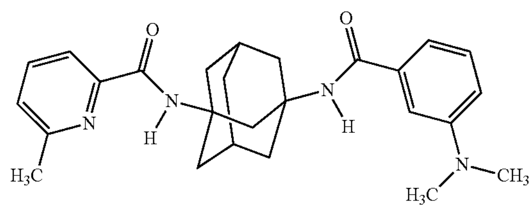 | 6-Methyl-pyridine-2-carboxylic acid[3-(3-dimethylamino-benzoylamino)-adamantan-1-yl]-amide |
| 115 | 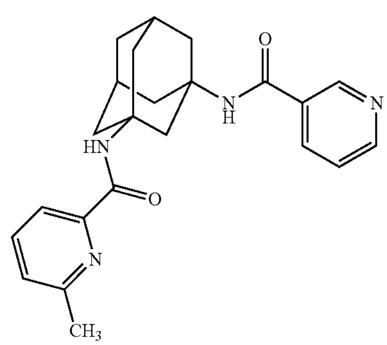 | 6-Methyl-pyridine-2-carboxylic acid {3-[(pyridine-3-carbonyl)-amino]-adamantan-1-yl}-amide |
| 116 | 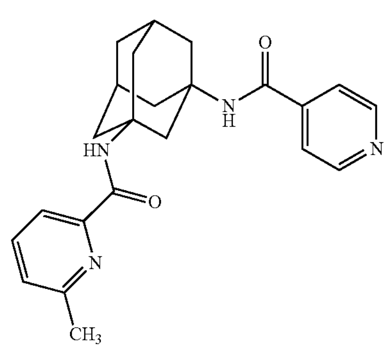 | 6-Methyl-pyridine-2-carboxylic acid {3-[(pyridine-4-carbonyl)-amino]-adamantan-1-yl}-amide |
| 117 | 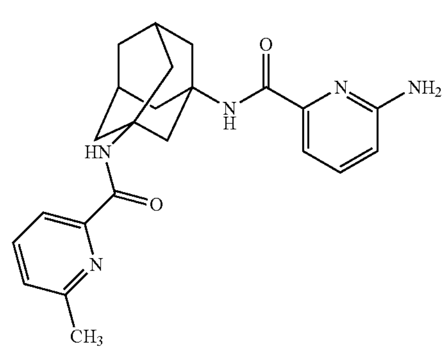 | 6-Methyl-pyridine-2-carboxylic acid {3-[(6-aminopyridine-2-carobnyl)-amino]-adamantan-1-yl}-amide |

TABLE 1-continued

| EXAMPLE | STRUCTURE | CHEMICAL NAME |
|---|---|---|
| 118 | 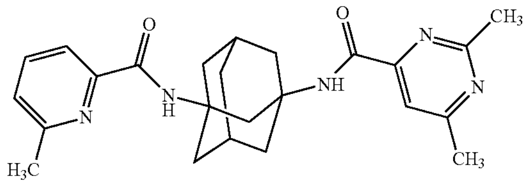 | 2,6-Dimethyl-pyrimidine-4-carboxylic acid {3-[(6-methyl-pyridine-2-carbonyl)-amino]-adamantan-1-yl}-amide |
| 119 | 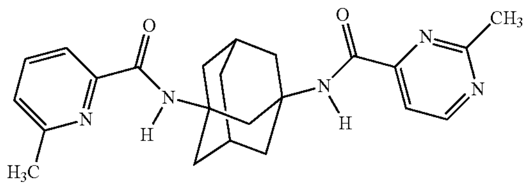 | 2-Methyl-pyrimidine-4-carboxylic acid {3-[(6-methyl-pyridine-2-carbonyl)-amino]-adamantan-1-yl}-amide |
| 120 | 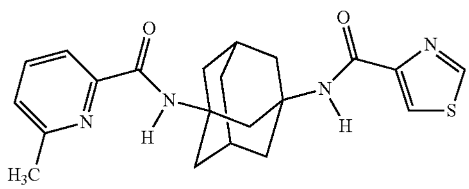 | 6-Methyl-pyridine-2-carboxylic acid {3-[(thiazole-4-carbonyl)-amino]-adamantan-1-yl}-amide |
| 121 | 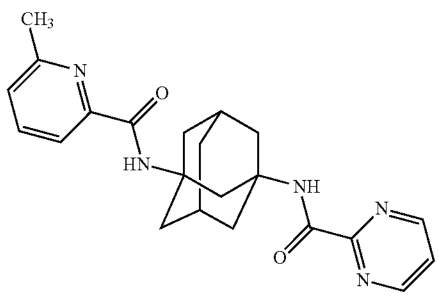 | Pyrimidine-2-carboxylic acid {3-[(6-methyl-pyridine-2-carbonyl)-amino]-adamantan-1-yl}-amide |
| 122 | 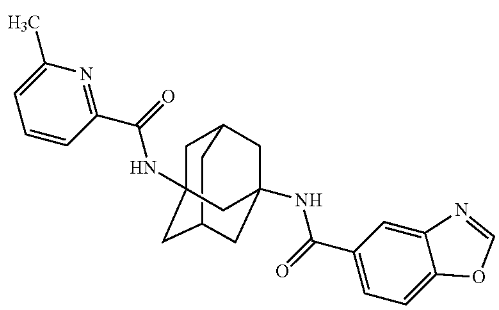 | Benzoxazole-5-carboxylic acid {3-[(6-methyl-pyridine-2-carobnyl)-amino]-adamantan-1-yl}-amide |
| 123 | 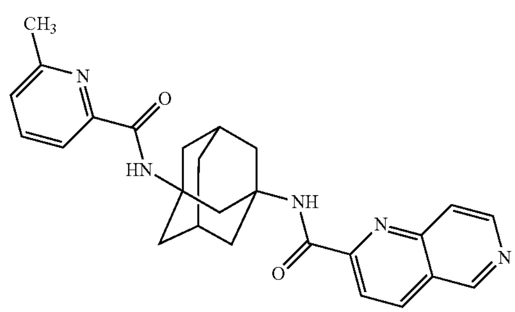 | [1,6]Naphthyridine-2-carboxylic acid {3-[(6-methyl-pyridine-2-carbonyl)-amino]-adamantan-1-yl}-amide |

TABLE 1-continued

| EXAMPLE | STRUCTURE | CHEMICAL NAME |
|---|---|---|
| 124 | 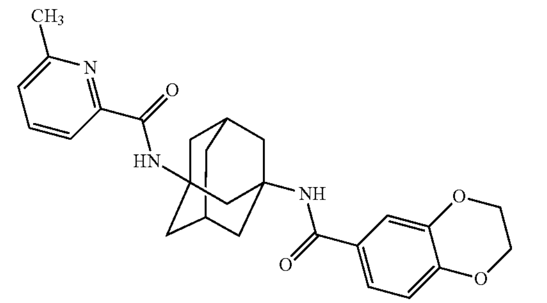 | 6-Methyl-pyridine-2-carboxylic acid {3-[(2,3-dihydro-benzo[1,4]dioxine-6-carbonyl)-amino]-adamantan-1-yl}-amide |
| 125 | 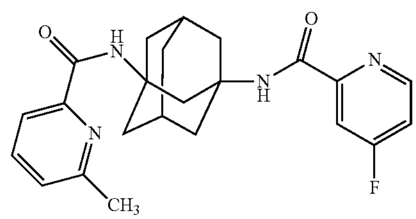 | 6-Methyl-pyridine-2-carboxylic acid {3-[(4-fluoropyridine-2-carbonyl)-amino]-adamantan-1-yl}-amide |
| 126 | 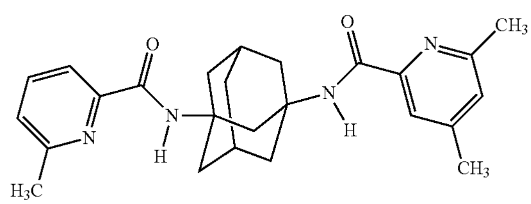 | 4,6-Dimethyl-pyridine-2-carboxylic acid {3-[(6-methyl-pyridine-2-carbonyl)-amino]-adamantan-1-yl}-amide |
| 127 | 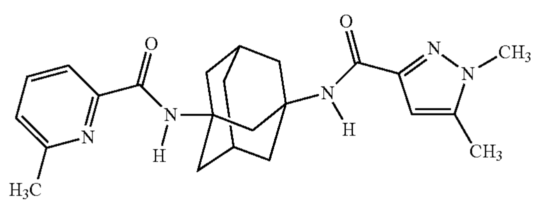 | 6-Methyl-pyridine-2-carboxylic acid {3-[(1,5-dimethyl-1H-pyrazole-3-carbonyl)-amino]-adamantan-1-yl}-amide |
| 128 | 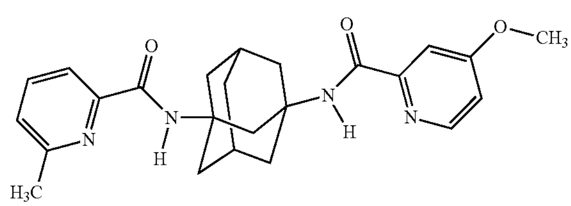 | 6-Methyl-pyridine-2-carboxylic acid {3-[(4-methoxypyridine-2-carobnyl)-amino]-adamantan-1-yl}-amide |
| 129 | 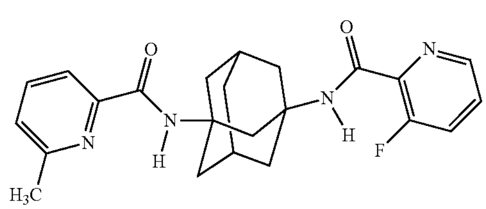 | 6-Methyl-pyridine-2-carboxylic acid {3-[(3-fluoropyridine-2-carbonyl)-amino]-adamantan-1-yl}-amide |
| 130 | 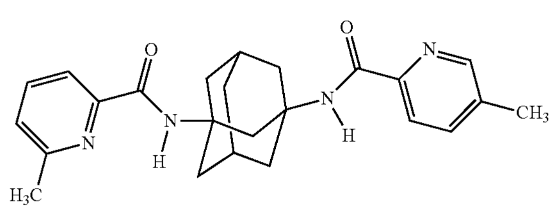 | 6-Methyl-pyridine-2-carboxylic acid {3-[(5-methylpyridine-2-carobnyl)-amino]-adamantan-1-yl}-amide |

TABLE 1-continued

| EXAMPLE | STRUCTURE | CHEMICAL NAME |
| --- | --- | --- |
| 131 | 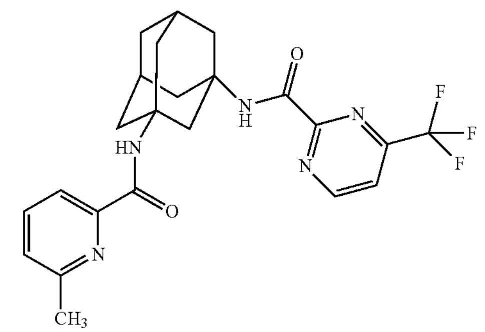 | 4-Trifluoromethyl-pyrimidine-2-carboxylic acid {3-[(6-methyl-pyridine-2-carbonyl)-amino]-adamantan-1-yl}-amide |
| 132 | 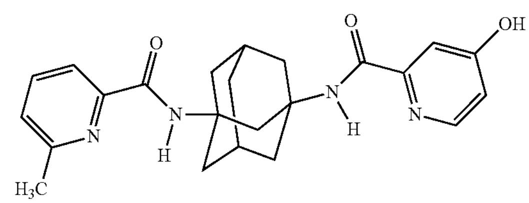 | 6-Methyl-pyridine-2-carboxylic acid {3-[(4-hydroxypyridine-2-carbonyl)-amino]-adamantan-1-yl}-amide |
| 133 | 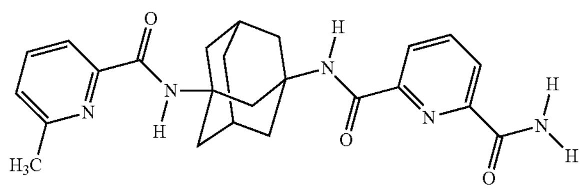 | Pyridine-2,6-dicarboxylic acid 2-amide 6-({3-[(6-methyl-pyridine-2-carbonyl)-amino]-adamantan-1-yl}-amide) |
| 134 | 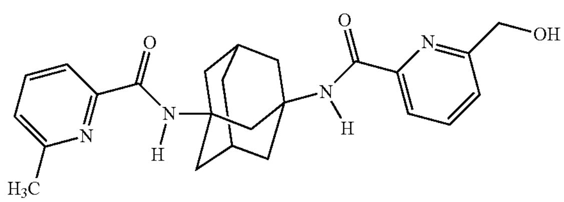 | 6-Methyl-pyridine-2-carboxylic acid {3-[(6-hydroxymethylpyridine-2-carbonyl)-amino]-adamantan-1-yl}-amide |
| 135 | 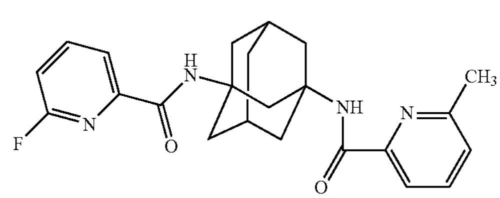 | 6-Methyl-pyridine-2-carboxylic acid {3-[(6-fluoropyridine-2-carbonyl)-amino]-adamantan-1-yl}-amide |
| 136 | 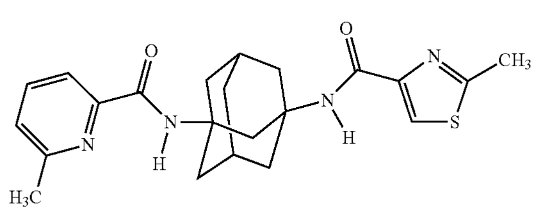 | 6-Methyl-pyridine-2-carboxylic acid {3-[(2-methyl-thiazole-4-carbonyl)-amino]-adamantan-1-yl}-amide |

TABLE 1-continued

| EXAMPLE | STRUCTURE | CHEMICAL NAME |
| --- | --- | --- |
| 137 | 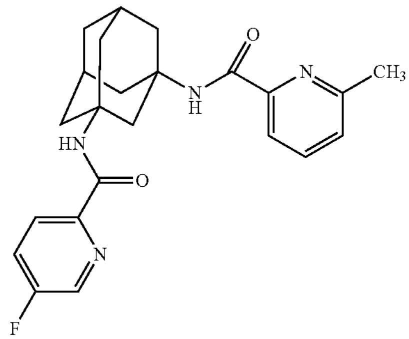 | 5-Fluoro-pyridine-2-carboxylic acid {3-[(6-methyl-pyridine-2-carbonyl)-amino]-adamantan-1-yl}-amide |
| 138 | 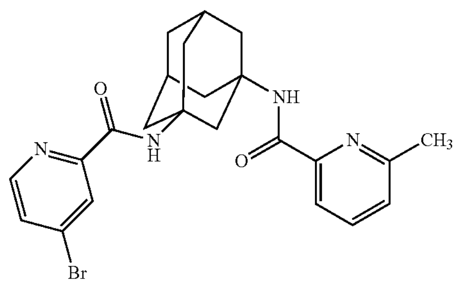 | 6-Methyl-pyridine-2-carboxylic acid {3-[(4-bromopyridine-2-carbonyl)-amino]-adamantan-1-yl}-amide |
| 139 | 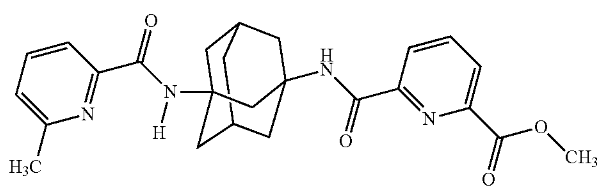 | 6-{3-[(6-Methyl-pyridine-2-carbonyl)-amino]-adamantan-1-ylcarbonyl}-pyridine-2-carboxylic acid methyl ester |
| 140 | 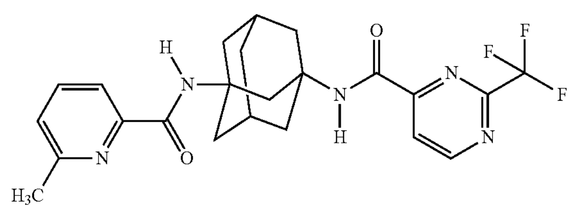 | 2-Trifluoromethyl-pyrimidine-4-carboxylic acid {3-[(6-methyl-pyridine-2-carbonyl)-amino]-adamantan-1-yl}-amide |
| 141 | 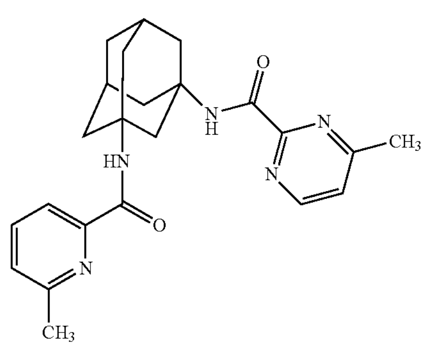 | 4-Methyl-pyrimidine-2-carboxylic acid {3-[(6-methyl-pyridine-2-carbonyl)-amino]-adamantan-1-yl}-amide |
| 142 | 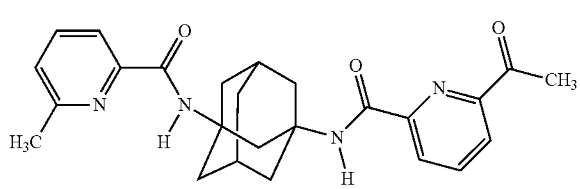 | 6-Methyl-pyridine-2-carboxylic acid {3-[(6-acetylpyridine-2-carbonyl)-amino]-adamantan-1-yl}-amide |

TABLE 1-continued

| EXAMPLE | STRUCTURE | CHEMICAL NAME |
|---|---|---|
| 143 | 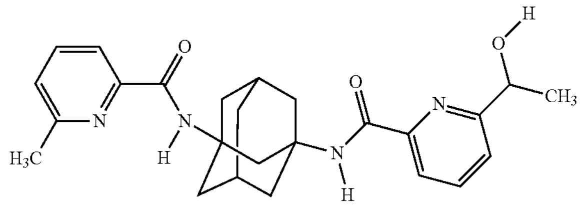 | 6-Methyl-pyridine-2-carboxylic acid {3-[(6-(1-hydroxy-ethyl)-pyridine-2-carbonyl)-amino]-adamantan-1-yl}-amide |
| 144 | 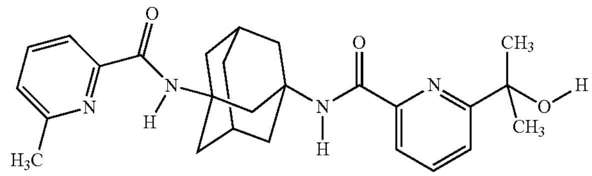 | 6-Methyl-pyridine-2-carboxylic acid {3-[(6-(1-hydroxy-1-methyl-ethyl)-pyridine-2-carbonyl)-amino]-adamantan-1-yl}-amide |
| 145 | 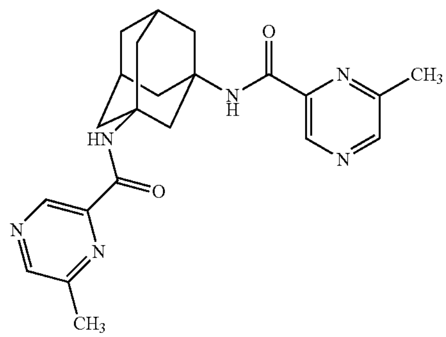 | N,N'-(1,3-adamantylene)bis(6-methyl-pyrazine-2-carboxamide) |
| 146 | 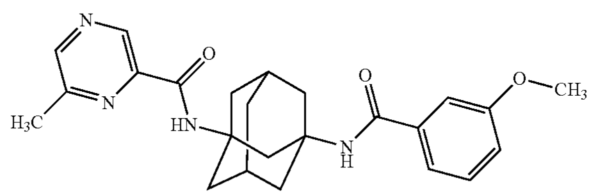 | 6-Methyl-pyrazine-2-carboxylic acid [3-(3-methoxy-benzoylamino)-adamantan-1-yl]-amide |
| 147 | 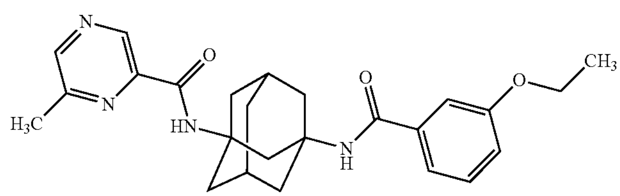 | 6-Methyl-pyrazine-2-carboxylic acid [3-(3-ethoxy-benzoylamino)-adamantan-1-yl]-amide |
| 148 | 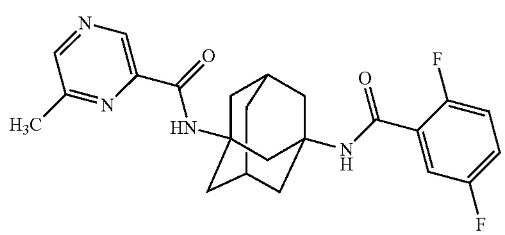 | 6-Methyl-pyrazine-2-carboxylic acid [3-(2,5-difluoro-benzoylamino)-adamantan-1-yl]-amide |
| 149 | 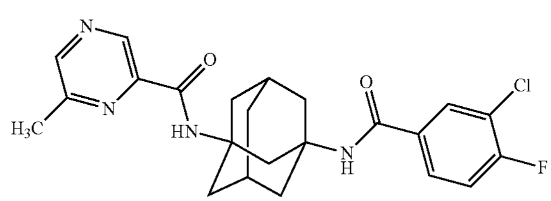 | 6-Methyl-pyrazine-2-carboxylic acid [3-(3-chloro-4-fluoro-benzoylamino)-adamantan-1-yl]-amide |

TABLE 1-continued

| EXAMPLE | STRUCTURE | CHEMICAL NAME |
|---|---|---|
| 150 | 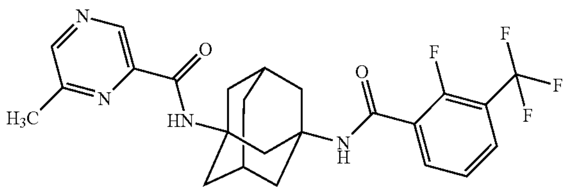 | 6-Methyl-pyrazine-2-carboxylic acid [3-(2-fluoro-3-trifluoromethyl-benzoylamino)-adamantan-1-yl]-amide |
| 151 | 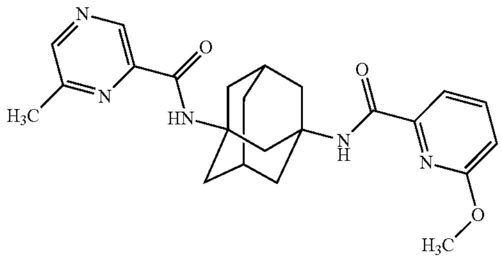 | 6-Methyl-pyrazine-2-carboxylic acid {3-[(6-methoxy-pyridine-2-carbonyl)-amino]-adamantan-1-yl}-amide |
| 152 | 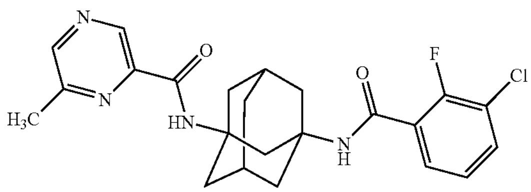 | 6-Methyl-pyrazine-2-carboxylic acid [3-(3-chloro-2-fluoro-benzoylamino)-adamantan-1-yl]-amide |
| 153 | 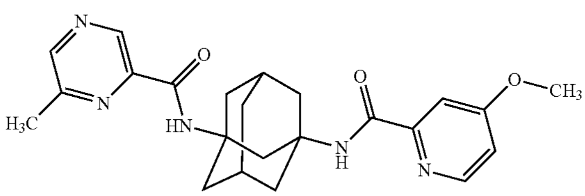 | 6-Methyl-pyrazine-2-carboxylic acid {3-[(4-methoxy-pyridine-2-carbonyl)-amino]-adamantan-1-yl}-amide |
| 154 | 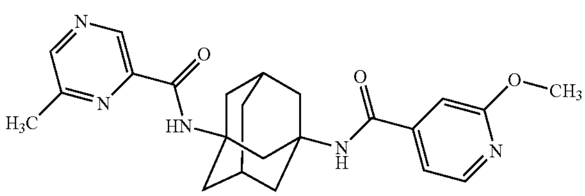 | 6-Methyl-pyrazine-2-carboxylic acid {3-[(2-methoxy-pyridine-4-carobnyl)-amino]-adamantan-1-yl}-amide |
| 155 | 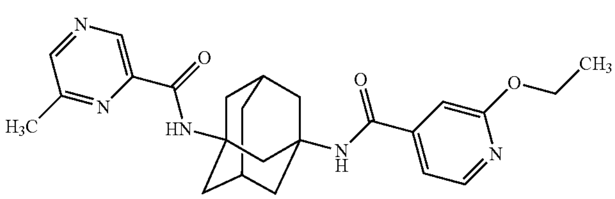 | 6-Methyl-pyrazine-2-carboxylic acid {3-[(2-ethoxy-pyridine-4-carbonyl)-amino]-adamantan-1-yl}-amide |
| 156 | 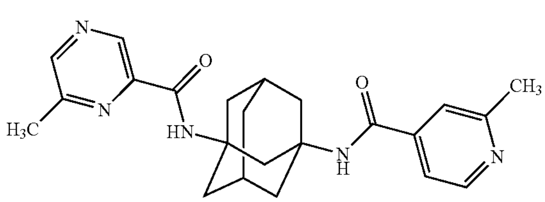 | 6-Methyl-pyrazine-2-carboxylic acid {3-[(2-methyl-pyridine-4-carbonyl)-amino]-adamantan-1-yl}-amide |

TABLE 1-continued

| EXAMPLE | STRUCTURE | CHEMICAL NAME |
|---|---|---|
| 157 | 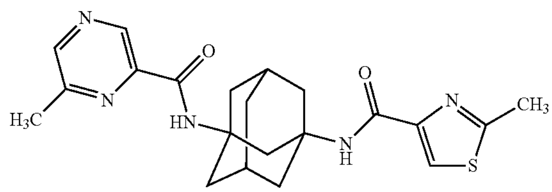 | 6-Methyl-pyrazine-2-carboxylic acid {3-[(2-methyl-thiazole-4-carbonyl)-amino]-adamantan-1-yl}-amide |
| 158 | 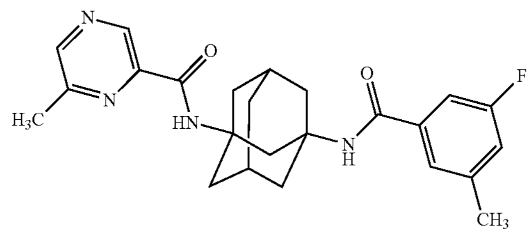 | 6-Methyl-pyrazine-2-carboxylic acid [3-(3-fluoro-5-methyl-benzoylamino)-adamantan-1-yl]-amide |
| 159 | 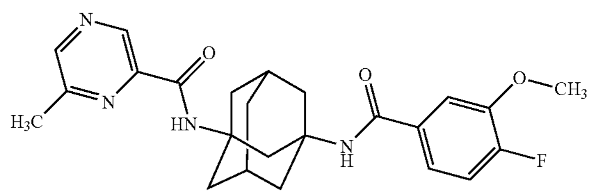 | 6-Methyl-pyrazine-2-carboxylic acid [3-(4-fluoro-3-methoxy-benzoylamino)-adamantan-1-yl]-amide |
| 160 | 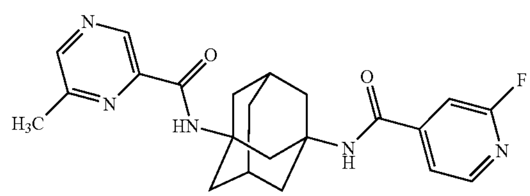 | 6-Methyl-pyrazine-2-carboxylic acid {3-[(2-fluoro-pyridine-4-carbonyl)-amino]-adamantan-1-yl}-amide |
| 161 | 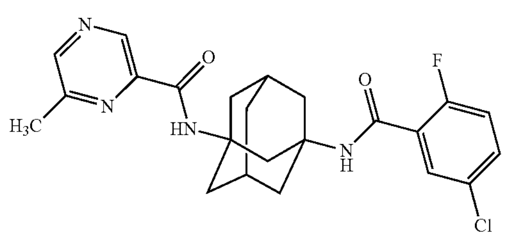 | 6-Methyl-pyrazine-2-carboxylic acid [3-(5-chloro-2-fluoro-benzoylamino)-adamantan-1-yl]-amide |
| 162 | 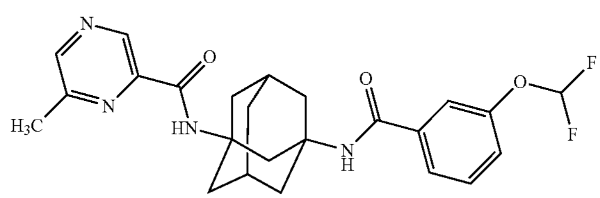 | 6-Methyl-pyrazine-2-carboxylic acid [3-(3-difluoromethoxy-benzoylamino)-adamantan-1-yl]-amide |
| 163 | 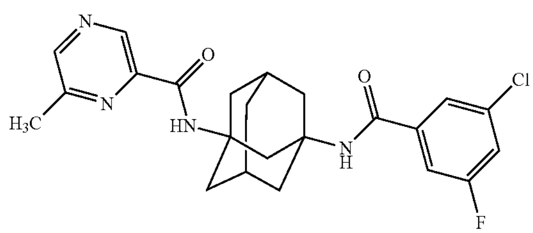 | 6-Methyl-pyrazine-2-carboxylic acid [3-(3-chloro-5-fluoro-benzoylamino)-adamantan-1-yl]-amide |

| EXAMPLE | STRUCTURE | CHEMICAL NAME |
|---|---|---|
| 164 | 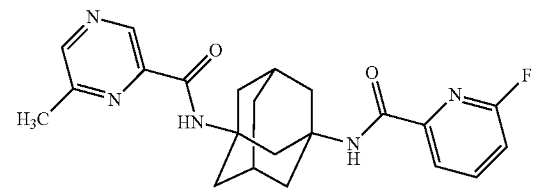 | 6-Methyl-pyrazine-2-carboxylic acid {3-[(6-fluoro-pyridine-2-carbonyl)-amino]-adamantan-1-yl}-amide |
| 165 | 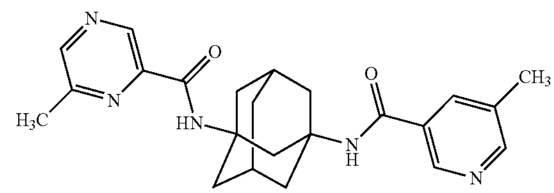 | 6-Methyl-pyrazine-2-carboxylic acid {3-[(5-methyl-pyridine-3-carbonyl)-amino]-adamantan-1-yl}-amide |
| 166 | 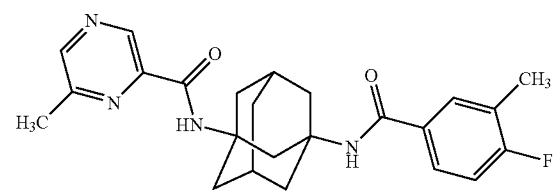 | 6-Methyl-pyrazine-2-carboxylic acid [3-(4-fluoro-3-methyl-benzoylamino)-adamantan-1-yl]-amide |
| 167 | 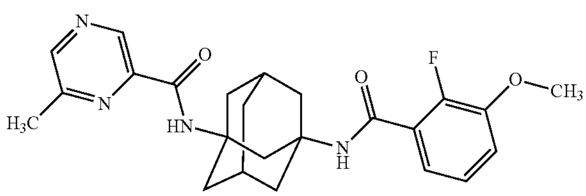 | 6-Methyl-pyrazine-2-carboxylic acid [3-(2-fluoro-3-methoxy-benzoylamino)-adamantan-1-yl]-amide |
| 168 | 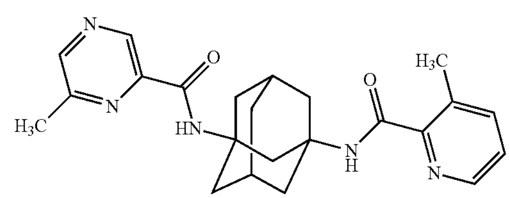 | 6-Methyl-pyrazine-2-carboxylic acid {3-[(3-methyl-pyridine-2-carobnyl)-amino]-adamantan-1-yl}-amide |
| 169 | 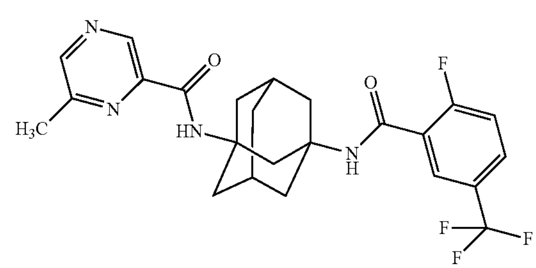 | 6-Methyl-pyrazine-2-carboxylic acid [3-(2-fluoro-5 trifluoromethyl-benzoylamino)-adamantan-1-yl]-amide |
| 170 | 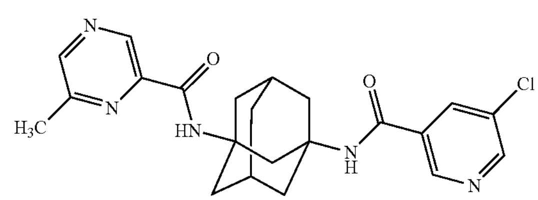 | 6-Methyl-pyrazine-2-carboxylic acid {3-[(5-chloro-pyridine-3-carbonyl)-amino]-adamantan-1-yl}-amide |

TABLE 1-continued

| EXAMPLE | STRUCTURE | CHEMICAL NAME |
|---|---|---|
| 171 | 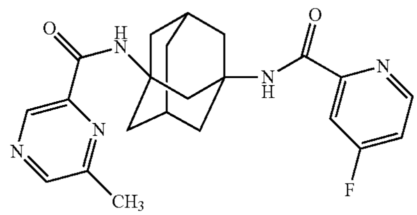 | 6-Methyl-pyrazine-2-carboxylic acid {3-[(4-fluoro-pyridine-2-carbonyl)-amino]-adamantan-1-yl}-amide |
| 172 | 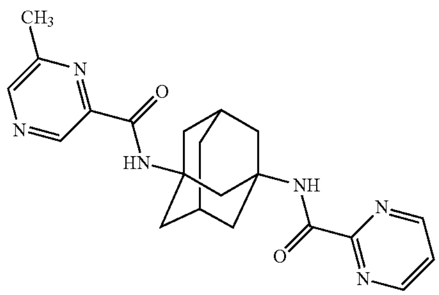 | Pyrimidine-2-carboxylic acid {3-[(6-methyl-pyrazine-2-carbonyl)-amino]-adamantan-1-yl}-amide |
| 173 | 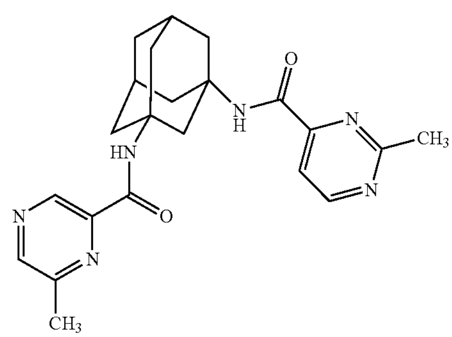 | 2-Methyl-pyrimidine-4-carboxylic cacid {3-[(6-methyl-pyrazine-2-carbonyl)-amino]-adamantan-1-yl}-amide |
| 174 | 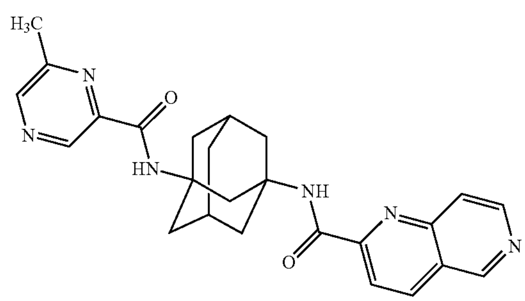 | [1,6]Naphthyridine-2-carboxylic acid {3-[(6-methyl-pyrazine-2-carbonyl)-amino]-adamantan-1-yl}-amide |
| 175 | 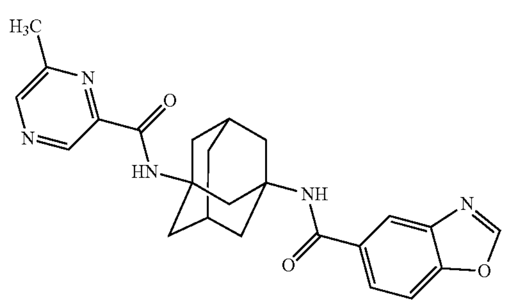 | Benzoxazole-5-carboxylic acid {3-[(6-methyl-pyrazine-2-carbonyl)-amino]-adamantan-1-yl}-amide |

| EXAMPLE | STRUCTURE | CHEMICAL NAME |
|---|---|---|
| 176 | 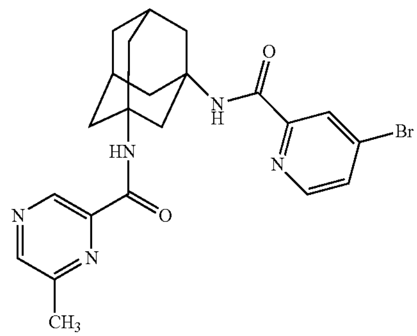 | 6-Methyl-pyrazine-2-carboxylic acid {3-[(4-bromo-pyridine-2-carbonyl)-amino]-adamantan-1-yl}-amide |
| 177 | 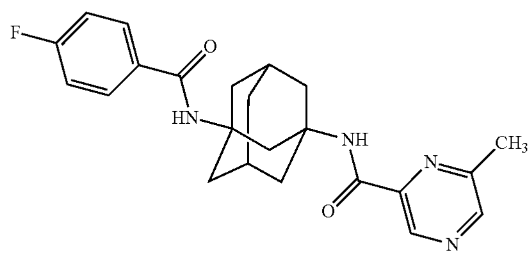 | 6-Methyl-pyrazine-2-carboxylic acid [3-(4-fluoro-benzoylamino)-adamantan-1-yl]-amide |
| 178 | 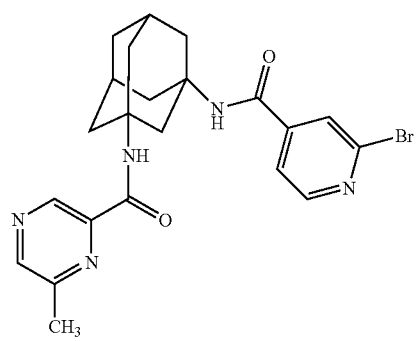 | 6-Methyl-pyrazine-2-carboxylic acid {3-[(2-bromo-pyridine-4-carbonyl)-amino]-adamantan-1-yl}-amide |
| 179 | 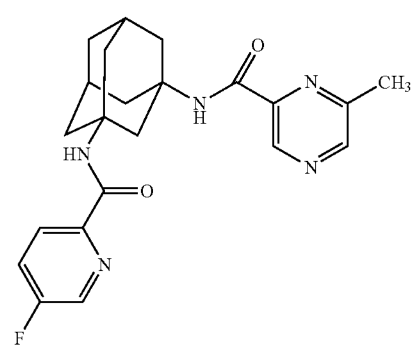 | 6-Methyl-pyrazine-2-carboxylic acid {3-[(5-fluoro-pyridine-2-carbonyl)-amino]-adamantan-1-yl}-amide |
| 180 | 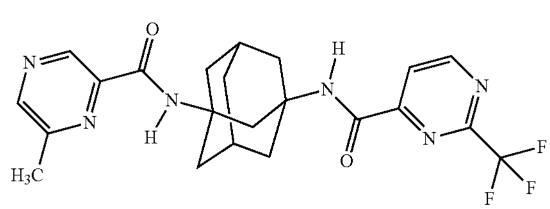 | 2-Trifluoromethyl-pyrimidine-4-carboxylic acid {3-[(6-methyl-pyrazine-2-carbonyl)-amino]-adamantan-1-yl}-amide |

| EXAMPLE | STRUCTURE | CHEMICAL NAME |
|---|---|---|
| 181 | 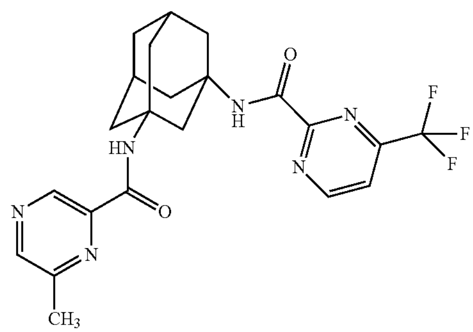 | 4-Trifluoromethyl-pyrimidine-2-carboxylic acid {3-[(6-methyl-pyrazine-2-carbonyl)-amino]-adamantan-1-yl}-amide |
| 182 | 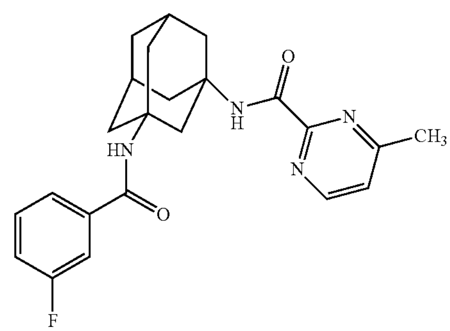 | 4-Methyl-pyrimidine-2-carboxylic acid [3-(3-fluoro-benzoylamino)-adamantan-1-yl]-amide |
| 183 | 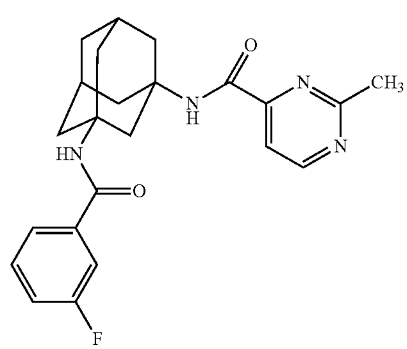 | 2-Methyl-pyrimidine-4-carboxylic acid [3-(3-fluoro-benzoylamino)-adamantan-1-yl]-amide |
| 184 | 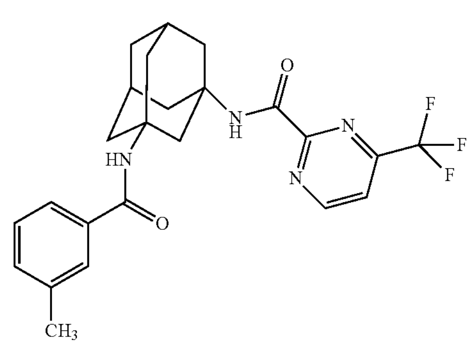 | 4-Trifluoromethyl-pyrimidine-2-carboxylic acid [3-(3-fluoro-benzoylamino)-adamantan-1-yl]-amide |

TABLE 1-continued

| EXAMPLE | STRUCTURE | CHEMICAL NAME |
|---|---|---|
| 185 | 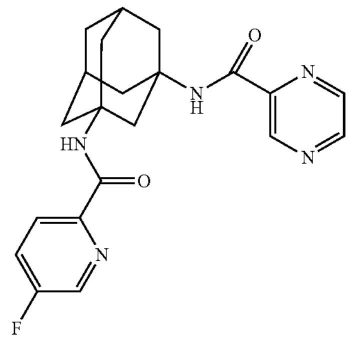 | Pyrazine-2-carboxylic acid {3-[(5-fluoro-pyridine-2-carbonyl)-amino]-adamantan-1-yl}-amide |
| 186 | 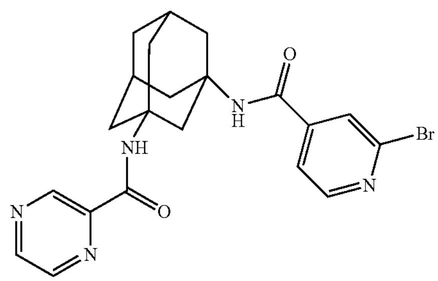 | Pyrazine-2-carboxylic acid {3-[(2-bromo-pyridine-4-carbonyl)-amino]-adamantan-1-yl}-amide |
| 187 | 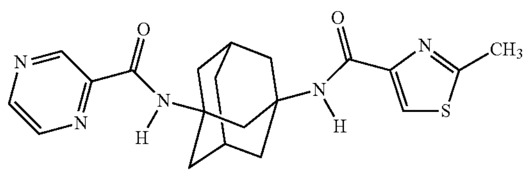 | Pyrazine-2-carboxylic acid {3-[(2-methyl-thiazole-4-carbonyl)-amino]-adamantan-1-yl}-amide |
| 188 | 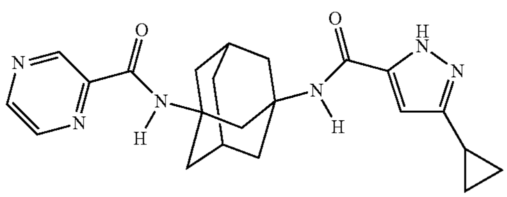 | Pyrazine-2-carboxylic acid {3-[(5-cyclopropyl-2H-pyrazole-3-carbonyl)-amino]-adamantan-1-yl}-amide |
| 189 | 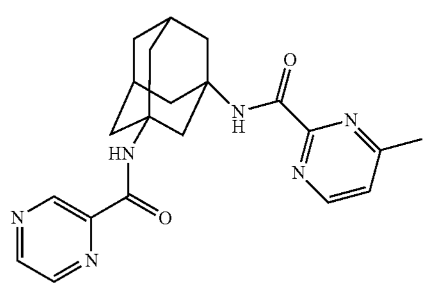 | 4-Methyl-pyrimidine-2-carboxylic acid {3-[(pyrazine-2-carbonyl)-amino]-adamantan-1-yl}-amide |
| 190 | 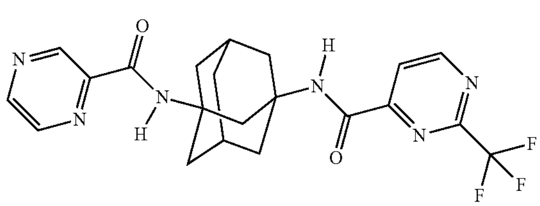 | 2-Trifluoromethyl-pyrimidine-4-carboxylic acid {3-[(pyrazine-2-carbonyl)-amino]-adamantan-1-yl}-amide |

| EXAMPLE | STRUCTURE | CHEMICAL NAME |
|---|---|---|
| 191 | 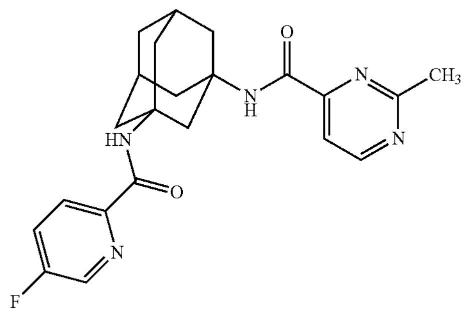 | 2-Methyl-pyrimidine-4-carboxylic acid {3-[(5-fluoro-pyridine-2-carbonyl)-amino]-adamantan-1-yl}-amide |
| 192 | 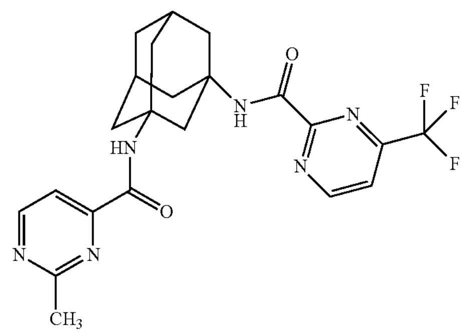 | 4-Trifluoromethyl-pyrimidine-2-carboxylic acid {3-[(2-methyl-pyrimidine-4-carbonyl)-amino]-adamantan-1-yl}-amide |
| 193 | 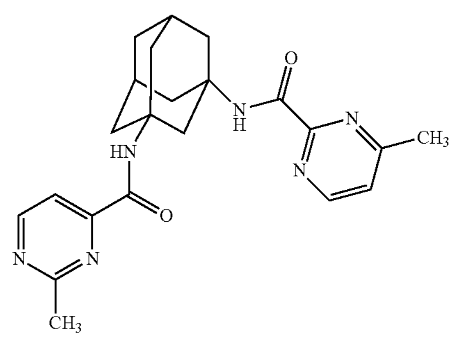 | 2-Methyl-pyrimidine-4-carboxylic acid {3-[(4-methyl-pyrimidine-2-carbonyl)-amino]-adamantan-1-yl}-amide |
| 194 | 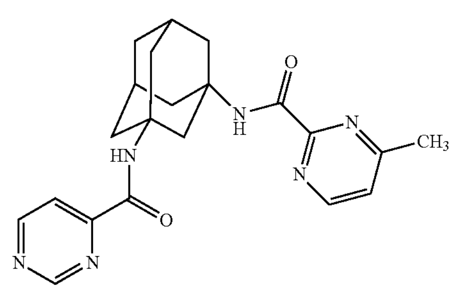 | 4-Methyl-pyrimidine-2-carboxylic acid {3-[(pyrimidine-4-carbonyl)-amino]-adamantan-1-yl}-amide |
| 195 | 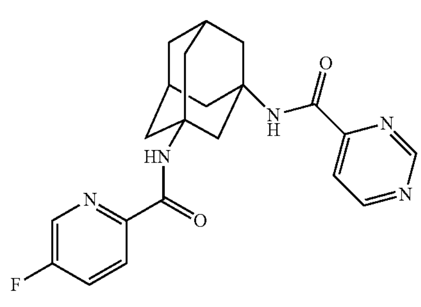 | Pyrimidine-4-carboxylic acid {3-[(5-fluoro-pyridine-2-carobnyl)-amino]-adamantan-1-yl}-amide |

TABLE 1-continued

| EXAMPLE | STRUCTURE | CHEMICAL NAME |
|---|---|---|
| 196 | 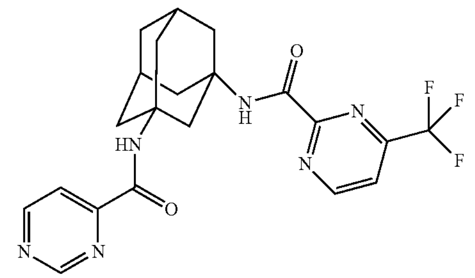 | 4-Trifluoromethyl-pyrimidine-2-carboxylic acid {3-[(pyrimidine-4-carbonyl)-amino]-adamantan-1-yl}-amide |

Example 197

6-Morpholin-4-yl-pyridine-2-carboxylic acid {3-[(pyridine-2-carbonyl)-amino]-adamantan-1-yl}-amide

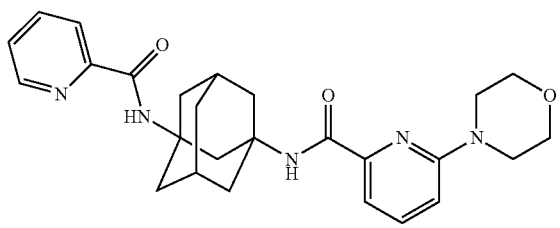

Example 197 in Table 2 (below) was synthesized from Intermediate 4 via the process of Scheme 7, supra, as follows:

To a microwave vial was added a stir bar, 6-chloro-pyridine-2-carboxylic acid {3-[(pyridine-2-carbonyl)-amino]-adamantan-1-yl}-amide (Intermediate 4, 20 mg, 0.05 mmol), DMA (1.0 mL), morpholine (0.05 mL) and cesium carbonate (60 mg, 0.15 mmol). The mixture was heated at 180° C. under microwave irradiation for 15 minutes.

The reaction mixture was cooled to room temperature. Solvent was removed in a high performance solvent evaporation system HT-4X (Genevac Inc., supra). The residue was dissolved in DCM (2 mL), washed with aq. 1 N NaOH (2 mL) and water (2×2 mL). After removing the solvent, the residue was purified on a RP-HPLC/MS purification system (Gradient: acetonitrile in water with a cycle time of 5 min. Flow rate: 100 mL/min. Mobile phase additive: 25 mM of ammonium acetate. Column: Inertsil® C8, 30×50 mm, 5 µm particle size (GL Sciences, Tokyo, Japan)) to afford 1.3 mg of the title compound, 6-morpholin-4-yl-pyridine-2-carboxylic acid {3-[(pyridine-2-carbonyl)-amino]-adamantan-1-yl}-amide. The product was quality checked (QC) by LC-MS (Gradient: acetonitrile in water, 30-90%, in 1.7 minutes with a cycle time of 2 min. Flow rate: 5.0 mL/min. Mobile phase additive: 30 mM of ammonium formate. Column: Inertsil® C8, 50×4.6 mm, 3 µm particle size (GL Sciences, Tokyo, Japan)): Retention time: 1.26 min; purity (UV$_{254}$): 95%; ESI-MS m/z: 462.1 (M+H)$^+$.

In an analogous manner to Example 197, Examples 198-203 in Table 2 (below) were synthesized from Intermediate 4 and commercially available amines on 0.05-0.3 mmol scales; Examples 204-211 in Table 2 (below) were synthesized from Intermediate 5 and commercially available amines on a 0.05 mmol scale; and Examples 212-219 in Table 2 (below) were synthesized from Intermediate 6 and commercially available amines on a 0.05 mmol scale.

Example 220

6-(3-Methoxy-propylamino)-pyridine-2-carboxylic acid {3-[(pyridine-2-carbonyl)-amino]-adamantan-1-yl}-amide

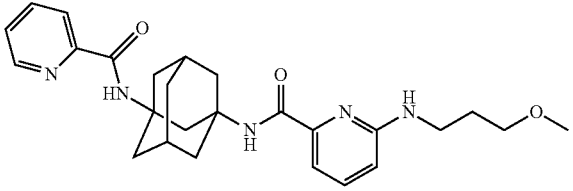

Example 220 in Table 2 (below) was synthesized from Intermediate 4 via the process of Scheme 7, supra, as follows:

To a microwave vial was added a stir bar, 6-chloro-pyridine-2-carboxylic acid {3-[(pyridine-2-carbonyl)-amino]-adamantan-1-yl}-amide (Intermediate 4, 20 mg, 0.05 mmol), copper (II) oxide (20 mg, 0.2 mmole), DMA (1 mL), 3-methoxy-propylamine (0.05 mL) and cesium carbonate (120 mg, 0.3 mmol). The mixture was heated at 230° C. under microwave irradiation for 30 min. Solvent was removed in Genevac. The residue was dissolved in DCM (2 mL), washed with aq. 1 N NaOH (2 mL), and water (2×2 mL). After removing the solvent, the crude product was purified on a RP-HPLC/MS system (Gradient: acetonitrile in water with a cycle time of 5 min. Flow rate: 100 mL/min. Mobile phase additive: 25 mM of ammonium acetate. Column: Inertsil® C8, 30×50 mm, 5 µm particle size (GL Sciences, Tokyo, Japan)) to afford 3.9 mg of the title compound, 6-(3-methoxy-propylamino)-pyridine-2-carboxylic acid {3-[(pyridine-2-carbonyl)-amino]-adamantan-1-yl}-amide. The product was quality checked (QC) by LC-MS (Gradient: acetonitrile in water, 30-90%, in 1.7 minutes with a cycle time of 2 min. Flow rate: 5.0 mL/min. Mobile phase additive: 30 mM of ammonium formate. Column: Inertsil® C8, 50×4.6 mm, 3 µm particle size (GL Sciences, Tokyo, Japan)): Retention time: 1.29 min; purity (UV$_{254}$): 94%; ESI-MS m/z: 464.6 (M+H)$^+$.

In an analogous manner to Example 220, Examples 219-230 in Table 2 (below) were synthesized from Intermediate 4 and commercially available amines on 0.05-0.3 mmol scales; Examples 231-240 in Table 2 (below) were synthesized from Intermediate 5 and commercially available amines on a 0.05 mmol scale; and Examples 241-252 in Table 2 (below) were synthesized from Intermediate 6 and commercially available amines on a 0.05 mmol scale.

Example 253

6-Imidazol-1-yl-pyridine-2-carboxylic acid {3-[(pyridine-2-carbonyl)-amino]-adamantan-1-yl}-amide

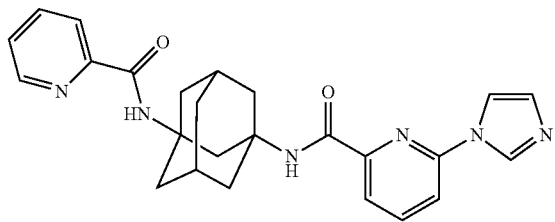

Example 253 in Table 2 (below) was synthesized from Intermediate 4 via the process of Scheme 7, supra, as follows:

To a microwave vial was added a stir bar, 6-chloro-pyridine-2-carboxylic acid {3-[(pyridine-2-carbonyl)-amino]-adamantan-1-yl}-amide (Intermediate 4, 20 mg, 0.05 mmol), copper (II) acetoacetonate (20 mg), DMA (1 mL), imidazole (50 mg, 0.73 mmol) and cesium carbonate (60 mg, 0.15 mmol). The mixture was heated at 180° C. under microwave irradiation for 15 minutes. Solvent was removed in a high performance solvent evaporation system HT-4X (Genevac, Inc., supra). The residue was dissolved in DCM (2 mL), washed with aq. 1 N NaOH (2 mL), and water (2×2 mL). After removing the solvent, the residue was purified on a RP-HPLC/MS system (Gradient: acetonitrile in water with a cycle time of 5 min. Flow rate: 100 mL/min. Mobile phase additive: 25 mM of ammonium acetate. Column: Inertsil® C8, 30×50 mm, 5 μm particle size (GL Sciences, Tokyo, Japan) to afford 4.5 mg of the title compound, 6-imidazol-1-yl-pyridine-2-carboxylic acid {3-[(pyridine-2-carbonyl)-amino]-adamantan-1-yl}-amide. ESI-MS m/z: 443.5 $(M+H)^+$.

In an analogous manner to Example 253, Examples 254-255 in Table 2 (below) were synthesized on a 0.05 mmol reaction scale from Intermediates 5 and 6, respectively.

TABLE 2

| EXAMPLE | STRUCTURE | CHEMICAL NAME |
|---|---|---|
| 197 | 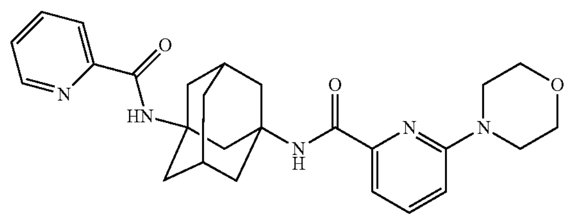 | 6-Morpholin-4-yl-pyridine-2-carboxylic acid {3-[(pyridine-2-carbonyl)-amino]-adamantan-1-yl}-amide |
| 198 | 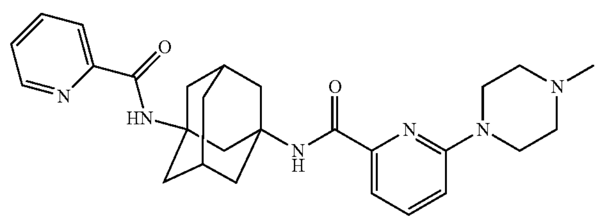 | 6-(4-Methyl-piperazin-1-yl)-pyridine-2-carboxylic acid {3-[(pyridine-2-carbonyl)-amino]-adamantan-1-yl}-amide |
| 199 | 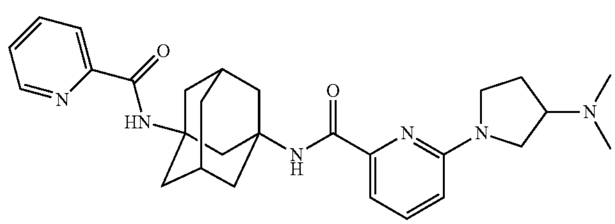 | 6-(3-Dimethylamino-pyrrolidin-1-yl)-pyridine-2-carboxylic acid {3-[(pyridine-2-carbonyl)-amino]-adamantan-1-yl}-amide |
| 200 | 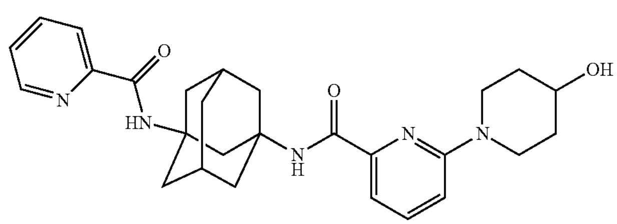 | 4-Hydroxy-3,4,5,6-tetrahydro-2H-[1,2']bipyridinyl-6'-carboxylic acid {3-[(pyridine-2-carbonyl)-amino]-adamantan-1-yl}-amide |

TABLE 2-continued

| EXAMPLE | STRUCTURE | CHEMICAL NAME |
|---|---|---|
| 201 | 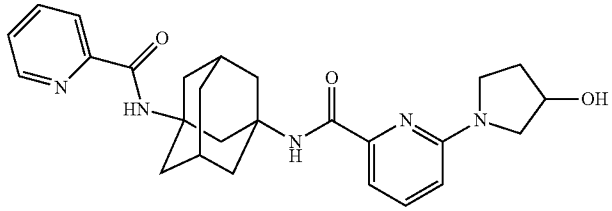 | 6-(3-Hydroxy-pyrrolidin-1-yl)-pyridine-2-carboxylic acid {3-[(pyridine-2-carbonyl)-amino]-adamantan-1-yl}-amide |
| 202 | 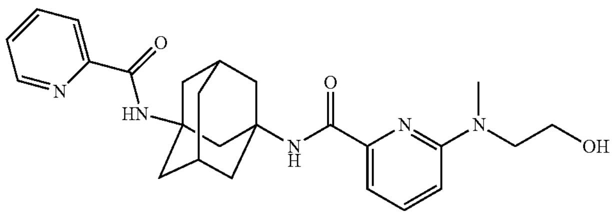 | 6-[(2-Hydroxy-ethyl)-methyl-amino]-pyridine-2-carboxylic acid {3-[(pyridine-2-carbonyl)-amino]-adamantan-1-yl}-amide |
| 203 | 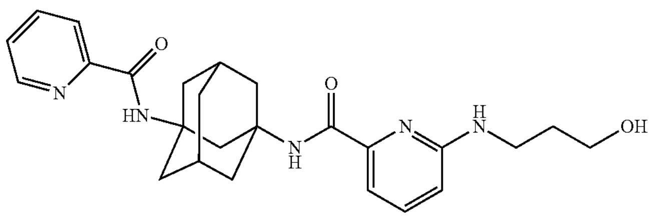 | 6-(3-Hydroxy-propylamino)-pyridine-2-carboxylic acid {3-[(pyridine-2-carbonyl)-amino]-adamantan-1-yl}-amide |
| 204 | 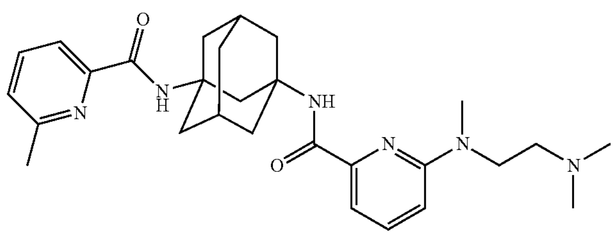 | 6-[(2-Dimethylamino-ethyl)-methyl-amino]-pyridine-2-carboxylic acid{3-[(6-methyl-pyridine-2-carbonyl)-amino]-adamantan-1-yl}-amide |
| 205 | 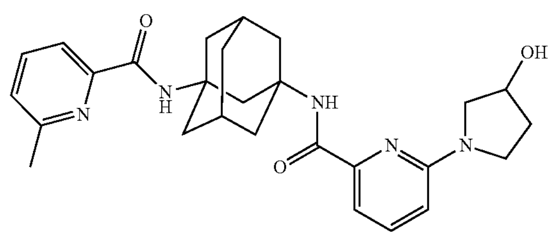 | 6-(3-Hydroxy-pyrrolidin-1-yl)-pyridine-2-carboxylic acid{3-[(6-methyl-pyridine-2-carbonyl)-amino]-adamantan-1-yl}-amide |
| 206 | 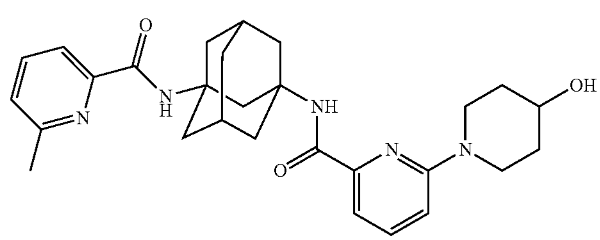 | 4-Hydroxy-3,4,5,6-tetrahydro-2H-[1,2']bipyridinyl-6'-carboxylic acid{3-[(6-methyl-pyridine-2-carbonyl)-amino]-adamantan-1-yl}-amide |
| 207 | 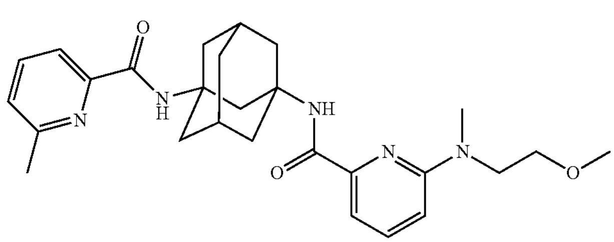 | 6-[(2-Methoxy-ethyl)-methyl-amino]-pyridine-2-carboxylic acid{3-[(6-methyl-pyridine-2-carbonyl)-amino]-adamantan-1yl}-amide |

TABLE 2-continued

| EXAMPLE | STRUCTURE | CHEMICAL NAME |
|---|---|---|
| 208 | 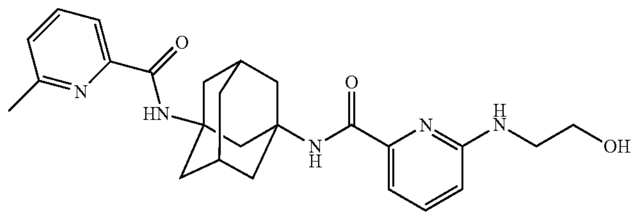 | 6-(2-Hydroxy-ethylamino)-pyridine-2-carboxylic acid {3-[(6-methyl-pyridine-2-carbonyl)-amino]-adamantan-1yl]-amide |
| 209 | 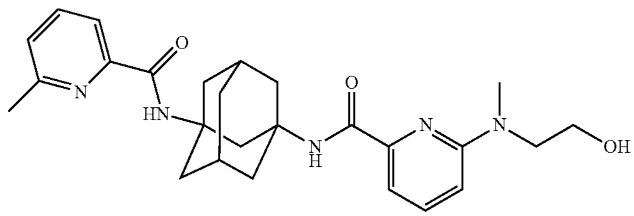 | 6-[(2-Hydroxy-ethyl)-methyl-amino]-pyridine-2-carboxylic acid {3-[(6-methyl-pyridine-2-carbonyl)-amino]-adamantan-1-yl}-amide |
| 210 | 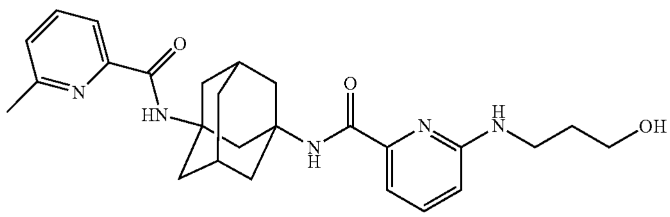 | 6-(3-Hydroxy-propylamino)-pyridine-2-carboxylic acid {3-[(6-methyl-pyridine-2-carbonyl)-amino]-adamantan-1-yl}-amide |
| 211 | 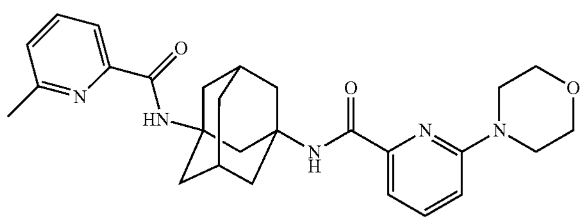 | 6-Morpholin-4-yl-pyridine-2-carboxylic acid {3-[(6-methyl-pyridine-2-carbonyl)-amino]-adamantan-1-yl}-amide |
| 212 | 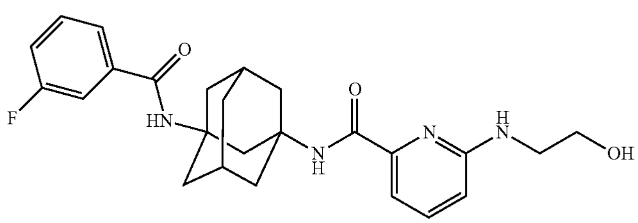 | 6-(2-Hydroxy-ethylamino)-pyridine-2-carboxylic acid [3-(3-fluoro-benzoylamino)-adamantan-1-yl]-amide |
| 213 | 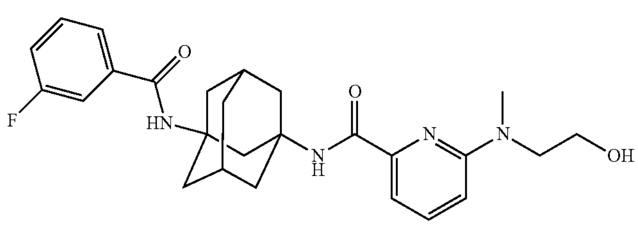 | 6-[(2-Hydroxy-ethyl)-methyl-amino]-pyridine-2-carboxylic acid [3-(3-fluoro-benzoylamino)-adamantan-1-yl]-amide |
| 214 | 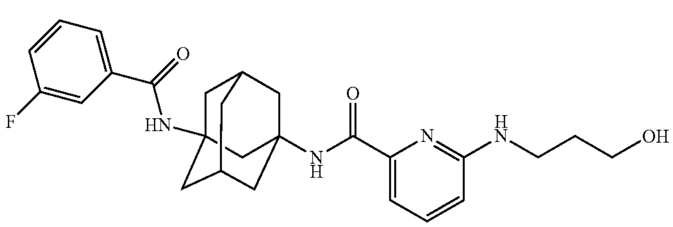 | 6-(3-Hydroxy-propylamino)-pyridine-2-carboxylic acid [3-(3-fluoro-benzoylamino)-adamantan-1-yl]-amide |

TABLE 2-continued

| EXAMPLE | STRUCTURE | CHEMICAL NAME |
|---|---|---|
| 215 | 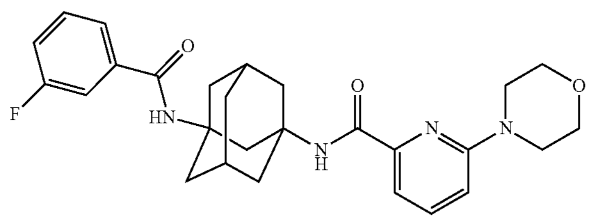 | 6-Morpholin-4-yl-pyridine-2-carboxylic acid [3-(3-fluoro-benzoylamino)-adamantan-1-yl]-amide |
| 216 | 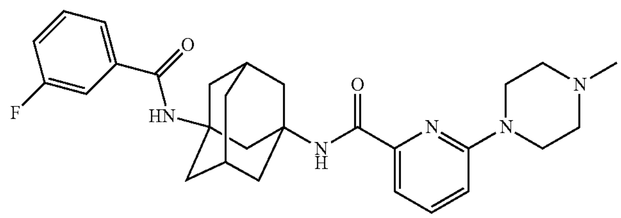 | 6-(4-Methyl-piperazin-1-yl)-pyridine-2-carboxylic acid [3-(3-fluoro-benzoylamino)-adamantan-1-yl]-amide |
| 217 | 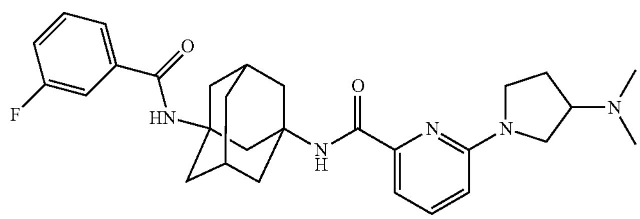 | 6-(3-Dimethylamino-pyrrolidin-1-yl)-pyridine-2-carboxylic acid [3-(3-fluoro-benzoylamino)-adamantan-1-yl]-amide |
| 218 | 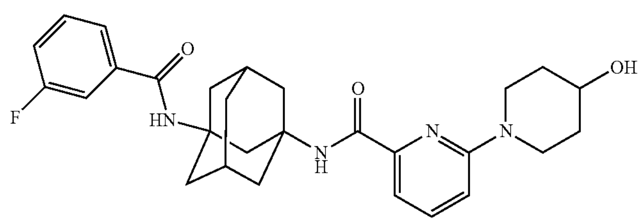 | 4-Hydroxy-3,4,5,6-tetrahydro-2H-[1,2']bipyridinyl-6'-carboxylic acid [3-(3-fluoro-benzoylamino)-adamantan-1-yl]-amide |
| 219 | 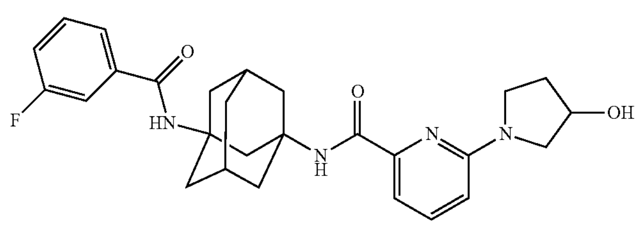 | 6-(3-Hydroxy-pyrrolidin-1-yl)-pyridine-2-carboxylic acid [3-(3-fluoro-benzoylamino)-adamantan-1-yl]-amide |
| 220 | 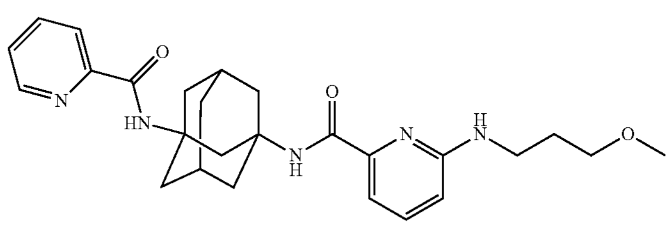 | 6-(3-Methoxy-propylamino)-pyridine-2-carboxylic acid {3-[(pyridine-2-carbonyl)-amino]-adamantan-1-yl}-amide |
| 221 | 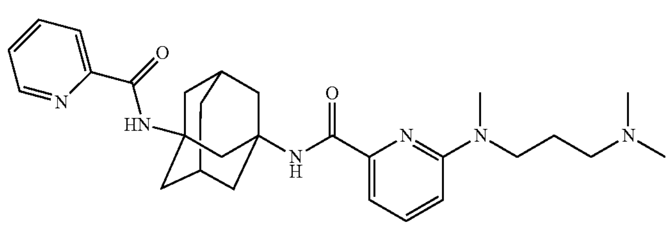 | 6-[(3-Dimethylamino-propyl)-methyl-amino]-pyridine-2-carboxylic acid {3-[(pyridine-2-carbonyl)-amino]adamantan-1-yl}-amide |

| EXAMPLE | STRUCTURE | CHEMICAL NAME |
|---|---|---|
| 222 | 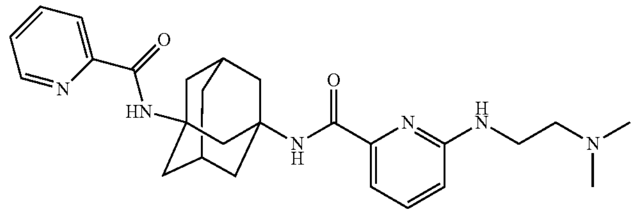 | 6-(2-Dimethylamino-ethylamino)-pyridine-2-carboxylic acid {3-[(pyridine-2-carbonyl)-amino]-adamantan-1-yl}-amide |
| 223 | 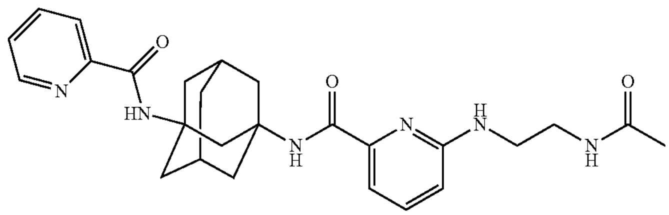 | 6-(2-Acetylamino-ethylamino)-pyridine-2-carboxylic acid {3-[(pyridine-2-carbonyl)-amino]-adamantan-1-yl}-amide |
| 224 | 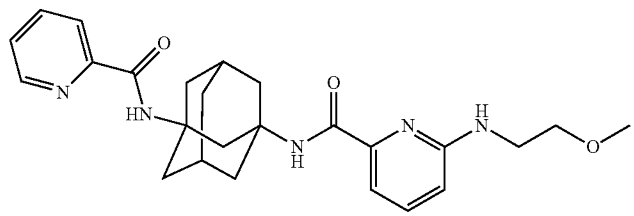 | 6-(2-Methoxy-ethylamino)-pyridine-2-carboxylic acid {3-[(pyridine-2-carbonyl)-amino]-adamantan-1-yl}-amide |
| 225 | 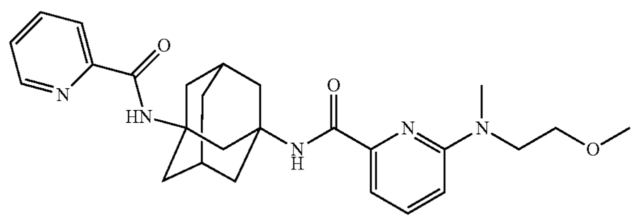 | 6-[(2-Methoxy-ethyl)-methyl-amino]-pyridine-2-carboxylic acid {3-[(pyridine-2-carbonyl)-amino]-adamantan-1-yl}-amide |
| 226 | 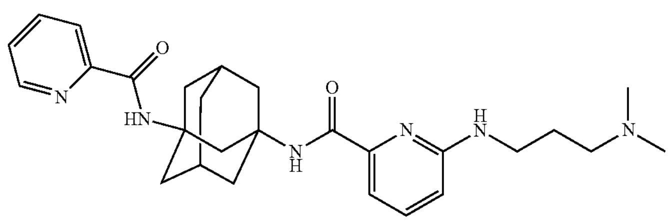 | 6-(3-Dimethylamino-propylamino)-pyridine-2-carboxylic acid {3-[(pyridine-2-carbonyl)-amino]-adamantan-1-yl}-amide |
| 227 | 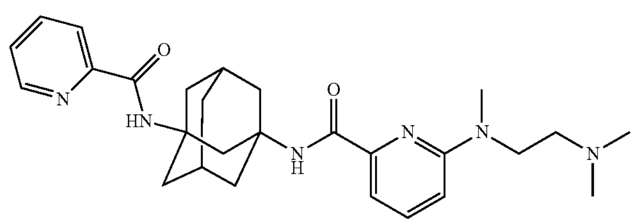 | 6-[(2-Dimethylamino-ethyl)-methyl-amino]-pyridine-2-carboxylic acid {3-[(pyridine-2-carbonyl)-amino]-adamantan-1-yl}-amide |
| 228 | 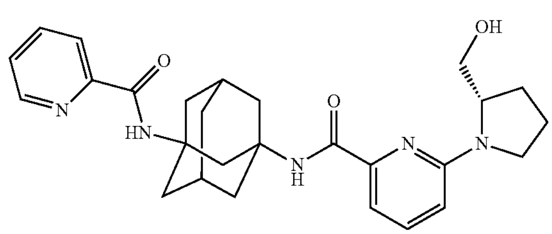 | 6-((S)-2-Hydroxymethyl-pyrrolidin-1-yl)-pyridine-2-carboxylic acid {3-[(pyridine-2-carbonyl)-amino]-adamantan-1-yl}-amide |

TABLE 2-continued

| EXAMPLE | STRUCTURE | CHEMICAL NAME |
|---|---|---|
| 229 | 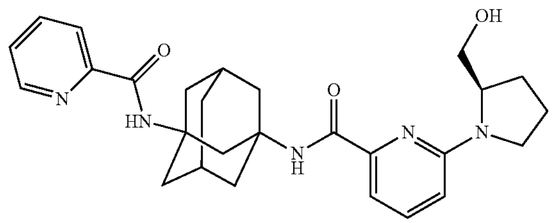 | 6-((R)-2-Hydroxymethyl-pyrrolidin-1-yl)-pyridine-2-carboxylic acid {3-[(pyridine-2-carbonyl)-amino]-adamantan-1-yl}-amide |
| 230 | 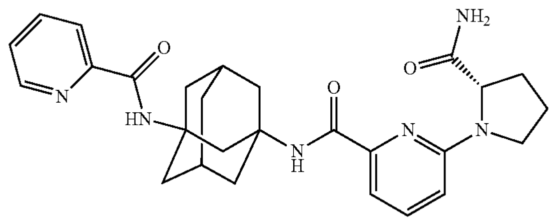 | 6-((S)-2-Carbamoyl-pyrrolidin-1-yl)-pyridine-2-carboxylic acid {3-[(pyridine-2-carbonyl)-amino]-adamantan-1-yl}-amide |
| 231 | 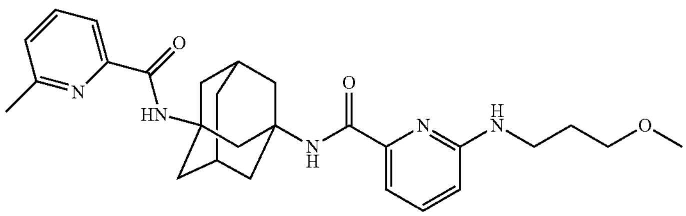 | 6-(3-Methoxy-propylamino)-pyridine-2-carboxylic acid {3-[(6-methyl-pyridine-2-carbonyl)-amino]-adamantan-1-yl}-amide |
| 232 | 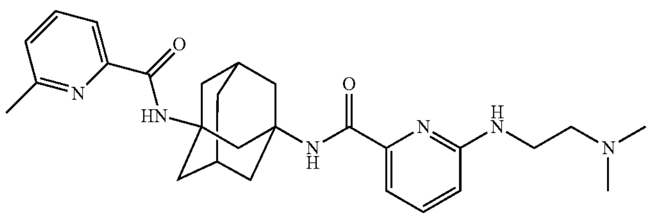 | 6-(2-Dimethylamino-ethylamino)-pyridine-2-carboxylic acid {3-[(6-methyl-pyridine-2-carbonyl)-amino]-adamantan-1-yl}-amide |
| 233 | 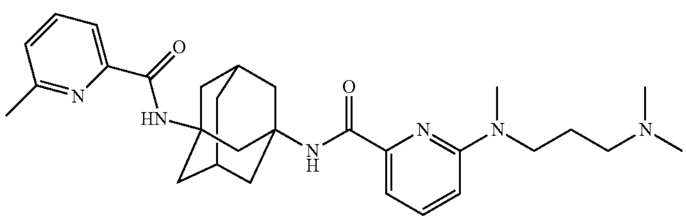 | 6-[(3-Dimethylamino-propyl)-methyl-amino]-pyridine-2-carboxylic acid {3-[(6-methyl-pyridine-2-carbonyl)-amino]-adamantan-1-yl}-amide |
| 234 | 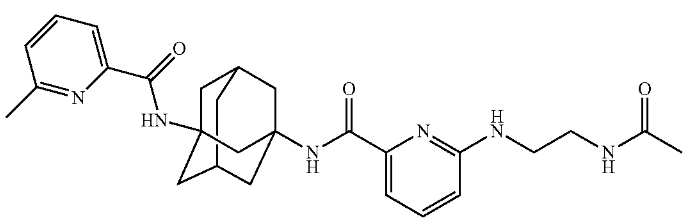 | 6-(2-Acetylamino-ethylamino)-pyridine-2-carboxylic acid {3-[(6-methyl-pyridine-2-carbonyl)-amino]-adamantan-1-yl}-amide |
| 235 | 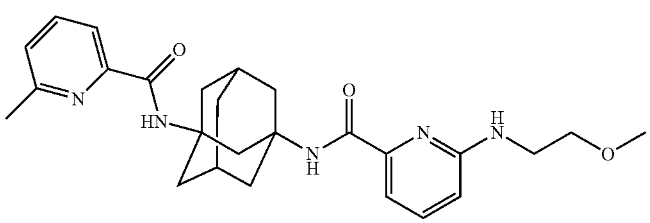 | 6-(2-Methoxy-ethylamino)-pyridine-2-carboxylic acid {3-[(6-methyl-pyridine-2-carbonyl)-amino]-adamantan-1-yl}-amide |

TABLE 2-continued

| EXAMPLE | STRUCTURE | CHEMICAL NAME |
|---|---|---|
| 236 | 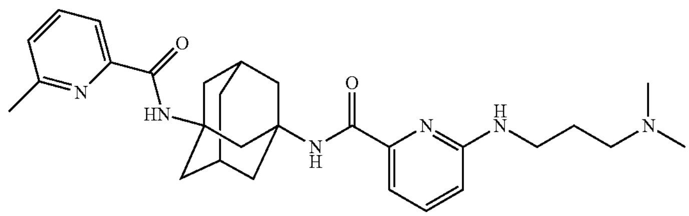 | 6-(3-Dimethylamino-propylamino)-pyridine-2-carboxylic acid {3-[(6-methyl-pyridine-2-carbonyl)-amino]-adamantan-1-yl}-amide |
| 237 | 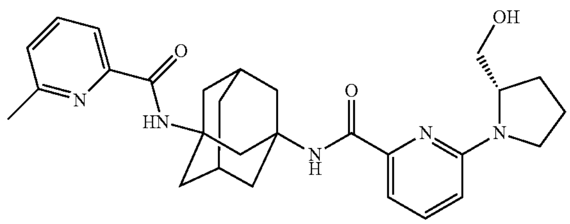 | 6-((S)-2-Hydroxymethyl-pyrrolidin-1-yl)-pyridine-2-carboxylic acid {3-[(6-methyl-pyridine-2-carbonyl)-amino]-adamantan-1-yl}-amide |
| 238 | 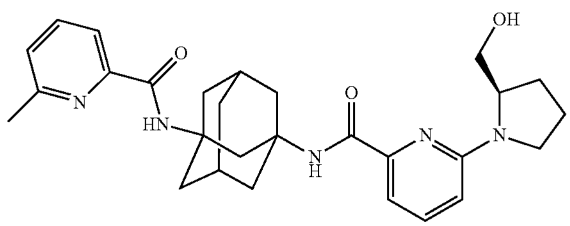 | 6-((R)-2-Hydroxymethyl-pyrrolidin-1-yl)-pyridine-2-carboxylic acid {3-[(6-methyl-pyridine-2-carbonyl)-amino]-adamantan-1-yl}-amide |
| 239 | 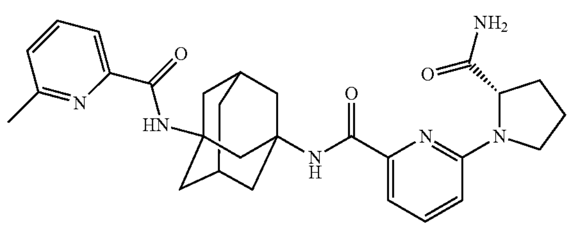 | 6-((S)-2-Carbamoyl-pyrrolidin-1-yl)-pyridine-2-carboxylic acid {3-[(6-methyl-pyridine-2-carbonyl)-amino]-adamantan-1-yl}-amide |
| 240 | 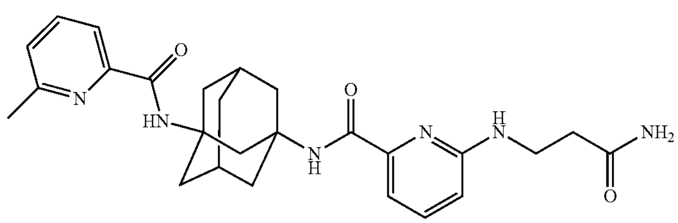 | 6-(2-Carbamoyl-ethylamino)-pyridine-2-carboxylic acid {3-[(6-methyl-pyridine-2-carobnyl)-amino]-adamantan-1-yl}-amide |
| 241 | 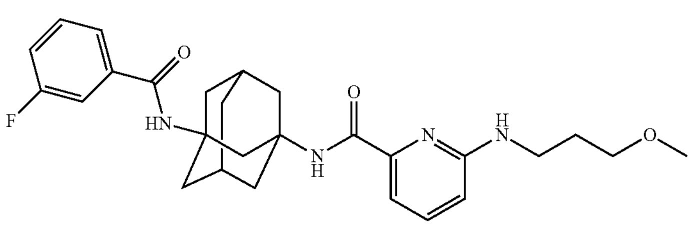 | 6-(3-Methoxy-propylamino)-pyridine-2-carboxylic acid [3-(3-fluoro-benzoylamino)-adamantan-1-yl]-amide |
| 242 | 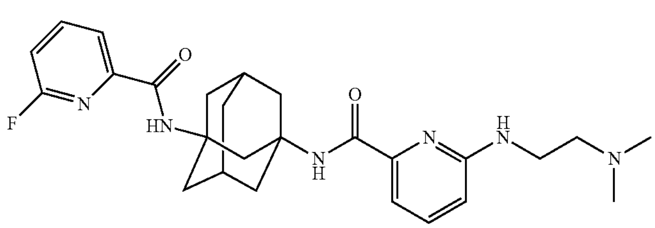 | 6-(2-Dimethylamino-ethylamino)-pyridine-2-carboxylic acid [3-(3-fluoro-benzoylamino)-adamantan-1-yl]-amide |

TABLE 2-continued

| EXAMPLE | STRUCTURE | CHEMICAL NAME |
|---|---|---|
| 243 | 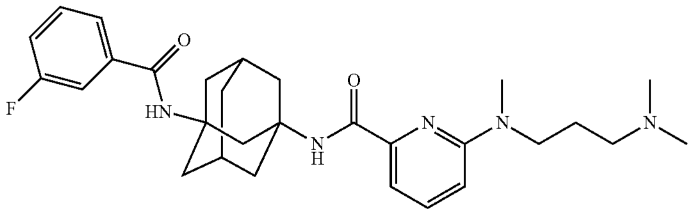 | 6-[(3-Dimethylamino-propyl)-methyl-amino]-pyridine-2-carboxylic acid [3-(3-fluoro-benzoylamino)-adamantan-1-yl]-amide |
| 244 | 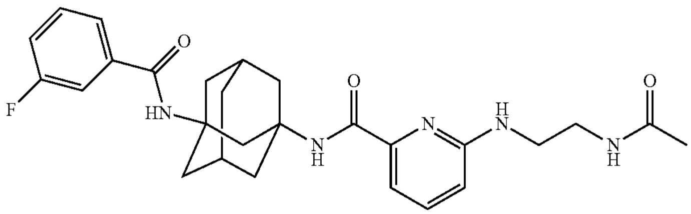 | 6-(2-Acetylamino-ethylamino)-pyridine-2-carboxylic acid [3-(3-fluoro-benzoylamino)-adamantan-1-yl]-amide |
| 245 | 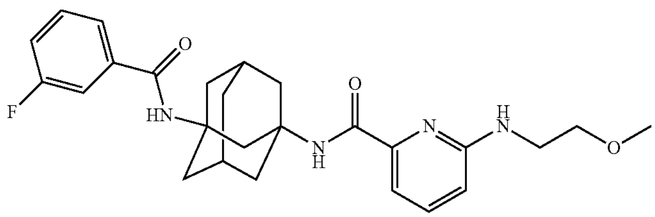 | 6-(2-Methoxy-ethylamino)-pyridine-2-carboxylic acid [3-(3-fluoro-benzoylamino)-adamantan-1-yl]-amide |
| 246 | 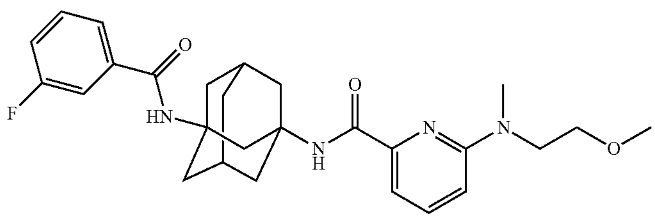 | 6-[(2-Methoxy-ethyl)-methyl-amino]-pyridine-2-carboxylic acid [3-(3-fluoro-benzoylamino)-adamantan-1-yl]-amide |
| 247 | 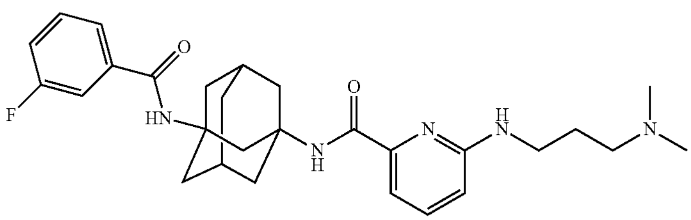 | 6-(3-Dimethylamino-propylamino)-pyridine-2-carboxylic acid [3-(3-fluoro-benzoylamino)-adamantan-1-yl]-amide |
| 248 | 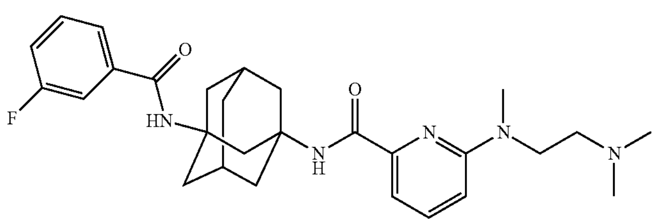 | 6-[(2-Dimethylamino-ethyl)-methyl-amino]-pyridine-2-carboxylic acid [3-(3-fluoro-benzoylamino)-adamantan-1-yl]-amide |
| 249 | 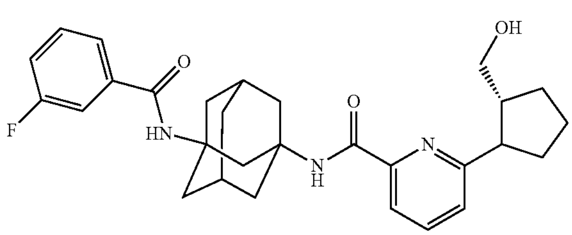 | 6-((S)-2-Hydroxymethyl-pyrrolidin-1-yl)-pyridine-2-carboxylic acid [3-(3-fluoro-benzoylamino)-adamantan-1-yl]-amide |

TABLE 2-continued

| EXAMPLE | STRUCTURE | CHEMICAL NAME |
|---|---|---|
| 250 | 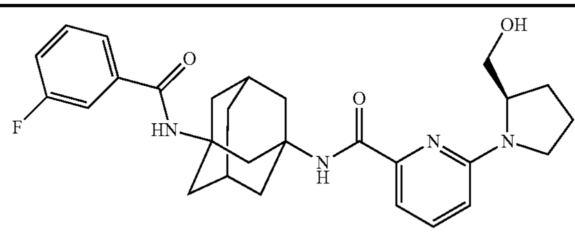 | 6-((R)-2-Hydroxymethyl-pyrrolidin-1-yl)-pyridine-2-carboxylic acid [3-(3-fluoro-benzoylamino)-adamantan-1-yl]-amide |
| 251 | 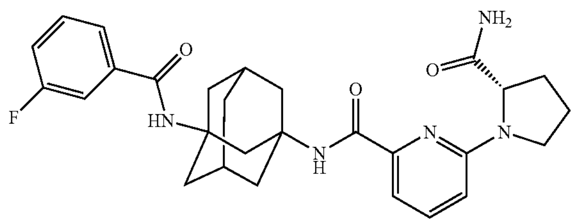 | 6-((S)-2-Carbamoyl-pyrrolidin-1-yl)-pyridine-2-carboxylic acid [3-(3-fluoro-benzoylamino)-adamantan-1-yl]-amide |
| 252 | 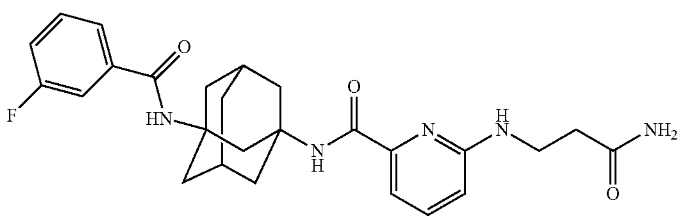 | 6-(2-Carbamoyl-ethylamino)-pyridine-2-carboxylic acid [3-(3-fluoro-benzoylamino)-adamantan-1-yl]-amide |
| 253 | 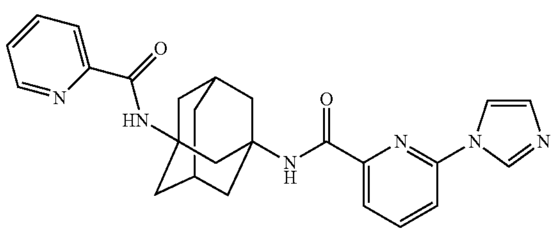 | 6-Imidazol-1-yl-pyridine-2-carboxylic acid {3-[(pyridine-2-carbonyl)-amino]-adamantan-1-yl}-amide |
| 254 | 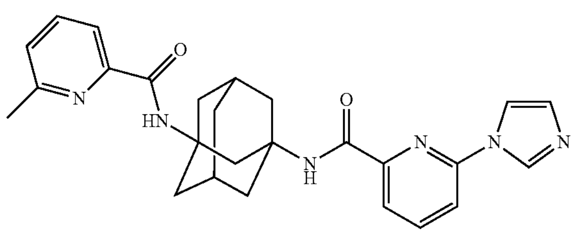 | 6-Imidazol-1-yl-pyridine-2-carboxylic acid {3-[(6-methyl-pyridine-2-carbonyl)-amino]-adamantan-1-yl}-amide |
| 255 | 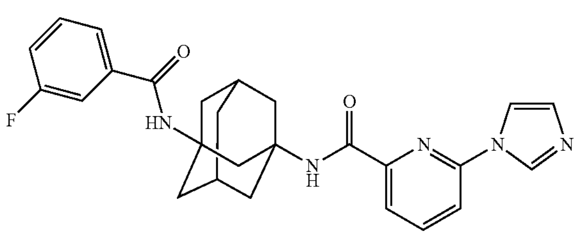 | 6-Imidazol-1-yl-pyridine-2-carboxylic acid [3-(3-benzoylamino)-adamantan-1-yl]-amide |

Examples 256 and 257 in Table 3 (below) were made via Scheme 3 from Intermediate 8 and commercially available 6-(4-fluoro-phenyl)-pyrimidine-4-carboxylic acid and 6-phenyl-pyrimidine-4-carboxylic acid, respectively, on a 0.05 mmol scale.

TABLE 3

| Example | STRUCTURE | CHEMICAL NAME |
|---|---|---|
| 256 | 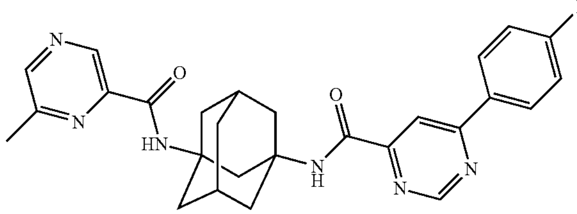 | 6-(4-Fluoro-phenyl)-pyrimidine-4-carboxylic acid {3-[(6-methyl-pyrazine-2-carbonyl)-amino]-adamantan-1-yl}-amide |
| 257 | 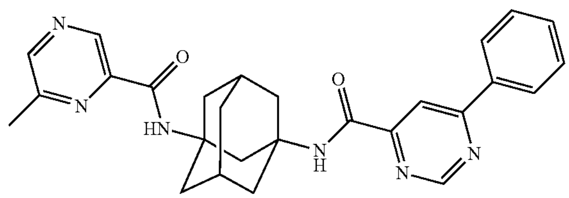 | 6-Phenyl-pyrimidine-4-carboxylic acid {3-[(6-methyl-pyrazine-2-carbonyl)-amino]-adamantan-1-yl}-amide |

4. Hypothetical Compounds of the Invention

In a similar manner to Example 58, Examples 258-279 in Table 4 (below) can be made from aryl or heteroaryl carboxylic acids via the process of Schemes 3 and 5. Non-commercially available carboxylic acids, such as 4-methyl-pyrimidine-2-carboxylic acid, 2-methyl-pyrimidine-4-carboxylic acid, 4-trifluoromethyl-pyrimidine-2-carboxylic acid, 2-trifluoromethyl-pyrimidine-4-carboxylic acid, 6-trifluoromethyl-pyrazine-2-carboxylic acid, and 5-trifluoromethyl-pyrazine-2-carboxylic acid, can be readily made from commercially available heteroaryl-chlorides, such as 2-chloro-4-methyl-pyrimidine, 4-chloro-2-methyl-pyrimidine, 2-chloro-4-trifluoromethyl-pyrimidine, 4-chloro-2-trifluoromethyl-pyrimidine, 2-chloro-6-trifluoromethyl-pyrazine, and 2-chloro-5-trifluoromethyl-pyrazine, via the process of Scheme 11, in a similar manner to the synthesis of Intermediate 11, 4-trifluoromethyl-pyrimidine-2-carboxylic acid, and of Intermediate 12, 4-methyl-pyrimidine-2-carboxylic acid.

Example 280

6-Methyl-pyrazine-2-carboxylic acid {3-[3-(2-hydroxy-ethoxy)-benzoylamino]-adamantan-1-yl}-amide

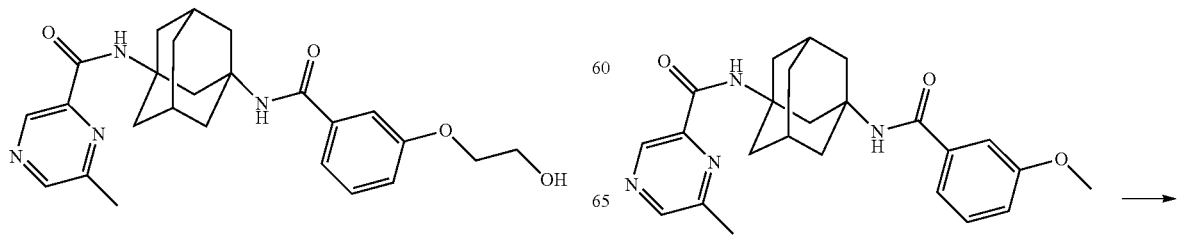

Example 280 can be made via the process of Scheme 9, supra, as follows:

Step 1: 6-Methyl-pyrazine-2-carboxylic acid [3-(3-methoxy-benzoylamino)-adamantan-1-yl]-amide

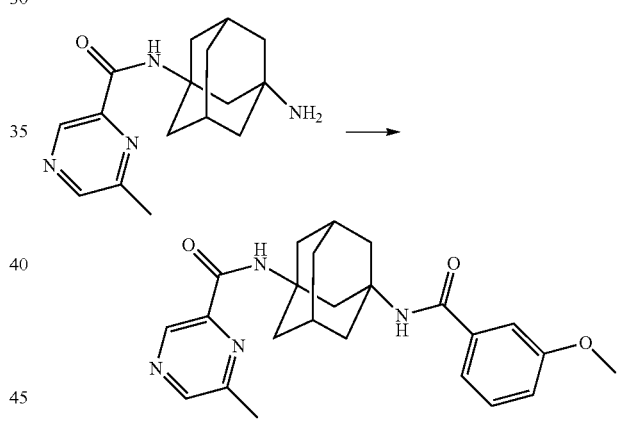

6-Methyl-pyrazine-2-carboxylic acid [3-(3-methoxy-benzoylamino)-adamantan-1-yl]-amide can be made from customary amidation of commercially available 3-methoxybenzoic acid and Intermediate 8,6-methyl-pyrazine-2-carboxylic acid (3-amino-adamantan-1-yl)-amide.

Step 2: 6-Methyl-pyrazine-2-carboxylic acid [3-(3-hydroxy-benzoylamino)-adamantan-1-yl]-amide

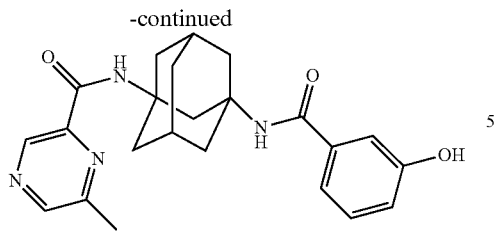

6-Methyl-pyrazine-2-carboxylic acid [3-(3-hydroxy-benzoylamino)-adamantan-1-yl]-amide can be readily made by treatment of 6-methyl-pyrazine-2-carboxylic acid [3-(3-methoxy-benzoylamino)-adamantan-1-yl]-amide with BBr₃ in DCM.

Step 3: 6-Methyl-pyrazine-2-carboxylic acid {3-[3-(2-hydroxy-ethoxy)-benzoylamino]-adamantan-1-yl}-amide

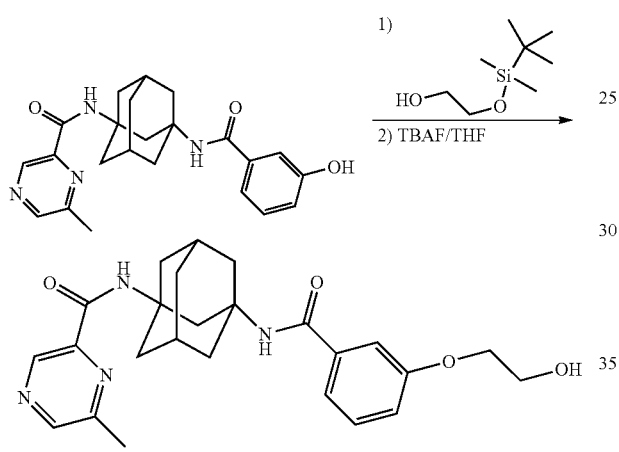

Customary Mitsunobu reaction of 6-Methyl-pyrazine-2-carboxylic acid [3-(3-hydroxy-benzoylamino)-adamantan-1-yl]-amide and 2-(t-butyldimethylsiloxy)-ethanol, followed by deprotection of the t-butyldimethylsiloxy group by treatment with tetrabutylammonium fluoride (TBAF) could afford the title compound, 6-methyl-pyrazine-2-carboxylic acid {3-[3-(2-hydroxy-ethoxy)-benzoylamino]-adamantan-1-yl}-amide.

Example 281 in Table 4 (below) can be made in a similar manner to Example 280.

Example 282

6-Methyl-pyrazine-2-carboxylic acid {3-[3-(2-hydroxy-2-methyl-propoxy)-benzoylamino]-adamantan-1-yl}-amide

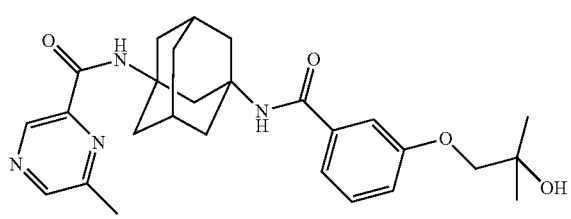

Example 282 can be made from 6-methyl-pyrazine-2-carboxylic acid [3-(3-hydroxy-benzoylamino)-adamantan-1-yl]-amide (step 2, Example 280):

Step 1: 6-Methyl-pyrazine-2-carboxylic acid {3-[3-(2-oxo-propoxy)-benzoylamino]-adamantan-1-yl}-amide

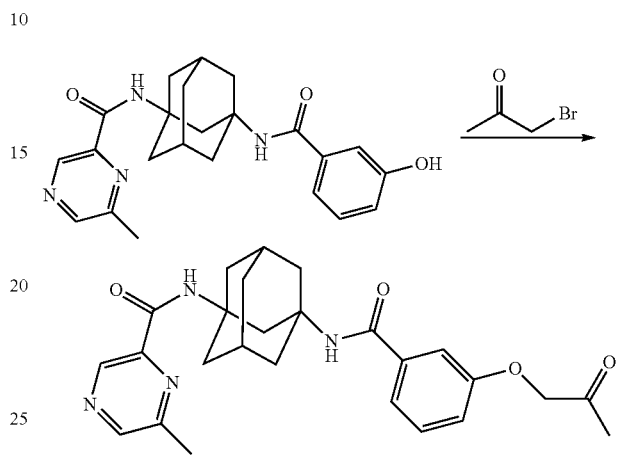

Alkylation of 6-methyl-pyrazine-2-carboxylic acid [3-(3-hydroxy-benzoylamino)-adamantan-1-yl]-amide (step 2, Example 280) with 1-bromo-propan-2-one in DMF under basic conditions, such as Cs₂CO₃ at 60° C., could afford the title compound, 6-methyl-pyrazine-2-carboxylic acid {3-[3-(2-oxo-propoxy)-benzoyl-amino]-adamantan-1-yl}-amide.

Step 2: 6-Methyl-pyrazine-2-carboxylic acid {3-[3-(2-hydroxy-2-methylpropoxy)-benzoylamino]-adamantan-1-yl}-amide

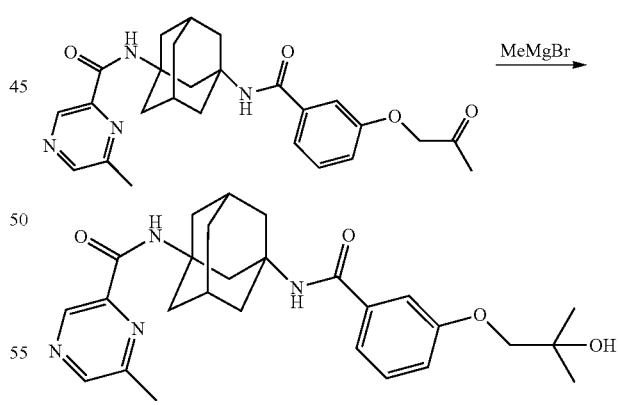

Reaction of 6-methyl-pyrazine-2-carboxylic acid {3-[3-(2-oxo-propoxy)-benzoyl-amino]-adamantan-1-yl}-amide with MeMgBr in THF or ether at 0° C. could yield the title compound, 6-methyl-pyrazine-2-carboxylic acid {3-[3-(2-hydroxy-2-methylpropoxy)-benzoylamino]-adamantan-1-yl}-amide.

Example 283 in Table 4 (below) can be made in a similar manner to Example 282.

TABLE 4

| EXAMPLE | STRUCTURE | CHEMICAL NAME |
|---|---|---|
| 258 | 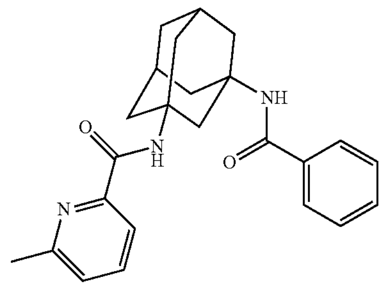 | 6-Methyl-pyridine-2-carboxylic acid (3-benzoylamino-adamantan-1-yl)-amide |
| 259 | 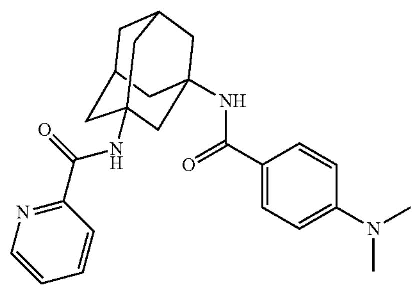 | Pyridine-2-carboxylic acid [3-(4-dimethylamino-benzoylamino)-adamantan-1-yl]-amide |
| 260 | 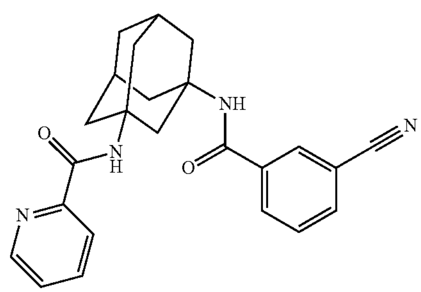 | Pyridine-2-carboxylic acid [3-(3-cyano-benzoylamino)-adamantan-1-yl]-amide |
| 261 | 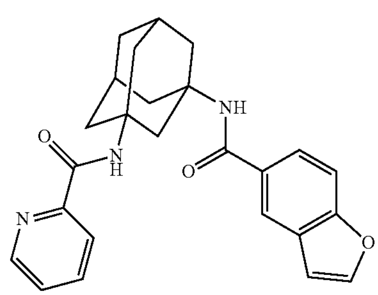 | Pyridine-2-carboxylic acid {3-[(benzofuran-5-carbonyl)-amino]-adamantan-1-yl}-amide |
| 262 | 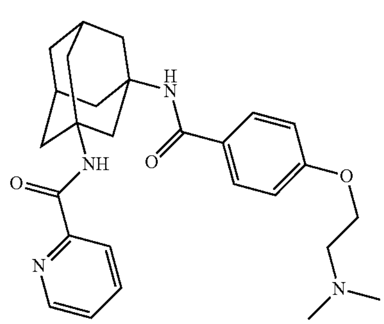 | Pyridine-2-carboxylic acid {3-[4-(2-dimethylamino-ethoxy)-benzoylamino]-adamantan-1-yl}-amide |

TABLE 4-continued

Hypothetical Compounds

| EXAMPLE | STRUCTURE | CHEMICAL NAME |
|---|---|---|
| 263 | 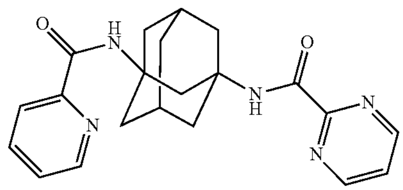 | Pyrimdiine-2-carboxylic acid {3-[(pyridine-2-carbonyl)-amino]-adamantan-1-yl}-amide |
| 264 | 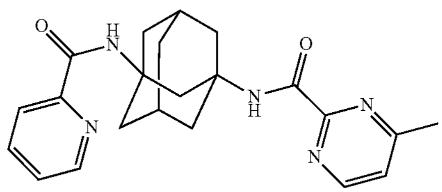 | 4-Methyl-pyrimidine-2-carboxylic acid {3-[(pyridine-2-carbonyl)-amino]-adamantan-1-yl}-amide |
| 265 | 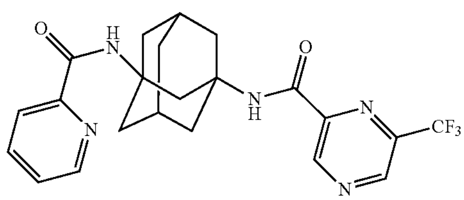 | 6-Trifluoromethyl-pyrazine-2-carboxylic acid {3-[(pyridine-2-carbonyl)-amino]-adamantan-1-yl}-amide |
| 266 | 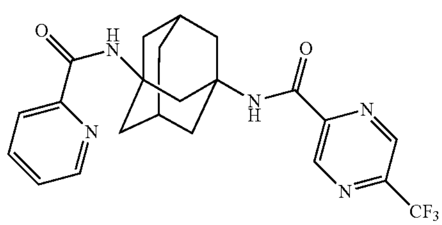 | 5-Trifluoromethyl-pyrazine-2-carboxylic acid {3-[(pyridine-2-carbonyl)-amino]-adamantan-1-yl}-amide |
| 267 | 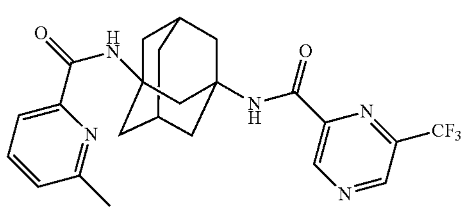 | 6-Trifluoromethyl-pyrazine-2-carboxylic acid {3-[(6-methyl-pyridine-2-carbonyl)-amino]-adamantan-1-yl}-amide |
| 268 | 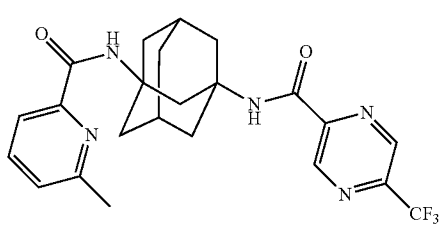 | 5-Trifluoromethyl-pyrazine-2-carboxylic acid {3-[(6-methyl-pyridine-2-carbonyl)-amino]-adamantan-1-yl}-amide |
| 269 | 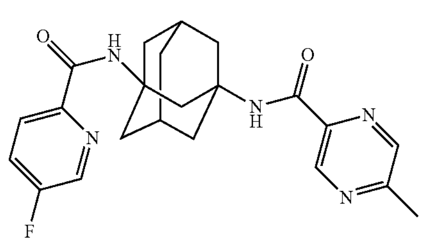 | 5-Methyl-pyrazine-2-carboxylic acid {3-[(5-fluoro-pyridine-2-carbonyl)-amino]-adamantan-1-yl}-amide |

TABLE 4-continued

Hypothetical Compounds

| EXAMPLE | STRUCTURE | CHEMICAL NAME |
|---|---|---|
| 270 | 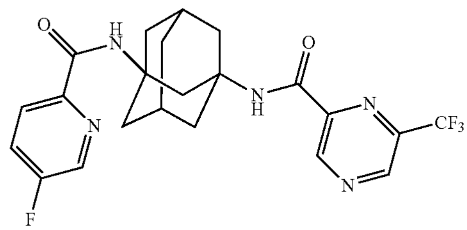 | 6-Trifluoromethyl-pyrazine-2-carboxylic acid {3-[(5-fluoro-pyridine-2-carbonyl)-amino]-adamantan-1-yl}-amide |
| 271 | 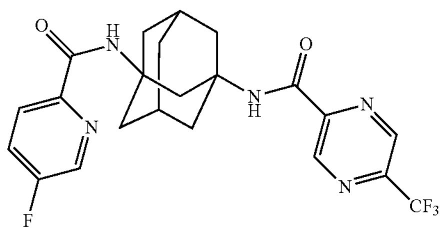 | 5-Trifluoromethyl-pyrazine-2-carboxylic acid {3-[(5-fluoro-pyridine-2-carbonyl)-amino]-adamantan-1-yl}-amide |
| 272 | 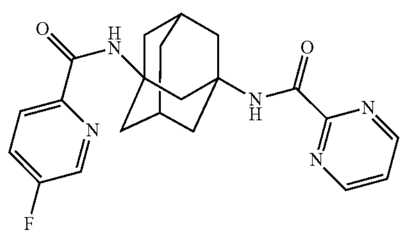 | Pyrimidine-2-carboxylic acid {3-[(5-fluoro-pyridine-2-carbonyl)-amino]-adamantan-1-yl}-amide |
| 273 | 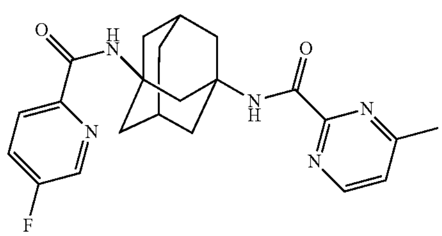 | 4-Methyl-pyrimidine-2-carboxylic acid {3-[(5-fluoro-pyridine-2-carbonyl)-amino]-adamantan-1-yl}-amide |
| 274 | 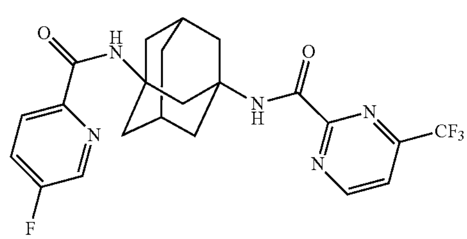 | 4-Trifluoromethyl-pyrimidine-2-carboxylic acid {3-[(5-fluoro-pyridine-2-carbonyl)-aminio]-adamantan-1-yl}-amide |
| 275 | 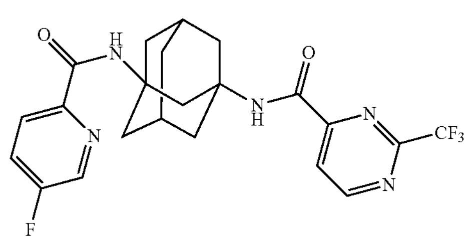 | 2-Trifluoromethyl-pyrimidine-4-carboxylic acid {3-[(5-fluoro-pyridine-2-carbonyl)-amino]-adamantan-1-yl}-amide |

TABLE 4-continued

Hypothetical Compounds

| EXAMPLE | STRUCTURE | CHEMICAL NAME |
|---|---|---|
| 276 | 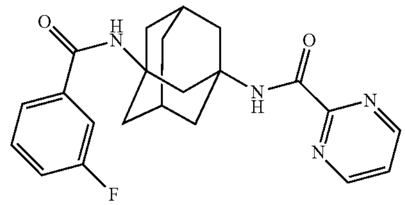 | Pyrimidine-2-carboyxlic acid [3-(3-fluoro-benzoylamino)-adamantan-1-yl]-amide |
| 277 | 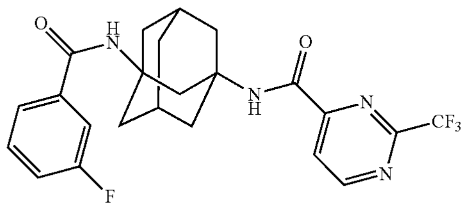 | 2-Trifluoromethyl-pyrimidine-4-carboxylic acid [3-(3-fluoro-benzoylamino)-adamantan-1-yl]-amide |
| 278 | 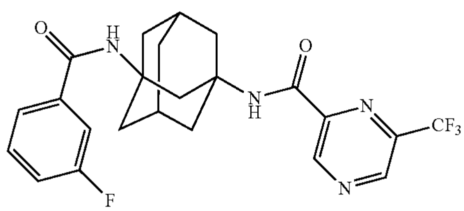 | 6-Trifluoromethyl-pyrazine-2-carboxylic acid [3-(3-fluoro-benzoylamino)-adamantan-1-yl]-amide |
| 279 | 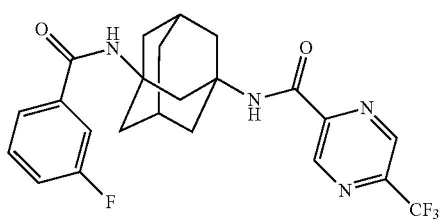 | 5-Trifloromethyl-pyrazine-2-carboxylic acid [3-(3-fluoro-benzoylamino)-adamantan-1-yl]-amide |
| 280 | 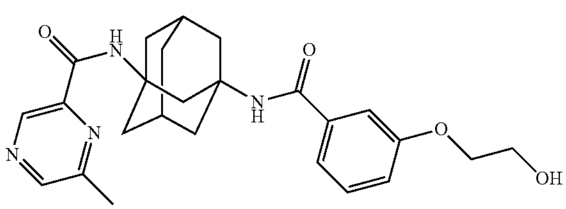 | 6-Methyl-pyrazine-2-carboxylic acid {3-[3-(2-hydroxy-ethoxy)-benzoylamino]-adamantan-1-yl}-amide |
| 281 | 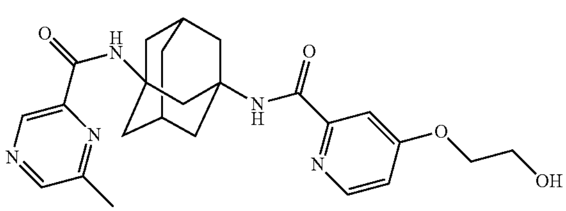 | 6-Methyl-pyrazine-2-carboxylic acid (3-{[4-(2-hydroxy-ethoxy)-pyridine-2-carbonyl]-amino}-adamantan-1-yl)-amide |
| 282 | 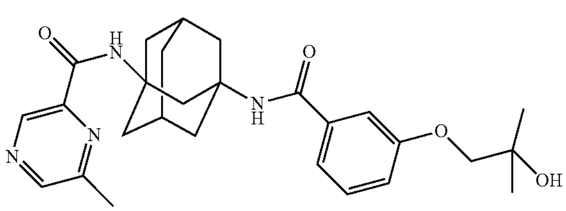 | 6-Methyl-pyrazine-2-carboxylic acid {3-[3-(2-hydroxy-2-methyl-propoxy)-benzoylamino]-adamantan-1-yl}-amide |

TABLE 4-continued

Hypothetical Compounds

| EXAMPLE | STRUCTURE | CHEMICAL NAME |
|---|---|---|
| 283 | 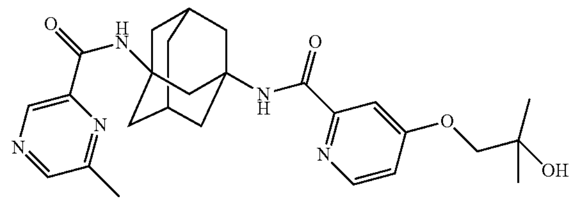 | 6-Methyl-pyrazine-2-carboxylic acid (3-{[4-(2-hydroxy-2-methyl-propoxy)-pyridine-2-carbonyl]-amino}-adamantan-1-yl)-amide |

5. Pharmacological Evaluation of Compounds of the Invention

Compounds of the present invention have been tested in vitro and in vivo, and can be tested in vitro and in vivo, in the assays as described below.

In Vitro Assays

Radioligand Binding Assays

Binding assays were performed as described in [J. A. O'Brien et al. Mol. Pharmacol., 2003, 64, 731-740] with slight modifications. Briefly, after thawing, the membrane homogenates were resuspended in 50 mM Tris-HCl, 0.9% NaCl binding buffer at pH 7.4 to a final assay concentration of 40 μg protein/well for [$^3$H]methoxy-5-(2-pyridinylethynyl)pyridine ([$^3$H] MPEP) (American Radiolabeled Chemicals, Inc., St. Louis, Mo.) filtration binding. Incubations included 5 nM [$^3$H] MPEP, membranes and either buffer or varying concentrations of compound. Samples were incubated for 60 min at room temperature with shaking. Non-specific binding was defined with 10 μM MPEP. After incubation, samples were filtered over a GF/C filter (presoaked in 0.25% polyethyleneimine (PEI)) and then washed 4 times using a Tomtec° Harvester 96° Mach III cell harvester (Tomtec, Hamden, Conn.) with 0.5 mL ice-cold 50 mM Tris-HCl (pH 7.4).

$IC_{50}$ values were derived from the inhibition curve and $K_i$ values were calculated according to the Cheng and Prusoff equation of $K_i=IC_{50}/(1+[L]/K_d)$ described in [Y. Cheng and W. H. Prusoff Biochem. Pharmacol. 1973, 22, 3099-3108] where [L] is the concentration of radioligand and $K_d$ is its dissociation constant at the receptor, derived from the saturation isotherm. The $K_i$ value for Examples 1 and 2 were 6.7 and 40 nM, respectively. Examples 19, 42, 44, 58, 65, 67, 69, 72, 74, 79, 93, 94, 95, 96, 105, 107, 119 and 120, have Ki values ranging from 6 to 700 nM.

Calcium Mobilization Assay to Test for Negative or Positive Allosteric Activity

The cDNA for rat metabotropic glutamate receptor 5 (rmGluR5) was a generous gift from S. Nakanishi (Kyoto University, Kyoto, Japan). The rmGluR5 was stably expressed in a HEK 293 cell line and grown in Dulbecco's Modified Eagle Medium (DMEM) (Invitrogen, Carlsbad, Calif.) with supplements (10% bovine calf serum, 4 mM glutamine, 100 units/mL penicillin, 100 μg/mL streptomycin and 0.75 mM G1418) at 37° C., 5% $CO_2$. Twenty-four hours prior to assay, cells were seeded into 384-well black wall microtiter plates coated with poly-D-lysine. Just prior to assay, media was aspirated and cells dye-loaded (25 μL/well) with 3 μM Fluo-4/0.01% pluronic acid in assay buffer (Hank's Balanced Saline Solution (HBSS)): 150 mM NaCl, 5 mM KCl, 1 mM $CaCl_2$, 1 mM $MgCl_2$, plus 20 mM N-2-Hydroxyethylpiperazine-N'-2-ethanesulfonic acid (HEPES), pH 7.4, 0.1% bovine serum albumin (BSA) and 2.5 mM probenicid) for 1 hour in 5% $CO_2$ at 37° C. After excess dye was discarded, cells were washed in assay buffer and layered with a final volume equal to 30 μL/well. Basal fluorescence is monitored in a fluorometric imaging plate reader (FLIPR) (Molecular Devices, Sunnyvale, Calif.) with an excitation wavelength of 488 nm and an emission range of 500 to 560 nm. Laser excitation energy was adjusted so that basal fluorescence readings were approximately 10,000 relative fluorescent units. Cells were stimulated with an $EC_{20}$ or an $EC_{80}$ concentration of glutamate in the presence of a compound to be tested, both diluted in assay buffer, and relative fluorescent units were measured at defined intervals (exposure=0.6 sec) over a 3 min period at room temperature. Basal readings derived from negative controls were subtracted from all samples. Maximum change in fluorescence was calculated for each well. Concentration-response curves derived from the maximum change in fluorescence were analyzed by nonlinear regression (Hill equation). A negative modulator can be identified from these concentration-response curves if a compound produces a concentration dependent inhibition of the $EC_{80}$ glutamate response. Exemplified compounds Examples 1-10 were tested in the above assay for negative allosteric modulation: FLIPR maximum inhibition ranged 90% to 99% while FLIPR $IC_{50}$ ranged from 0.9 nM to 1300 nM. Examples 11-163 also were tested in the above assay. For Examples 11-104, FLIPR maximum inhibition ranged from 63% to 99%, while FLIPR $IC_{50}$ ranged from 0.7 nM to 600 nM; and for Examples 105-163, FLIPR maximum inhibition ranged from 70% to 99%, while FLIPR $IC_{50}$ ranged from 0.7 nM to 1800 nM. Examples 164-178, 181-182, 184-187, 189-194, 196, 197-255 were tested in the above assay for negative allosteric modulation: FLIPR maximum inhibition ranged 63% to 99% while FLIPR $IC_{50}$ ranged from 0.4 nM to 1300 nM.

A positive modulator can be identified from these concentration-response curves if a compound produces a concentration dependent increase in the $EC_{20}$ glutamate response. Examples 256-257 exhibited positive modulation, having FLIPR $EC_{50}$ of 300 nM and 830 nM, and maximum modulation of 170% and 120%, respectively.

In Vivo Assays

Examples 1, 2 and 58 were evaluated in vivo for anxiolytic effects using (1) mouse marble burying (mMB) methods similar to those described in [K. Njung'e, K. and S. L. Handley, Pharmacology, Biochemistry and Behavior, 1991, 38, 63-67] and (2) a modified Geller-Seifter conflict test described in [N. A. Moore et al. Behavioural Pharmacology. 1994, 5, 196-202].

More specifically for the mMB testing, adult, male CD1 mice (Charles River Laboratories (Kingston, N.Y.)), weighing 25 to 30 g, were used. All animals were group-housed in a standard colony room with a 12:12 light/dark cycle (lights on at 6:00 am) for at least one week prior to testing. Food and water were provided ad libitum. Animals were weighed, tail marked, and randomly assigned to treatment groups before testing.

For each test, sixty minutes after the injection of vehicle or test compound, or 30 min after injection of the positive control, buspirone, mice were individually placed into test cages containing 1.5 in of Aspen bedding (PWI brand) and two rows of 10 marbles (20 marbles per test cage total). Filter tops were used to cover each test cage. Thirty minutes later, mice were removed from test cages and returned to their home cages. The number of fully visible marbles (less than ⅔ covered with bedding) were counted and subtracted from 20 to arrive at the number of marbles buried. Twelve mice were tested per group.

Testing included multiple tests with each test performed to evaluate buspirone hydrochloride (BUS; Sigma Aldrich) (positive control) and/or a compound of the present invention. Each compound was dissolved immediately prior to testing in 20% beta-cyclodextrin (compound of the present invention) or distilled water (BUS) and administered at one or more doses (such as 3, 10, and/or 30 mg/kg) via subcutaneous (SC) or intraperitoneal (IP) injection at the indicated pretreatment times (i.e., 30, 60, or 120 min pretreatment). Doses were measured in mg drug (salt form) per kg body weight. Data was analyzed using one-way ANOVA with post-hoc Dunnett's test.

More specifically for the Geller-Seifter Conflict testing, rodent operant chambers (ENV-007CT, Med Associates Inc. (Georgia, Vt.)) and sound-attenuating chambers (ENV-018MD, Med Associates Inc.) were used. Each chamber was equipped with a house light, cue lights, grid floor to deliver foot shocks via a programmable shocker, (ENV-414, Med Associates, Inc.) and food hopper. Two levers were located on either side of the food hopper. Rats were trained to only respond on the left lever. Food reinforcement was used (Dustless Precision Pellets, 45 mg, BioServ, (Frenchtown, N.J.)). MED-PCIV software (Med Associates) was used to run experimental sessions and collect data.

Prior to beginning the Conflict procedure, animals were initially trained to lever press on fixed ratio schedules (FR 1, 2, 5, and 10). Once animals obtained 25 rewards on a FR 10 schedule for 2 consecutive days, animals began training on a three component Conflict schedule. The three components were as follows: (1) an unpunished, variable interval 30 s (VI30) schedule of food reinforcement to reinforce lever pressing on a variable time schedule that averaged 30 s; this period had a duration of 9 minutes and was signaled by illumination of the rear house light only; (2) immediately following was a 3 minute time out period (TO) that was signaled by total darkness; responding was recorded but was neither rewarded nor punished; (3) a punished, fixed ratio 10 (FR10) schedule of reinforcement that simultaneously presented food and foot shock (0.3 mA, 500 ms) on every tenth lever press during a 3 minute period; this component was signaled by illumination of the rear house light and cue lights above each lever. These three components were repeated twice in the same order during the daily 30 minute session.

Testing began when stable rates of responding were observed for 5 days (no significant trends up or down). Animals were tested using a Latin-squares design, on Wednesdays and Fridays. Animals served as their own controls and received all treatments. To maintain baseline performance, animals were also trained the remaining three weekdays.

Testing was performed using 12 adult, male Sprague-Dawley rats, weighing 426-567 g (Charles River Laboratories (Kingston, N.Y.)). Animals were pair-housed in colony rooms maintained at controlled temperature (68-72° F.) and a 12-h light/dark cycle (lights on 06:00). Animals were given free access to water, while food was limited to 15 g of Bacon Lover's Treats (BioServ) after training/testing Monday through Thursday. Friday through Sunday, animals had free access to Lab Diet 5012 Rat Diet (PMI Nutrition International, LLC, Brentwood, Mo.) until cages were changed and food removed on Sunday.

Testing included multiple tests where each test was performed to evaluate either a reference compound or a compound of the present invention. Reference anxiolytics included chlordiazepoxide, diazepam and buspirone, which were dissolved in saline or water and administered via SC, IP, and/or PO. Test compounds were dissolved in 20% beta-cyclodextrin, and the pH was adjusted to 7 with $NaHCO_3$. For each test, the compound to be evaluated was tested at one or more doses (such as 10, 20, 30 and/or 50 mg/kg) via p.o. administration 60 minutes before the test using an injection volume of 2 mL/kg in comparison with a vehicle control group. Doses were measured in mg drug (salt form) per kg body weight. Data was analyzed using Repeated Measures ANOVA with post-hoc Dunnett's test.

Compounds of the invention have significant anxiolytic activity. For example, Example 1 showed significant activity in both assays (mMB EDmin 3 mg/kg; Geller-Seifter EDmin 10 mg/kg). Example 2 also showed significant activity in both assays (mMB EDmin 30 mg/kg, Geller-Seifter EDmin 20 mg/kg). Example 58 showed significant activity in both assays (mMB EDmin 10 mg/kg, SC; Geller-Seifter EDmin 10 mg/kg, PO); and as shown in the following tables.

TABLE 5

Statistically Significant Active Dose(s) of Representative Compounds of the Present Invention in Mouse Marble Burying Assay

| Example | Active Dose mg/kg (SC injection) | Statistical significance[+] |
|---------|----------------------------------|------------------------------|
| 1 | 3, 10, 30 | $F(4, 55) = 19.6, p < 0.01$ |
| 2 | 30 | $F(4, 55) = 7.2, p < 0.01$ |
| 41 | 10, 30 | $F(4, 55) = 17, p < 0.01$ |
| 58 | 10, 30 | $F(4, 55) = 19, p < 0.01$ |
| 63 | 30 | $F(4, 55) = 5.7, p < 0.05$ |
| 93 | 30 | $F(4, 54) = 6.6, p < 0.01$ |
| 94 | 3, 10, 30 | $F(4, 55) = 46, p < 0.01$ |
| 95 | 10, 30 | $F(4, 55) = 18, p < 0.01$ |
| 96 | 10, 30 | $F(4, 55) = 30, p < 0.01$ |
| 105 | 30 | $F(4, 55) = 11, p < 0.01$ |
| 107 | 10 | $t(22) = 17, p < 0.01$ |
| 119 | 10 | $t(22) = 25, p < 0.01$ |
| 145 | 30 | $F(4,54) = 10, p < 0.01$ |
| 179 | 10 | $t(22) = 6, p < 0.01$ |
| 183 | 10 | $t(22) = 4, p < 0.01$ |
| 185 | 30 | $F(4, 55) = 15, p < 0.01$ |
| 191 | 10, 30 | $F(4, 55) = 11, p < 0.01$ |

[+]Statistical significance was determined using one-way ANOVA with post-hoc Dunnett's test or paired students t-test

TABLE 6

Statistically Significant Active Dose(s) of Representative Compounds of the Present Invention in Geller-Seifter Assay

| Example | Active dose(s) mg/kg (oral injection) | Statistical significance[+] |
|---------|---------------------------------------|------------------------------|
| 1 | 50 | $t(7) = 2.99, p < 0.05$ |
| 2 | 20 | $t(7) = 2.4, p < 0.05$ |
| 41 | 30 | $F(3, 7) = 11.6, p < 0.01$ |
| 58 | 10, 20 | $F(3, 11) = 8, p < 0.05$ |

TABLE 6-continued

Statistically Significant Active Dose(s) of Representative
Compounds of the Present Invention in Geller-Seifter Assay

| Example | Active dose(s) mg/kg (oral injection) | Statistical significance[+] |
|---|---|---|
| 94 | 20 | $F(3, 8) = 2.7$, $p < 0.05$ |
| 95 | 10, 30 | $F(3, 9) = 5.7$, $p < 0.05$ |

[+]Statistical significance was determined using one-way ANOVA with post-hoc Dunnett's test or paired students t-test Compounds of the present invention were evaluated in vivo for antidepressive effects. An assessment of depression-like actions was measured using a forced swim test similar to that described in [J. F. Cryan, et al. Neuroscience and Biobehavioral Reviews 2005, 29, 547-569.] Animals used for testing were adult, male NIH Swiss Webster mice (Harlan Laboratories (Frederick, Md.)), weighing 22 to 24 g, which were acclimatized and housed as previously described with the mice used in the mMB tests.

For the mouse Forced Swim Test (mFST), mice were individually placed into clear Pyrex® cylinders (11 cm diameter, 16.5 cm height) containing 11 cm deep tap water (23-25° C.) sixty min after the injection of vehicle or test compound, or 30 min after injection of the positive control, imipramine hydrochloride (IMI; Sigma Aldrich, St. Louis, Mo.). Imipramine was prepared with isotonic saline and test compounds were prepared as described previously with mMB tests. Doses used were as described previously with mMB tests. The percentage of time spent floating, swimming, and struggling ("climbing") was measured during a 6 min session. Swim sessions were video monitored and analyzed in real-time using the Biobserve Automated FST apparatus and software (Biobserve GmbH, Bonn, Germany). Group size ranged from twelve to thirteen mice. Doses were measured in mg drug (salt form) per kg body weight. Data was analyzed using one-way ANOVA with post-hoc Dunnett's test.

Compounds of the present invention had significant antidepressive effects in the mFST at 3 mg/kg, 10 mg/kg, 30 mg/kg, or a combination thereof. (Statistical significance ($p<0.05$) was determined using one-way ANOVA with post-hoc Dunnett's test.)

An in vivo effect of a compound of the present invention may also be evaluated by using the following, non-limiting, examples of in vivo behavioral animal models. The following behavioral models are not intended as the only models useful for determining the efficacy of a compound of the present invention to treat the corresponding disorder or disease.

Compounds of the invention also can be evaluated in vivo for anxiolytic effects using a light-enhanced startle (LES) reflex method as that described in [Walker and Davis. *Biol. Psychiatry*, 1997, 42, 461-471]. The startle response is a coordinated contraction of skeletal muscle groups in response to a high intensity unexpected stimulus. Most sensory modalities can be used, but sound is most frequently employed because it is easily controlled. Thus, when a short burst of sufficient intensity occurs (e.g., 115 dB) an involuntary startle response occurs. High light levels increase the startle response in nocturnal species such as the rat and this effect does not require any pre-conditioning. Anxiolytics—an agent that relieves anxiety—decrease light-enhanced startle.

For the LES test, an apparatus consisting of a commercially available soundproofed startle chamber (e.g., SR-LAB™ Startle Response System, San Diego Instruments, San Diego, Calif.) can be used. All experimental events and data recording can be controlled by computer program (e.g., SR-LAB™ control unit). Rats are placed within the startle chamber in a small Perspex® cylinder, slightly larger than the rat, which is attached to a base plate containing a strain gauge. Vertical movement of the rat such as occurs during a startle response results in deformation of the base plate, which generates a current in the strain gauge that is proportional to the size of the movement, i.e., the size of the startle response. A loudspeaker is placed directly above the rat to provide background sound and stimuli. A light source (2500-3500 Lux) is located in each startle chamber.

The LES test consists of two 20-minute sessions (first with lights off and then with lights on) of which the first 5 minutes are for habituation, during which background noise of 70 dB intensity is provided within the chamber. At the end of each habituation period, 10 stimulations of 110 dB are presented to habituate the animals. Thereafter, three trial types are presented in pseudo random order, 8 times each. Trials are separated by 15-25 seconds. The trial types are 100, 105 or 110 dB startle during which a 40 ms burst of white noise at 100, 105 or 110 dB is presented, resulting in a startle response. A period of 5 minutes without light or noise separates the two sessions. An appropriate rat species that can be use includes male Rj: Wister (Hans) rats (180-280 g weight at start of the testing with a maximum weight range per test of 50 g) (Elevage Janvier, Le Genest-Saint-Isle, France). The rats should be allowed to acclimatize to laboratory conditions at least 5 days before testing with free access to food and water. Acclimatization conditions should be comparable to those described in the scientific literature and/or known to those skilled in the art.

The output from the startle platform is recorded for 40 ms starting from the onset of the startle stimulus. Three variables are recorded for each trial: the average response over the whole recording period, the peak response and the time to peak response. The startle intensity is calculated for each rat by averaging the 8 trials of each type under dark or light conditions and calculating the percentage increase in startle amplitude (average and peak values) caused by light (LES). The time to peak response is a measure of reaction time.

The test is performed un-blinded using, e.g., 12 rats per group. Testing includes multiple tests where each test is performed to evaluate a reference compound (e.g., chlordiazepoxide), comparative compound (e.g., pregabalin) and/or a compound of the present invention. For example, in test 1, a known anxiolytic, such as chlordiazepoxide and pregabalin, is used, followed by test 2 using the mGluR5 antagonist 2-methyl-6-(phenylethynyl)-pyridine (MPEP), and then test 3 is performed using a compound of the present invention. Alternatively, each test can be performed concurrently, or in some combination of sequentially and concurrently. For each test, the compound to be evaluated is tested at one or more doses (such as 1, 3, 10, 30 and/or 100 mg/kg) via p.o. administration 60 minutes before the test in comparison with a vehicle control group. Prior to testing, test compounds can be tested for solubility by cold stirring of the highest intended dose for 10 min in distilled water. If soluble, distilled water can serve as the vehicle. If insoluble, the test compounds can be suspended in 0.2% hydroxypropylmethylcellulose (HPMC) in distilled water. Doses can be prepared as weight to volume (W/V) stock solutions and then serially diluted (V/V) for compounds in solution or separately weighted (W/V) for compounds in suspension.

For each test, data is analyzed by comparing treated groups with the vehicle control using unpaired Student's t tests. LES in each group will be analyzed by comparing within each treated group the intensity of startle reaction under dark and light conditions using paired Student's t tests.

The "Vogel Conflict Test" as described by Vogel et al (*Psychopharmacologia,* 1971, 21, 1-7) can be used to detect anxiolytic activity of a compound because anxiolytics increase punished drinking. In the test, rats are deprived of water for approximately 48 hours and are then placed individually into a transparent Plexiglas® enclosure (15×32×34 cm) with a floor consisting of stainless steel bars (0.4 cm) spaced 1 cm apart. The back wall of the enclosure is made of opaque Plexiglas® thereby concealing the observer from the experimental animal. In the centre of the opposite wall, 5 cm above the floor, a metal water spout protrudes into the cage and is connected to one pole of a shock generator (Apelex: Type 011346). The other pole of the shock generator is connected to the metal grid floor.

The rat is left to explore until it finds the water spout. Then, every time it drinks, it receives a slight electric shock (1.7 mA, 1 s) 2 seconds after it starts lapping. The number of punished drinks is counted during a 3 minute test.

The test is performed blind with, e.g., 10 rats per group. Testing includes multiple tests using reference compounds and compounds of the present invention that are prepared and administered as previously described LES test. Appropriate animals for testing with acclimatization conditions are, for example, the male Rj: Wistar (Hans) rats as previously described for the LES test. Data is analyzed by comparing treated groups with appropriate controls using unpaired Student's t tests.

Antidepressive effect can be evaluated using the Flinders Sensitive Line (FSL) rat in the FST and social interaction test as described in [D. H. Overstreet and G. Griebel *Pharmacol Biochem Behav.,* 2005, 82, 1: 223-227]. More specifically, compounds of the invention are tested at multiple doses (e.g., 10 mg/kg, 30 mg/kg, etc.) by preparing in 20% HP-beta-cyclodextrin and against vehicle control. In addition to an FSL vehicle control group, Flinders Resistant Line rats' vehicle control group is tested. Test compounds are administered daily by IP injection (2 mg/kg injection volume) for 14 days. Animals are tested in the social interaction and forced swim tests on Day 15, 22-24 hours after the injection on Day 14, as described in Overstreet and Griebel 2005. Six to eight animals per group are tested.

Anxiolytic and antidepressive effect can also be evaluated using a paradigm for decreased HPA axis feedback (David et al., 2007, SFN meeting in San Diego). This model based on the chronic delivery of corticosterone in the drinking water, causes anxiety- and depression-like behaviors in mice. The model consists of a sustained administration of a high dose (35 µg/mL), but not a low dose (7 µg/mL), of corticosterone for four or seven weeks. Such a treatment induced anxiety- and depression-like behaviour in C57B16/NTac mouse strain as indicated by a decreased time spent and number of entries into center of the arena during the 30 minutes open field test (OF), whereas total ambulation was unaltered. Also, the latency to feed was increased in corticosterone-treated mice submitted to the novelty suppressed feeding (NSF) paradigm. As the corticosterone treatment did not alter food-intake in the home cage (familiar environment), changes in feeding latency were not due to changes in appetite or an underlying metabolic abnormality. Importantly, the adrenocorticotropic hormone (ACTH) and corticosterone (CORT) response to an acute stressor (6 min forced swim test (FST)), measured as plasma-concentrations, was blunted in C57BL/6NTac mice. Theses results were confirmed in CD1 strain mice. Three weeks treatment with the antidepressant imipramine (40 mg/kg/day ip) and fluoxetine (18 mg/kg/day ip) reversed the anxiety- and depression-like effects caused by a seven weeks corticosterone treatment in the OF, NSF and FST.

In such test, 240 adult male mice of C57Bl/6Ntac strain (Taconic Farms (Denmark)), 8-10 weeks old, which are allowed to acclimate to the facility for at least 1 week prior to testing (e.g., 5 per cage under a 12 h (06:00-18:00) light-dark cycle at 22° C.) with food and water freely available.

A compound of the invention (30 or 60 mg/kg, per day in chow), fluoxetine (18 mg/kg per day in drinking water) or vehicle (0.45% β-cyclodextrine, βCD in drinking water) are administered to mice treated via drinking water with either vehicle or corticosterone (35 µg/mL). After 7 weeks of treatment as indicated below, mice are tested in the following behavioral tests: OF, NSF, FST and sucrose splash grooming test. Treatment is started with either βCD or corticosterone (35 µg/mL) given via the drinking water for 3 weeks (n=200 mice per group). Thereafter, administration with βCD or corticosterone will continue, and mice are divided into 8 groups of 30 mice as indicated below for 4 additional weeks.

| Week 1-8 | Week 3-7 |
|---|---|
| vehicle (βCD) | vehicle |
| vehicle (βCD) | fluoxetine, 18 mg/kg |
| vehicle (βCD) | test compound, 30 mg/kg |
| vehicle (βCD) | test compound, 60 mg/kg |
| 35 µg/mL/day corticosterone | vehicle |
| 35 µg/mL/day corticosterone | fluoxetine, 18 mg/kg |
| 35 µg/mL/day corticosterone | test compound, 30 mg/kg |
| 35 µg/mL/day corticosterone | test compound, 60 mg/kg |

Mice are tested in the behavioral paradigms in this order: OF, NSF, sucrose splash test and then the mouse FST (15 animals/group).

The Open-Field Test

Motor activity is quantified in Plexiglas® open field boxes 43×43 $cm^2$ (MED associates, Georgia, Vt.) over a 10 min session. Two sets of 16 pulse-modulated infrared photo beams are placed on opposite walls 2.5 cm apart to record x-y ambulatory movements. A 40-W white bulb placed in the middle of the room provided around 200-lx illumination at floor level. Activity chambers are computer interfaced for data sampling at 100 ms resolution. The computer defined grid lines that divided each open field into center and surrounds regions, with each of four lines being 11 cm from each wall. Dependant measures are total time spent in the center, the numbers of entries into the center and distance traveled in the center divided by total distance traveled. Overall motor activity is quantified as the total distance traveled (cm).

The Novelty-Suppressed Feeding

The novelty suppressed feeding (NSF) is a conflict test that elicits competing motivations: the drive to eat and the fear of venturing into the center of brightly lit arena. Latency to begin eating is used as an index of anxiety-like behavior because classical anxiolytic drugs decrease it. The NSF is carried out during a 5-min period as previously described (Santarelli et al., 2003). Briefly, the testing apparatus consisted of a plastic box 50×50×20 cm. The floor is covered with approximately 2 cm of wooden bedding. Twenty-four hours prior to behavioral testing, all food is removed from the home cage. At the time of testing, a single pellet of food (regular chow) is placed on a white paper platform positioned in the center of the box. An animal is placed in a corner of the maze and a stopwatch is immediately started. The measure of interest (chewing) is scored when the mouse is sitting on its haunches and biting with the use of forepaws. Immediately after this test, mice are transferred to their home cage and the amount of food consumed in 5 min is measured (home cage food consumption).

Mice are tested during the light period. Because antidepressants are known to have various effects on appetite, the feeding drive is assessed by returning animals in their home cage (familiar environment) immediately after the test. Then, the amount of food consumed over a 5 min-period is measured.

Splash Test

The grooming latency is assessed at the end of the corticosterone regimen (end of seventh week) in the presence or absence of 3-weeks of fluoxetine treatment. This test consists in squirting 200 μl of a 10% sucrose solution on the mouse's snout. The grooming frequency is then recorded The Mouse Forced Swim Test A modified forced swim test procedure as described in [Dulawa et al., Neuropsychopharmcol., 2004, 29, 1321-1330; Holick et al., Neuropsychopharmcol., 2008, 33, 2: 406-417] is used. Mice are placed individually into glass cylinders (height: 25 cm, diameter: 10 cm) containing 18 cm water that is maintained at 23-25° C. and videotaping will be for 6 min via a tripod-mounted camera positioned directly on the side of the cylinder. An increase of swimming and climbing has been linked to an activation of serotoninergic and noradrenergic system in rats [see, e.g., Cryan and Lucki, Pharmcol. & Exp. Therap., 2000, 295, 3, 1120-1126] and in mice [see, e.g., Dulawa et al. (2004); Holick et al., (2008)], respectively. Therefore, the predominant behavior (swimming, immobility or climbing) is scored here during the last 4 min of the 6 min testing period.

Anxiolytic-like properties also can be evaluated using these additional tests: (1) social interaction described in [S. E. File and P. Seth, *European Journal of Pharmacology,* 2003. 463, 35-53], and (2) elevated plus-maze described in [S. M. Korte and S. F. De Boer European Journal of Pharmacology, 2003, 463, 163-175].

Parkinson's disease (PD) can be assessed by measuring the neurotoxicity of MPTP in rats as described in [E. H. Lee et al. *Chin. J. Physiol.,* 1992, 35, 4: 317-36]. Also experimentally induced striatal DA depletion in animals is a valid model of Parkinsonism, as described in [W. Schultz *Prog. Neurobiol.,* 1982, 18, 2-3: 121-66]. The capacity of certain substances to damage catecholaminergic neurons has been used extensively to produce DA deficiency in animals, as described in [L. E. Annett et al. *Exp. Neurol.,* 1994, 125, 2: 228-46]. PD can also be assessed by measuring the neurotoxicity induced by 6-hydroxydopamine (6-OHDA) as described in N. Breysse et al. *J. Neurosci.,* 2002, 22, 13: 5669-5678; D. Rylander et al. *J. Pharmacol. Exp. Ther.,* 2009, 330, 1: 227-235; and L. Chen et al. *Brain Res.,* In Press, Uncorrected Proof, available online 21 Jun. 2009, doi:10.1016/j.brainres.2009.06.040].

Fragile X Syndrome can be assessed using the fmr1$^{tm1Cgr}$ mouse model as described in [Q. J. Yan et al. *Neuropharmacol.,* 2005, 49, 1053-1066] as well as the Fmr1 knockout mice with a selective reduction in mGluR5 expression as described in [G. Dölen et al. *Neuron,* 2007, 56, 955-962].

Preclinically, animals also can be evaluated for blockade/attenuation of symptoms associated with schizophrenia. Positive symptoms in animal models of schizophrenia can be evaluated by measuring changes in the overall level of activity of dopamine (DA) activity with concomitant parallel changes in locomotor activity as described in [R. Depoortere et al. *Neuropsychopharmacology,* 2003, 28, 11: 1889-902], D-amphetamine (AMPH) and phencyclidine (PCP) via induction of model psychosis or locomotor hyperactivity as described in [W. J. Freed et al. *Neuropharmacology,* 1984, 23, 2A: 175-81; F. Sams-Dodd *Neuropsychopharmacology,* 1998 19, 1: 18-25]. For example, Depoortere et al., 2003, have described tests for evaluating locomotor activity, catalepsy, climbing and stereotypy, which relate to positive symptomology and side effect profile, by characterizing compounds with typical and atypical antipsychotic efficacy. Attenuation in apomorphine-induced climbing, stereotypy and catalepsy (AIC) can be evaluated as described in [Y. K. Fung et al. *Pharmacol. Biochem. Behav.,* 1986, 24, 1: 139-41 and Y. K. Fung et al. *Steroids,* 1987, 49, 4-5: 287-94]. Additionally, negative symptoms of schizophrenia can be evaluated by measuring social interaction under the influence of NMDA antagonists such as PCP, as described in F. Sams-Dodd, 1998, supra.

Cognitive symptoms of memory, including those from Alzheimer's disease, can be evaluated by such models as the Fear Conditioning Paradigm described in [T. J. Gould et al. *Behav. Pharmacol.,* 2002, 13, 4: 287-94, and A. O. Hamm et al. *Brain,* 2003, 126, Pt 2: 267-75] and the Radial Arm Test described in [J. P. Aggleton et al. *Behav. Brain Res.,* 1996, 19, 2: 133-46], while spatial reference memory and learning can be evaluated in the Morris watermaze test as described in [Morris. *Learn. Motiv.,* 1981, 12, 239-260; B. Bontempi et al. *Eur. J. Neurosci.* 1996, 8, 11: 2348-60]. More specifically, in the Morris watermaze test, a circular water tank (150 cm diameter and 45 cm height) is filled with about 30 cm water and maintained at 26-28° C. with an escape platform (15 cm diameter) 18 cm from the perimeter and always in the same position 1.5 cm beneath the surface of the water. The water is made opaque by addition of a non-toxic coloring agent (e.g., milk powder) rendering the platform invisible. Animals are given a single training session over a single day. The training session consists of 4 consecutive trials in the watermaze, each separated by 60 seconds. For each trial, the animal is placed in the watermaze at one of two starting points equidistant from the escape platform and allowed to find the escape platform. The animal is left on the escape platform for 60 seconds before starting a new trial. If the animal does not find the platform within 120 seconds, the animal is removed from the water and placed on the platform for 60 seconds. During the 4 trials, the animals start the watermaze twice from each starting point in a randomly determined order per animal. Appropriate animals for testing with acclimatization conditions are, for example, the male Rj: Wistar (Hans) rats as previously described for the LES test.

The trials are video-recorded and the behavior of animals is analyzed using a video-tracking system (SMART, Panlab, S.L., Cornellá (Barcelona), Spain). The principal measure taken in each trial is the distance traveled to find the platform. Secondary measures taken are the swim speed and escape latency. The test is performed blind using, for example, 12 rats per test group. Testing includes multiple tests using reference compounds and compounds of the present invention that are prepared and administered as previously described LES test. For each test, data is analyzed by comparing treated groups with vehicle controls using one-way ANOVA followed by Dunnett's t tests. To increase comparability with the aforementioned Vogel conflict test, in all tests, rats are subjected to water-deprivation for approximately 24 h before the test (Day 1); however, testing is performed in non water-deprived rats (Day 2).

Additionally, with respect to cognition, memory and hippocampal hypo-functioning can be assessed by measuring the restoration of synaptic plasticity in ovariectomized (OVX) female rats as described in [M. Day and M. Good *Neurobiol. Learn. Mem.,* 2005, 83, 1: 13-21]. Further, changes in attention function because of schizophrenia can be examined by the Five (5) Choice Serial Reaction Time Test (5CSRT) described in [J. L. Muir et al. *Psychopharmacology (Berl),* 1995, 118, 1: 82-92 and Robbins et al. *Ann. N.Y. Acad. Sci.,* 1998, 846, 222-37].

Human patients can be evaluated for cognitive diseases or disorders by any of the tests within the skill of those in the art.

Analgesic activity can be evaluated by neuropathic pain model (the "Chung model") as described in [Kim and Chung, Pain, 1992, 50, 355-363]. Tight ligature of spinal nerves in rats is associated with hyperalgesia, allodynia and spontaneous pain, and therefore constitutes a model for peripheral neuropathic pain in humans. Antihyperalgesics reduce these chronic signs of pain hypersensitivity. Thus, in the Chung model, rats are anesthetized (sodium pentobarbital 50 mg/kg i.p.) and an incision at the L4-S2 level is performed to expose the left L5 nerve after cleaning the flank with chlorhexidine in spray. A cotton thread (standard, non-surgery quality), disinfected with pure alcohol, is placed around the L5 nerve and a simple ligature is tied tightly around the L5 nerve. The wound is then sutured and sprayed with CothiVet® (hydrocotyle tincture spray) (Neogen® Corp., Lexington, Ky.). The rats receive a s.c. injection of Clamoxyl (0.67 mL/kg) and are allowed to recover. At least 2 weeks after the surgery, when the chronic pain state is fully installed, rats are submitted consecutively to tactile and thermal stimulation of both hindpaws.

For tactile stimulation, the animal is placed under an inverted acrylic plastic box (18×11.5×13 cm) on a grid floor. The tip of an electronic Von Frey probe (Model 1610, BIO-SEB, Vitrolles Cedex, France) is then applied with increasing force first to the non-lesioned and then the lesioned hindpaw and the force required to induce paw-withdrawal is automatically recorded. This procedure is carried out 3 times and the mean force per paw is calculated.

For heat stimulation, the apparatus (No. 7371, Ugo Basile, Comerio VA, Italy) consists of individual acrylic plastic boxes (17×11×13 cm) placed upon an elevated glass floor. A rat is placed in the box and left free to habituate for 10 minutes. A mobile infrared radiant source (96±10 mW/cm$^2$) is then focused first under the non-lesioned and then the lesioned hindpaw and the paw-withdrawal latency is automatically recorded. In order to prevent tissue damage, the heat source is automatically turned off after 45 seconds.

Prior to receiving compound treatment all animals are submitted to tactile stimulation of the hindpaws and assigned to treatment groups matched on the basis of the pain response of the lesioned hindpaw. The test is performed blind using, for example, 10 water-deprived rats per group. Appropriate animals for testing are, for example, the male Rj: Wistar (Hans) rats as previously described for the LES test. Testing includes multiple tests using reference compounds and compounds of the present invention. In addition to the pregabalin and MPEP as previously described for the LES test, duloxetine can be used as a reference compound since it is an antihyperalgesic with respect to neuropathic pain associated with diabetes and fibromyalgia. Compounds are prepared and administered as previously described LES test. Testing can be performed using the same batch of operated rats repeatedly, with a minimum wash-out of 1 week between treatments. Also, to increase comparability with the aforementioned Vogel conflict test, in all tests, rats are subjected to water-deprivation for approximately 48 hours before each test. For each Chung model test, data will be analyzed by comparing treated groups with appropriate controls using unpaired Student's t tests.

Additionally, analgesic/anti-inflammatory activity can be evaluated in vivo using the Formalin Paw Test in the mouse such as that described by [Wheeler-Aceto et al, Psychopharmacology, 1991, 104, 35-44]. For the test, mice are given an intraplantar injection of 5% formalin (25 µl) into the posterior left paw. This treatment induces paw licking in control animals. The time spent licking is counted for 5 minutes, beginning immediately after injection of formalin (early phase) and for 15 minutes starting 15 minutes after injection of formalin (late phase).

The test is performed blind using, e.g., 10 mice per group. Appropriate animals for testing are, for example, male Rj: NMRI mice (Elevage Janvier), weighing 20-30 g (max. range per experiment=5 g) at the beginning of testing. Animals are acclimatized as described for the animals used in the LES test. Testing includes multiple tests using reference compounds (e.g., morphine), comparative compounds (e.g., gabapentin and duloxetine), and compounds of the present invention. Compounds of the invention can be evaluated at multiple doses as previously described in the LES test, and administered s.c. 60 minutes before formalin in comparison with a vehicle control group, while morphine (64 mg/kg p.o.), gabapentin (300 mg/kg p.o.) and duloxetine (10 mg/kg p.o.) are administered p.o. 60 minutes before formalin. Data is analyzed by comparing treated groups with vehicle control groups using unpaired Mann-Whitney U tests.

Multiple sclerosis can be evaluated by the experimental autoimmune encephalomyelitis (EAE) model described in [H. Y. Liu et al. J. Neurosci. Res., 2002, 70, 2: 238-48].

Those skilled in the art will recognize that various changes and/or modifications may be made to aspects or embodiments of this invention and that such changes and/or modifications may be made without departing from the spirit of this invention. Therefore, it is intended that the appended claims cover all such equivalent variations as will fall within the spirit and scope of this invention.

Each reference cited in the present application, including literature references, books, patents and patent applications, is incorporated herein by reference in its entirety.

What is claimed is:

1. A method of treating a disease or disorder selected from a mood disorder or anxiety, the method comprises administering a therapeutically effective amount of a compound of formula (I):

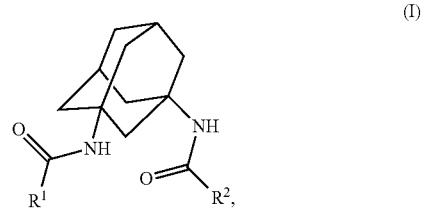

wherein:
$R^1$ and $R^2$ are each independently alkyl, cycloalkyl, ketocycloalkyl, heterocyclyl, aryl or heteroaryl, wherein each is optionally mono-, di-, or tri-substituted independently with alkyl, alkoxy, halogen, cyano, nitro, trifluoroalkyl, amino, alkylamino, dialkylamino, acyl, aryl, heteroaryl, heterocyclyl, heterocyclyl-$R^3$, —NHR$^3$, —N(alkyl)R$^3$, —C(O)NHR$^3$, —C(O)N(alkyl)R$^3$, —NHC(O)R$^3$, —N(alkyl)C(O)R$^3$, —OH or —OR$^3$, wherein:
$R^3$ is $C_1$-$C_6$alkyl or $C_1$-$C_6$cycloalkyl, which is optionally substituted with halogen, $C_1$-$C_3$alkoxy, OH, —CN, —NH$_2$, —NH($C_1$-$C_3$alkyl), —N($C_1$-$C_3$alkyl)$_2$, $C_1$-$C_3$alkylheterocyclyl, $C_1$-$C_3$alkylcarbamate, —C(O)NH($C_1$-$C_3$alkyl), —C(O)N($C_1$-$C_3$alkyl)$_2$, —NHC(O)—$C_1$-$C_3$alkyl, —N($C_1$-$C_3$alkyl)-C(O)—$C_1$-$C_3$alkyl, OH, or —O—$C_1$-$C_6$alkyl;

with the proviso that the compound of formula (I) is not:
N,N'-(1,3-adamantylene)bis(3-methoxy-benzamide);
N,N'-(1,3-adamantylene)bis(4-ethoxy-benzamide);
N,N'-(1,3-adamantylene)bis(4-methoxy-benzamide);
N,N'-(1,3-adamantylene)bis(3,4,5-trimethoxybenzamide);
N,N'-(1,3-adamantylene)bis(2-iodo-benzamide);
N,N'-(1,3-adamantylene)bis-benzamide;
N,N'-(1,3-adamantylene)bis(3-nitrobenzamide); and
N,N'-(1,3-adamantylene)bis-(3-pyridinecarboxamide) or a pharmaceutically acceptable salt thereof to a mammal in need thereof.

2. The method of claim 1, wherein the mammal is a human.

3. The method of claim 1, wherein the mood disorder is a depression.

4. The method of claim 3, wherein the depression is selected from the group consisting of atypical depression, bipolar depression, unipolar depression, major depression, endogenous depression, involutional depression, reactive depression, postpartum depression, primary depression, psychotic depression, secondary depression, a combination thereof.

5. The method of claim 1, wherein the anxiety disease or disorder is selected from a group comprising generalized anxiety disorder, panic anxiety, obsessive compulsive disorder, social phobia, performance anxiety, post-traumatic stress disorder, acute stress reaction, an adjustment disorder, a hypochondriacal disorder, separation anxiety disorder, agoraphobia, a specific phobia, anxiety disorder due to general medical condition, substance-induced anxiety disorder, alcohol withdrawal-induced anxiety, and a combination thereof.

6. The method of claim 1, wherein at least one symptom of the disease or disorder is treated.

7. The method of claim 6, wherein the disease or disorder is a depression.

8. The method of claim 7, wherein the at least one symptom of the depression is depressed feeling, depressed mood, loss of interest or pleasure in some or all activities, changes in appetite, changes in weight, changes in sleep patterns, lack of energy, fatigue, low self esteem, diminished capacity for thinking, concentration, or decisiveness, feelings of hopelessness or worthlessness, psychomotor agitation or retardation, self-reproach, inappropriate guilt, frequent thoughts of death or suicide, plans or attempts to commit suicide, or a combination thereof.

9. The method of claim 6, wherein the disease or disorder is an anxiety.

10. The method of claim 9, wherein the at least one symptom of the anxiety is apprehension, fear, trembling, muscle aches, insomnia, abdominal upsets, dizziness, irritability, persistent, recurring thoughts, compulsions, heart palpitations, chest pain, chest discomfort, sweating, tingling sensations, feeling of choking, fear of losing control, flashbacks, nightmares, intrusive thoughts, intrusive recollections, avoidance behaviors, emotional numbing, an inability to sleep, anxious feelings, overactive startle response, hypervigilance, outbursts of anger, faintness, blushing, profuse sweating, gastroesophageal reflux or a combination thereof.

11. The method of claim 1, wherein the compound is selected from the group consisting of N,N'-(1,3-adamantylene)bis(6-methyl-pyridine-2-carboxamide); N,N'-(1,3-adamantylene)bis(2-pyridinecarboxamide); N,N'-(1,3-adamantylene)bis(3-cyano-benzamide); 2-methyl-2H-indazole-3-carboxylic acid {3-[(pyridine-2-carbonyl)-amino]-adamantan-1-yl}-amide; 6-methyl-pyridine-2-carboxylic acid {3-[(2-methyl-cyclopropanecarbonyl)-amino]-adamantan-1-yl}-amide; pyrimidine-4-carboxylic acid {3-[(pyridine-2-carbonyl)-amino]-adamantan-1-yl}-amide; and 2-methyl-benzoxazole-6-carboxylic acid {3-[(pyridine-2-carbonyl)-amino]-adamantan-1-yl}-amide or a pharmaceutically acceptable salt thereof.

12. The method of claim 1, wherein the compound is selected from the group consisting of 6-methyl-pyrazine-2-carboxylic acid {3-[(pyridine-2-carbonyl)-amino]-adamantan-1-yl}-amide; 6-{3-[(pyridine-2-carbonyl)-amino]-adamantan-1-yl-carbamoyl}-3,4-dihydro-1H-isoquinoline-2-carboxylic acid tert-butyl ester; pyridine-2-carboxylic acid [3-(3-methoxy-benzoylamino)-adamantan-1-yl]-amide; imidazo[1,2-a]pyridine-7-carboxylic acid [3-(3-fluoro-benzoylamino)-adamantan-1-yl]-amide; and 6-methyl-pyrazine-2-carboxylic acid {3-[(2-methyl-thiazole-4-carbonyl)-amino]-adamantan-1-yl}-amide or a pharmaceutically acceptable salt thereof.

* * * * *